United States Patent
Zhang et al.

(10) Patent No.: US 9,738,719 B2
(45) Date of Patent: Aug. 22, 2017

(54) METHODS AND COMPOSITIONS RELATED TO MODULATORS OF EUKARYOTIC CELLS

(71) Applicants: THE SCRIPPS RESEARCH INSTITUTE, La Jolla, CA (US); Hongkai Zhang, San Diego, CA (US); Ian A. Wilson, La Jolla, CA (US); Richard A. Lerner, La Jolla, CA (US)

(72) Inventors: Hongkai Zhang, San Diego, CA (US); Ian A. Wilson, La Jolla, CA (US); Richard A. Lerner, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 238 days.

(21) Appl. No.: 14/424,663

(22) PCT Filed: Aug. 16, 2013

(86) PCT No.: PCT/US2013/055362
§ 371 (c)(1),
(2) Date: Feb. 27, 2015

(87) PCT Pub. No.: WO2014/035693
PCT Pub. Date: Mar. 6, 2014

(65) Prior Publication Data
US 2015/0316561 A1    Nov. 5, 2015

Related U.S. Application Data

(60) Provisional application No. 61/695,527, filed on Aug. 31, 2012, provisional application No. 61/814,646, filed on Apr. 22, 2013.

(51) Int. Cl.
*C40B 30/06* (2006.01)
*C07K 16/28* (2006.01)
(Continued)

(52) U.S. Cl.
CPC .......... *C07K 16/2863* (2013.01); *C07K 14/71* (2013.01); *C07K 14/7153* (2013.01);
(Continued)

(58) Field of Classification Search
None
See application file for complete search history.

(56) References Cited

U.S. PATENT DOCUMENTS

2003/0104402 A1* 6/2003 Zauderer ............... C07K 16/00
435/6.14
2005/0282181 A1 12/2005 Yang et al.

FOREIGN PATENT DOCUMENTS

EP        2 360 267 A2    8/2011

OTHER PUBLICATIONS

Alten, et al., "The human anti-IL-1β monoclonal antibody ACZ885 is effective in joint inflammation models in mice and in a proof-of-concept study in patients with rheumatoid arthritis", *Arthritis Research & Therapy* 10: 1-9 (2008).
(Continued)

*Primary Examiner* — Christian Boesen
(74) *Attorney, Agent, or Firm* — Hugh Wang; Thomas Fitting

(57) ABSTRACT

Methods for Identifying protein modulators of eukaryotic cells by expressing a combinatorial library of potential agonists inside a eukaryotic cell and then directly selecting for an agonist of a target molecule. Some methods involve co-culturing a cell expressing a combinatorial library of potential agonists and a second cell, and then selecting agents that modulate a phenotype of or a desired cellular response in the second cell. Preferably, the agonists are antibodies introduced into and expressed in the starting cells, such as agonist anti-EpoR, anti-TpoR, or G-CSFR antibodies. Also disclosed are methods for selecting from
(Continued)

combinatorial antibody libraries bispecific antibodies that can regulate cell phenotypes.

20 Claims, 12 Drawing Sheets

(51) Int. Cl.
G01N 33/68 (2006.01)
G01N 33/74 (2006.01)
C07K 14/71 (2006.01)
C07K 14/715 (2006.01)

(52) U.S. Cl.
CPC ...... *C07K 16/2839* (2013.01); *C07K 16/2866* (2013.01); *G01N 33/6845* (2013.01); *G01N 33/6854* (2013.01); *G01N 33/746* (2013.01); *C07K 2317/21* (2013.01); *C07K 2317/31* (2013.01); *C07K 2317/35* (2013.01); *C07K 2317/622* (2013.01); *C07K 2317/74* (2013.01); *C07K 2317/75* (2013.01); *C07K 2317/92* (2013.01); *C07K 2319/30* (2013.01); *C40B 30/06* (2013.01)

(56) References Cited

OTHER PUBLICATIONS

Bowers, et al., "Coupling mammalian cell surface display with somatic hypermutation for the discovery and maturation of human antibodies"; *PNAS* 108(51): 20455-20460 (2011).

Gao, et al., "A method for the generation of combinatorial antibody libraries using pIX phage display", *PNAS* 99 (20); 12612-12616 (2002).

Manning, et al., Interleukin-10 Delivery via Mesenchymal Stem Cells: A Novel Gene Therapy Approach to Prevent Lung Ischemia-Reperfusion Injury, *Human Gene therapy* 21; 713-727 (2010).

* cited by examiner

SEQUENCE LISTING

<160> NUMBER OF SEQ ID NOS: 83

<210> SEQ ID NO 1
<211> LENGTH: 8
<212> TYPE: PRT
<213> ORGANISM: Homo sapiens

<400> SEQUENCE: 1

Gly Tyr Thr Phe Thr Gly Tyr Tyr
1               5

<210> SEQ ID NO 2
<211> LENGTH: 8
<212> TYPE: PRT
<213> ORGANISM: Homo sapiens

<400> SEQUENCE: 2

Ile Asn Pro Asn Ser Gly Gly Thr
1               5

<210> SEQ ID NO 3
<211> LENGTH: 13
<212> TYPE: PRT
<213> ORGANISM: Homo sapiens

<400> SEQUENCE: 3

Cys Ala Arg Leu Ser Ser Gly Trp Thr Phe Asp Tyr Trp
1               5                   10

<210> SEQ ID NO 4
<211> LENGTH: 12
<212> TYPE: PRT
<213> ORGANISM: Homo sapiens

<400> SEQUENCE: 4

Gln Ser Val Leu Tyr Ser Pro Asn Asn Lys Asn Tyr
1               5                   10

<210> SEQ ID NO 5
<211> LENGTH: 0
<212> TYPE: PRT
<213> ORGANISM: Homo sapiens

<400> SEQUENCE: 5

000

<210> SEQ ID NO 6
<211> LENGTH: 11
<212> TYPE: PRT
<213> ORGANISM: Homo sapiens

<400> SEQUENCE: 6

Cys Gln Gln Ser Tyr Ser Leu Pro Phe Thr Phe
1               5                   10

<210> SEQ ID NO 7
<211> LENGTH: 120
<212> TYPE: PRT
<213> ORGANISM: Homo sapiens

<400> SEQUENCE: 7

Met Ala Gln Val Gln Leu Val Glu Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Gly Tyr Tyr Met His Trp Val Arg Gln Ala Pro Gly Gln Gly Leu Glu
        35                  40                  45

Trp Met Gly Trp Ile Asn Pro Asn Ser Gly Gly Thr Asn Tyr Ala Gln
50                  55                  60

Lys Phe Gln Gly Arg Val Thr Met Thr Arg Asp Thr Ser Ile Ser Thr
65                  70                  75                  80

Ala Tyr Met Glu Leu Ser Arg Leu Arg Ser Asp Asp Thr Ala Val Tyr
                85                  90                  95

Tyr Cys Ala Arg Leu Ser Ser Gly Trp Thr Phe Asp Tyr Trp Gly Gln
            100                 105                 110

Gly Thr Leu Val Thr Val Ser Ser
        115                 120

<210> SEQ ID NO 8
<211> LENGTH: 114
<212> TYPE: PRT
<213> ORGANISM: Homo sapiens

<400> SEQUENCE: 8

Glu Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Pro Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Glu Arg Phe Ser Gly Ser Gly Ser Gly Thr Asp Phe Thr Leu Thr
65                  70                  75                  80

Ile Ser Ser Leu His Ala Glu Asp Val Ala Leu Tyr Tyr Cys Gln Gln
                85                  90                  95

Ser Tyr Ser Leu Pro Phe Thr Phe Gly Pro Gly Thr Lys Val Glu Ile
            100                 105                 110

Lys Arg

<210> SEQ ID NO 9
<211> LENGTH: 8
<212> TYPE: PRT
<213> ORGANISM: Homo sapiens

<400> SEQUENCE: 9

Gly Gly Thr Phe Ser Ser Tyr Ala
1               5

<210> SEQ ID NO 10
<211> LENGTH: 8
<212> TYPE: PRT
<213> ORGANISM: Homo sapiens

```
<400> SEQUENCE: 10

Ile Ile Pro Ile Phe Gly Thr Ala
1               5

<210> SEQ ID NO 11
<211> LENGTH: 17
<212> TYPE: PRT
<213> ORGANISM: Homo sapiens

<400> SEQUENCE: 11

Cys Ala Arg Asp Gln Gly Tyr Tyr Tyr Gly Ser Gly Gly Leu Asp Tyr
1               5                   10                  15

Trp

<210> SEQ ID NO 12
<211> LENGTH: 6
<212> TYPE: PRT
<213> ORGANISM: Homo sapiens

<400> SEQUENCE: 12

Gln Ser Ile Ser Ser Tyr
1               5

<210> SEQ ID NO 13
<211> LENGTH: 3
<212> TYPE: PRT
<213> ORGANISM: Homo sapiens

<400> SEQUENCE: 13

Ala Ala Ser
1

<210> SEQ ID NO 14
<211> LENGTH: 11
<212> TYPE: PRT
<213> ORGANISM: Homo sapiens

<400> SEQUENCE: 14

Cys Leu Gln Asp Tyr Asn Tyr Pro Leu Thr Phe
1               5                   10

<210> SEQ ID NO 15
<211> LENGTH: 8
<212> TYPE: PRT
<213> ORGANISM: Homo sapiens

<400> SEQUENCE: 15

Gly Tyr Thr Phe Thr Ser Tyr Gly
1               5

<210> SEQ ID NO 16
<211> LENGTH: 8
<212> TYPE: PRT
<213> ORGANISM: Homo sapiens

<400> SEQUENCE: 16

Ile Ser Ala Tyr Asn Gly Asn Thr
1               5

<210> SEQ ID NO 17
<211> LENGTH: 12
<212> TYPE: PRT
<213> ORGANISM: Homo sapiens
```

<400> SEQUENCE: 17

Cys Ala Arg Gly Val Ala Ala Ala Leu Ser Tyr Trp
1               5                   10

<210> SEQ ID NO 18
<211> LENGTH: 9
<212> TYPE: PRT
<213> ORGANISM: Homo sapiens

<400> SEQUENCE: 18

Ser Ser Asp Val Gly Ala Tyr Asn Tyr
1               5

<210> SEQ ID NO 19
<211> LENGTH: 3
<212> TYPE: PRT
<213> ORGANISM: Homo sapiens

<400> SEQUENCE: 19

Glu Val Thr
1

<210> SEQ ID NO 20
<211> LENGTH: 12
<212> TYPE: PRT
<213> ORGANISM: Homo sapiens

<400> SEQUENCE: 20

Cys Ile Ser Phe Thr Ala Ser Ser Thr Trp Ala Phe
1               5                   10

<210> SEQ ID NO 21
<211> LENGTH: 124
<212> TYPE: PRT
<213> ORGANISM: Homo sapiens

<400> SEQUENCE: 21

Met Ala Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Phe Ser
                20                  25                  30

Ser Tyr Ala Ile Ser Trp Val Arg Gln Ala Pro Gly Gln Gly Leu Glu
            35                  40                  45

Trp Met Gly Gly Ile Ile Pro Ile Phe Gly Thr Ala Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Asp Gln Gly Tyr Tyr Gly Ser Gly Gly Leu Asp
            100                 105                 110

Tyr Trp Gly Gln Gly Thr Leu Val Thr Val Ser Ser
        115                 120

<210> SEQ ID NO 22
<211> LENGTH: 107
<212> TYPE: PRT
<213> ORGANISM: Homo sapiens

<400> SEQUENCE: 22

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Leu
                85                  90                  95

Thr Phe Gly Gly Gly Thr Lys Val Glu Ile Lys
            100                 105
```

<210> SEQ ID NO 23
<211> LENGTH: 119
<212> TYPE: PRT
<213> ORGANISM: Homo sapiens

<400> SEQUENCE: 23

```
Met Ala Gln Val Gln Leu Val Gln Ser Gly Ala Glu Val Lys Lys Pro
 1               5                  10                  15

Gly Ala Ser Val Lys Val Ser Cys Lys Ala Ser Gly Tyr Thr Phe Thr
            20                  25                  30

Ser Tyr Gly Ile Ser Trp Val Arg Gln Ala Pro Gly Gln Gly Leu Glu
        35                  40                  45

Trp Met Gly Trp Ile Ser Ala Tyr Asn Gly Asn Thr Asn Tyr Ala Gln
50                  55                  60

Lys Leu Gln Gly Arg Val Thr Met Thr Thr Asp Thr Ser Thr Ser Thr
65                  70                  75                  80

Ala Tyr Met Glu Leu Arg Ser Leu Arg Ser Asp Asp Thr Ala Val Tyr
                85                  90                  95

Tyr Cys Ala Arg Gly Val Ala Ala Ala Leu Ser Tyr Trp Gly Gln Gly
            100                 105                 110

Thr Leu Val Thr Val Ser Ser
        115
```

<210> SEQ ID NO 24
<211> LENGTH: 111
<212> TYPE: PRT
<213> ORGANISM: Homo sapiens

<400> SEQUENCE: 24

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Glu Val Thr Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ile Ser Phe Thr Ala Ser
                85                  90                  95
```

```
Ser Thr Trp Ala Phe Gly Gly Gly Thr Lys Leu Thr Val Leu Gly
            100                 105                 110
```

<210> SEQ ID NO 25
<211> LENGTH: 360
<212> TYPE: DNA
<213> ORGANISM: Homo sapiens

<400> SEQUENCE: 25

```
atggcacagg tgcagctggt ggagtctggg gctgaggtga agaagcctgg ggcctcagtg      60
aaggtctcct gcaaggcttc tggatacacc ttcaccggct actatatgca ctgggtgcga     120
caggcccctg gacaagggct tgagtggatg ggatggatca cccctaacag tggtggcaca     180
aactatgcac agaagtttca gggcagggtc accatgacca gggacacgtc catcagcaca     240
gcctacatgg agctgagcag gctgagatct gacgacacgg ccgtgtatta ctgtgcgaga     300
cttagcagtg gctggacctt tgactactgg ggccagggaa ccctggtcac cgtctcctca     360
```

<210> SEQ ID NO 26
<211> LENGTH: 342
<212> TYPE: DNA
<213> ORGANISM: Homo sapiens

<400> SEQUENCE: 26

```
gaaattgtgc tgactcagtc tccagactcc ctggctgtgt ctctgggcga gagggccacc      60
atcaactgca gtccagcca gagtgtttta tacagcccca caataagaa ctatttagct      120 tggtatcagc agaaaccagg acagcctcct aagctactca tttactgggc gtctacccgg     180
gagtccgggg tccccgagcg attcagtggc agcgggtctg ggacagattt cactctcacc     240
atcagcagcc tgcacgctga agatgtggca ctttattact gtcagcagtc ttatagtctt     300
ccattcactt tcggccctgg gaccaaggtg gagatcaaac gt                        342
```

<210> SEQ ID NO 27
<211> LENGTH: 372
<212> TYPE: DNA
<213> ORGANISM: Homo sapiens

<400> SEQUENCE: 27

```
atggcacagg tgcagctggt gcaatctggg gctgaggtga agaagcctgg gtcctcggtg      60
aaggtctcct gcaaggcttc tggaggcacc ttcagcagct atgctatcag ctgggtgcga     120
caggcccctg gacaagggct tgagtggatg ggagggatca tccctatctt tggtacagca     180
aactacgcac agaagttcca gggcagagtc acgattaccg cggacgaatc cacgagcaca     240
gcctacatgg agctgagcag cctgagatct gaggacacgg ccgtgtatta ctgtgcgaga     300 gatcagggt attactatgg ttcggggggg cttgactact ggggccaggg aaccctggtc     360
accgtctcct ca                                                        372
```

<210> SEQ ID NO 28
<211> LENGTH: 321
<212> TYPE: DNA
<213> ORGANISM: Homo sapiens

<400> SEQUENCE: 28

```
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
```

```
aggttcagcg gcagtggatc tggcacagat ttcactctca ccatcagcag cctgcagcct      240
gaagattttg caacttatta ctgtctacaa gattacaatt acccgctcac tttcggcgga      300
gggaccaagg tggagatcaa a                                                321
```

<210> SEQ ID NO 29
<211> LENGTH: 357
<212> TYPE: DNA
<213> ORGANISM: Homo sapiens

<400> SEQUENCE: 29

```
atggcacagg tgcagctggt gcaatctggg gctgaggtga agaagcctgg ggcctcagtg      60
aaggtctcct gcaaggcttc tggttacacc tttaccagct atggtatcag ctgggtgcga     120
caggcccctg gacaagggct tgagtggatg ggatggatca cgcttacaa tggtaacaca      180 aactatgcac agaagctcca gggcagagtc accatgacca cagacacatc cacgagcaca     240
gcctacatgg aactgaggag cctgagatct gacgacacgg ccgtgtatta ctgtgcgaga     300
ggagtagcag cagcttttatc ctactggggc cagggcaccc tggtcaccgt ctcctca       357
```

<210> SEQ ID NO 30
<211> LENGTH: 333
<212> TYPE: DNA
<213> ORGANISM: Homo sapiens

<400> SEQUENCE: 30

```
cagtctgccc tgactcagcc tgcctccgtg tctgggtctc ctggacagtc gatcaccatc      60
tcctgcactg gaaccagcag tgacgttggt gcttataact atgtctcctg gtaccaacag     120
cacccaggca aagcccccaa actcatgatt tatgaggtca ctaagcggcc ctcaggggtc     180
cctgatcgct tctctgggtc caagtctggc aacacggcct ccctgaccat ctctgggctc     240
caggctgagg acgaggctga ttattactgc atctctttta gcctcctc cacttgggcg      300 ttcggcggag ggaccaagct gaccgtccta ggt                                  333
```

<210> SEQ ID NO 31
<211> LENGTH: 21
<212> TYPE: PRT
<213> ORGANISM: Homo sapiens

<400> SEQUENCE: 31

```
Gly Ser Gly Glu Gly Arg Gly Ser Leu Leu Thr Cys Gly Asp Val Glu
1               5                   10                  15

Glu Asn Pro Gly Pro
            20
```

<210> SEQ ID NO 32
<211> LENGTH: 243
<212> TYPE: PRT
<213> ORGANISM: Homo sapiens

<400> SEQUENCE: 32

```
Met Ala Gln Val Gln Leu Val Gln Ser Gly Ala Glu Val Arg Lys Val
1               5                   10                  15

Gly Ser Ser Val Lys Val Ser Cys Lys Ala Ser Arg Asp Thr Phe Asn
            20                  25                  30

Thr Tyr Gly Ile Ser Trp Val Arg Gln Ala Pro Gly Gln Gly Leu Glu
        35                  40                  45

Trp Met Gly Gly Ile Ile Pro Ile Phe Gly Thr Ala Asp Tyr Ala Gln
    50                  55                  60
```

```
Lys Phe Arg Gly Arg Val Thr Ile Thr Ala Asp Glu Ser Thr Ser Thr
 65                  70                  75                  80

Ala Tyr Met Glu Leu Ser Ser Leu Arg Ser Glu Asp Thr Ala Val Tyr
                 85                  90                  95

Tyr Cys Ala Arg Asp Arg Lys Leu Gly Gly Ser Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Asp Ile Val Met Thr Gln Ser Pro Ser
130                 135                 140

Ser Val Ser Ala Ser Val Gly Asp Lys Val Thr Ile Thr Cys Arg Ala
145                 150                 155                 160

Ser Gln Gly Leu Gly Arg Trp Leu Ala Trp Tyr Gln Gln Glu Pro Gly
                165                 170                 175

Lys Ala Pro Lys Leu Leu Ile Tyr Ala Ala Ser Thr Leu Gln Arg Gly
            180                 185                 190

Val Pro Ser Arg Phe Ser Gly Ser Gly Ser Gly Thr Asp Phe Thr Leu
            195                 200                 205

Thr Ile Ser Ser Leu Gln Pro Glu Asp Phe Ala Thr Tyr Tyr Cys Gln
    210                 215                 220

Gln Ser Asn Ser Phe Pro Trp Thr Phe Gly Gln Gly Thr Lys Leu Glu
225                 230                 235                 240

Ile Lys Arg

<210> SEQ ID NO 33
<211> LENGTH: 120
<212> TYPE: PRT
<213> ORGANISM: Homo sapiens

<400> SEQUENCE: 33

Met Ala Gln Val Gln Leu Val Gln Ser Gly Ala Glu Val Arg Lys Val
 1               5                  10                  15

Gly Ser Ser Val Lys Val Ser Cys Lys Ala Ser Arg Asp Thr Phe Asn
                20                  25                  30

Thr Tyr Gly Ile Ser Trp Val Arg Gln Ala Pro Gly Gln Gly Leu Glu
             35                  40                  45

Trp Met Gly Gly Ile Ile Pro Ile Phe Gly Thr Ala Asp Tyr Ala Gln
 50                  55                  60

Lys Phe Arg Gly Arg Val Thr Ile Thr Ala Asp Glu Ser Thr Ser Thr
 65                  70                  75                  80

Ala Tyr Met Glu Leu Ser Ser Leu Arg Ser Glu Asp Thr Ala Val Tyr
                 85                  90                  95

Tyr Cys Ala Arg Asp Arg Lys Leu Gly Gly Ser Asp Tyr Trp Gly Gln
            100                 105                 110

Gly Thr Leu Val Thr Val Ser Ser
        115                 120

<210> SEQ ID NO 34
<211> LENGTH: 108
<212> TYPE: PRT
<213> ORGANISM: Homo sapiens

<400> SEQUENCE: 34

Asp Ile Val Met Thr Gln Ser Pro Ser Ser Val Ser Ala Ser Val Gly
 1               5                  10                  15
```

-continued

```
Asp Lys Val Thr Ile Thr Cys Arg Ala Ser Gln Gly Leu Gly Arg Trp
             20                  25                  30
Leu Ala Trp Tyr Gln Gln Glu Pro Gly Lys Ala Pro Lys Leu Leu Ile
         35                  40                  45
Tyr Ala Ala Ser Thr Leu Gln Arg Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Asn Ser Phe Pro Trp
                 85                  90                  95
Thr Phe Gly Gln Gly Thr Lys Leu Glu Ile Lys Arg
            100                 105
```

<210> SEQ ID NO 35
<211> LENGTH: 8
<212> TYPE: PRT
<213> ORGANISM: Homo sapiens

<400> SEQUENCE: 35

```
Arg Asp Thr Phe Asn Thr Tyr Gly
1               5
```

<210> SEQ ID NO 36
<211> LENGTH: 8
<212> TYPE: PRT
<213> ORGANISM: Homo sapiens

<400> SEQUENCE: 36

```
Ile Ile Pro Ile Phe Gly Thr Ala
1               5
```

<210> SEQ ID NO 37
<211> LENGTH: 13
<212> TYPE: PRT
<213> ORGANISM: Homo sapiens

<400> SEQUENCE: 37

```
Cys Ala Arg Asp Arg Lys Leu Gly Gly Ser Asp Tyr Trp
1               5                   10
```

<210> SEQ ID NO 38
<211> LENGTH: 6
<212> TYPE: PRT
<213> ORGANISM: Homo sapiens

<400> SEQUENCE: 38

```
Gln Gly Leu Gly Arg Trp
1               5
```

<210> SEQ ID NO 39
<211> LENGTH: 9
<212> TYPE: PRT
<213> ORGANISM: Homo sapiens

<400> SEQUENCE: 39

```
Gln Gln Ser Asn Ser Phe Pro Trp Thr
1               5
```

<210> SEQ ID NO 40
<211> LENGTH: 245
<212> TYPE: PRT
<213> ORGANISM: Homo sapiens

<400> SEQUENCE: 40

Met Ala Gln Val Gln Leu Leu Glu Ser Gly Pro Gly Leu Val Lys Pro
1               5                   10                  15

Ser Gln Thr Leu Ser Leu Thr Cys Thr Val Ser Gly Gly Ser Ile Ser
            20                  25                  30

Ser Gly Gly Tyr Tyr Trp Ser Trp Ile Arg Gln Pro Pro Gly Lys Gly
        35                  40                  45

Leu Glu Trp Ile Gly Tyr Ile Tyr Tyr Ser Gly Ser Thr Asn Tyr Asn
    50                  55                  60

Pro Ser Leu Lys Ser Arg Val Thr Ile Ser Val Asp Thr Ser Lys Asn
65                  70                  75                  80

Gln Phe Ser Leu Lys Leu Ser Ser Val Thr Ala Ala Asp Thr Ala Val
                85                  90                  95

Tyr Tyr Cys Ala Arg Trp Asn Gly Val Asn Asn Ala Phe Asp Ile Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Val Ser Ala Ser Val Gly Asp Arg Val Thr Ile Thr Cys
145                 150                 155                 160

Arg Ala Ser Gln Gly Ile Ser Ser Trp Leu Ala Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Trp Gly Thr Glu Leu
        195                 200                 205

Thr Leu Thr Ile Ser Ser Leu Gln Pro Glu Asp Phe Ala Thr Tyr Tyr
    210                 215                 220

Cys Leu Gln His Asn Thr Tyr Pro Phe Thr Phe Gly Gln Gly Thr Lys
225                 230                 235                 240

Val Thr Val Leu Gly
                245

<210> SEQ ID NO 41
<211> LENGTH: 120
<212> TYPE: PRT
<213> ORGANISM: Homo sapiens

<400> SEQUENCE: 41

Met Ala Gln Val Gln Leu Leu Glu Ser Gly Pro Gly Leu Val Lys Pro
1               5                   10                  15

Ser Gln Thr Leu Ser Leu Thr Cys Thr Val Ser Gly Gly Ser Ile Ser
            20                  25                  30

Ser Gly Gly Tyr Tyr Trp Ser Trp Ile Arg Gln Pro Pro Gly Lys Gly
        35                  40                  45

Leu Glu Trp Ile Gly Tyr Ile Tyr Tyr Ser Gly Ser Thr Asn Tyr Asn
    50                  55                  60

Pro Ser Leu Lys Ser Arg Val Thr Ile Ser Val Asp Thr Ser Lys Asn
65                  70                  75                  80

Gln Phe Ser Leu Lys Leu Ser Ser Val Thr Ala Ala Asp Thr Ala Val
                85                  90                  95

Tyr Tyr Cys Ala Arg Trp Asn Gly Val Asn Asn Ala Phe Asp Ile Trp
            100                 105                 110

Gly Gln Gly Thr Leu Val Thr Val
            115             120

<210> SEQ ID NO 42
<211> LENGTH: 108
<212> TYPE: PRT
<213> ORGANISM: Homo sapiens

<400> SEQUENCE: 42

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Trp Gly Thr Glu Leu Thr Leu Thr Ile Ser Ser Leu Gln Pro
65                  70                  75                  80

Glu Asp Phe Ala Thr Tyr Tyr Cys Leu Gln His Asn Thr Tyr Pro Phe
                85                  90                  95

Thr Phe Gly Gln Gly Thr Lys Val Thr Val Leu Gly
            100                 105

<210> SEQ ID NO 43
<211> LENGTH: 10
<212> TYPE: PRT
<213> ORGANISM: Homo sapiens

<400> SEQUENCE: 43

Gly Gly Ser Ile Ser Ser Gly Gly Tyr Tyr
1               5                   10

<210> SEQ ID NO 44
<211> LENGTH: 7
<212> TYPE: PRT
<213> ORGANISM: Homo sapiens

<400> SEQUENCE: 44

Ile Tyr Tyr Ser Gly Ser Thr
1               5

<210> SEQ ID NO 45
<211> LENGTH: 13
<212> TYPE: PRT
<213> ORGANISM: Homo sapiens

<400> SEQUENCE: 45

Cys Ala Arg Trp Asn Gly Val Asn Asn Ala Phe Asp Ile
1               5                   10

<210> SEQ ID NO 46
<211> LENGTH: 6
<212> TYPE: PRT
<213> ORGANISM: Homo sapiens

<400> SEQUENCE: 46

Gln Gly Ile Ser Ser Trp
1               5

<210> SEQ ID NO 47
<211> LENGTH: 9

```
<212> TYPE: PRT
<213> ORGANISM: Homo sapiens

<400> SEQUENCE: 47

Leu Gln His Asn Thr Tyr Pro Phe Thr
1               5

<210> SEQ ID NO 48
<211> LENGTH: 247
<212> TYPE: PRT
<213> ORGANISM: Homo sapiens

<400> SEQUENCE: 48

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Thr Thr Tyr
            20                  25                  30

Gly Met Asn Trp Val Arg Gln Ala Pro Gly Lys Gly Leu Glu Trp Val
        35                  40                  45

Ser Tyr Ile Ser Ser Ser Ser Thr Ile Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Ser Ala Gly Asp Thr Ala Val Tyr Tyr Cys
                85                  90                  95

Ala Arg Gly Gly Asp Asn Ser Arg Gly Tyr Tyr Tyr Ile Ala Gly Gly
            100                 105                 110

Asp Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Glu Ile Val Leu
    130                 135                 140

Thr Gln Ser Pro Ala Ile Met Ser Ala Ser Pro Gly Glu Arg Val Thr
145                 150                 155                 160

Met Thr Cys Ser Ala Ser Ser Ile Arg Tyr Ile Tyr Trp Tyr Gln
                165                 170                 175

Gln Lys Pro Gly Ser Ser Pro Arg Leu Leu Ile Tyr Asp Thr Ser Asn
            180                 185                 190

Val Ala Pro Gly Val Pro Phe Arg Phe Ser Gly Ser Gly Ser Gly Thr
        195                 200                 205

Ser Tyr Ser Leu Thr Ile Asn Arg Met Glu Ala Glu Asp Ala Ala Thr
    210                 215                 220

Tyr Tyr Cys Gln Glu Trp Ser Gly Tyr Pro Tyr Thr Phe Gly Gly Gly
225                 230                 235                 240

Thr Lys Val Glu Ile Lys Arg
                245

<210> SEQ ID NO 49
<211> LENGTH: 124
<212> TYPE: PRT
<213> ORGANISM: Homo sapiens

<400> SEQUENCE: 49

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Thr Thr Tyr
            20                  25                  30

Gly Met Asn Trp Val Arg Gln Ala Pro Gly Lys Gly Leu Glu Trp Val
```

```
                35                  40                  45
Ser Tyr Ile Ser Ser Ser Ser Thr Ile Tyr Tyr Thr Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Ser Ala Gly Asp Thr Ala Val Tyr Tyr Cys
                 85                  90                  95
Ala Arg Gly Gly Asp Asn Ser Arg Gly Tyr Tyr Ile Ala Gly Gly
                100                 105                 110
Asp Tyr Trp Gly Gln Gly Thr Leu Val Thr Val Ser
            115                 120

<210> SEQ ID NO 50
<211> LENGTH: 107
<212> TYPE: PRT
<213> ORGANISM: Homo sapiens

<400> SEQUENCE: 50

Glu Ile Val Leu Thr Gln Ser Pro Ala Ile Met Ser Ala Ser Pro Gly
 1               5                  10                  15
Glu Arg Val Thr Met Thr Cys Ser Ala Ser Ser Ile Arg Tyr Ile
                 20                  25                  30
Tyr Trp Tyr Gln Gln Lys Pro Gly Ser Ser Pro Arg Leu Leu Ile Tyr
             35                  40                  45
Asp Thr Ser Asn Val Ala Pro Gly Val Pro Phe Arg Phe Ser Gly Ser
 50                  55                  60
Gly Ser Gly Thr Ser Tyr Ser Leu Thr Ile Asn Arg Met Glu Ala Glu
 65                  70                  75                  80
Asp Ala Ala Thr Tyr Tyr Cys Gln Glu Trp Ser Gly Tyr Pro Tyr Thr
                 85                  90                  95
Phe Gly Gly Gly Thr Lys Val Glu Ile Lys Arg
                100                 105

<210> SEQ ID NO 51
<211> LENGTH: 8
<212> TYPE: PRT
<213> ORGANISM: Homo sapiens

<400> SEQUENCE: 51

Gly Phe Ser Phe Thr Thr Tyr Gly
 1               5

<210> SEQ ID NO 52
<211> LENGTH: 7
<212> TYPE: PRT
<213> ORGANISM: Homo sapiens

<400> SEQUENCE: 52

Ile Ser Ser Ser Ser Ser Thr
 1               5

<210> SEQ ID NO 53
<211> LENGTH: 18
<212> TYPE: PRT
<213> ORGANISM: Homo sapiens

<400> SEQUENCE: 53

Ala Arg Gly Gly Asp Asn Ser Arg Gly Tyr Tyr Ile Ala Gly Gly
 1               5                  10                  15
```

Asp Tyr

<210> SEQ ID NO 54
<211> LENGTH: 5
<212> TYPE: PRT
<213> ORGANISM: Homo sapiens

<400> SEQUENCE: 54

Ser Ser Ile Arg Tyr
1               5

<210> SEQ ID NO 55
<211> LENGTH: 3
<212> TYPE: PRT
<213> ORGANISM: Homo sapiens

<400> SEQUENCE: 55

Asp Thr Ser
1

<210> SEQ ID NO 56
<211> LENGTH: 9
<212> TYPE: PRT
<213> ORGANISM: Homo sapiens

<400> SEQUENCE: 56

Gln Glu Trp Ser Gly Tyr Pro Tyr Thr
1               5

<210> SEQ ID NO 57
<211> LENGTH: 238
<212> TYPE: PRT
<213> ORGANISM: Homo sapiens

<400> SEQUENCE: 57

Gln Val Gln Leu Val Glu Thr Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Val Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Pro Ser Tyr Gly Asp Tyr Phe Arg Trp Phe Asp Pro
            100                 105                 110

Trp Gly Gln Gly Thr Leu Val Thr Val Ser Ser Gly Gly Gly Gly
        115                 120                 125

Ser Glu Ile Val Leu Thr Gln Ser Pro Gly Thr Leu Ser Leu Ser Pro
    130                 135                 140

Gly Glu Thr Ala Thr Leu Ser Cys Arg Ala Ser His Ala Val Ser Ser
145                 150                 155                 160

Asn Ser Leu Ala Trp Tyr Gln Gln Arg Pro Gly Gln Thr Pro Arg Leu
                165                 170                 175

Leu Ile Tyr Gly Ala Ser Ser Arg Ala Thr Gly Ile Pro Asp Arg Phe
            180                 185                 190

-continued

```
Ser Gly Ser Gly Ser Gly Thr Asp Phe Thr Leu Thr Ile Ser Arg Leu
            195                 200                 205

Glu Pro Glu Asp Phe Ala Val Tyr Tyr Cys Gln Gln Tyr Gly Ser Ser
        210                 215                 220

Pro Pro Ile Thr Phe Gly Gln Gly Pro Ser Trp Arg Ser Asn
225                 230                 235

<210> SEQ ID NO 58
<211> LENGTH: 124
<212> TYPE: PRT
<213> ORGANISM: Homo sapiens

<400> SEQUENCE: 58

Gln Val Gln Leu Val Glu Thr Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Val Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Pro Ser Tyr Gly Asp Tyr Phe Arg Trp Phe Asp Pro
            100                 105                 110

Trp Gly Gln Gly Thr Leu Val Thr Val Ser Ser Ser
        115                 120

<210> SEQ ID NO 59
<211> LENGTH: 109
<212> TYPE: PRT
<213> ORGANISM: Homo sapiens

<400> SEQUENCE: 59

Glu Ile Val Leu Thr Gln Ser Pro Gly Thr Leu Ser Leu Ser Pro Gly
1               5                   10                  15

Glu Thr Ala Thr Leu Ser Cys Arg Ala Ser His Ala Val Ser Ser Asn
            20                  25                  30

Ser Leu Ala Trp Tyr Gln Gln Arg Pro Gly Gln Thr Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Ile Thr Phe Gly Gln Gly Pro Ser Trp Arg Ser Asn
            100                 105

<210> SEQ ID NO 60
<211> LENGTH: 8
<212> TYPE: PRT
<213> ORGANISM: Homo sapiens

<400> SEQUENCE: 60

Gly Tyr Thr Phe Thr Gly Tyr Tyr
```

```
-continued
```

```
<210> SEQ ID NO 61
<211> LENGTH: 8
<212> TYPE: PRT
<213> ORGANISM: Homo sapiens

<400> SEQUENCE: 61

Ile Asn Pro Asn Ser Gly Gly Thr
1               5

<210> SEQ ID NO 62
<211> LENGTH: 16
<212> TYPE: PRT
<213> ORGANISM: Homo sapiens

<400> SEQUENCE: 62

Ala Arg Gly Gly Pro Ser Tyr Gly Asp Tyr Phe Arg Trp Phe Asp Pro
1               5                   10                  15

<210> SEQ ID NO 63
<211> LENGTH: 7
<212> TYPE: PRT
<213> ORGANISM: Homo sapiens

<400> SEQUENCE: 63

His Ala Val Ser Ser Asn Ser
1               5

<210> SEQ ID NO 64
<211> LENGTH: 3
<212> TYPE: PRT
<213> ORGANISM: Homo sapiens

<400> SEQUENCE: 64

Gly Ala Ser
1

<210> SEQ ID NO 65
<211> LENGTH: 10
<212> TYPE: PRT
<213> ORGANISM: Homo sapiens

<400> SEQUENCE: 65

Gln Gln Tyr Gly Ser Ser Pro Pro Ile Thr
1               5                   10

<210> SEQ ID NO 66
<211> LENGTH: 244
<212> TYPE: PRT
<213> ORGANISM: Homo sapiens

<400> SEQUENCE: 66

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Glu Val Ala Ala Ala Gly Ile Asn Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Glu Thr Thr Leu Thr Gln Ser
130                 135                 140

Pro Ala Ile Met Ser Ala Ser Pro Gly Glu Arg Val Thr Met Thr Cys
145                 150                 155                 160

Ser Ala Ser Ser Ser Ile Arg Tyr Ile Tyr Trp Tyr Gln Gln Lys Pro
                165                 170                 175

Gly Ser Ser Pro Arg Leu Leu Ile Tyr Asp Thr Ser Asn Val Ala Pro
            180                 185                 190

Gly Val Pro Phe Arg Phe Ser Gly Ser Gly Ser Gly Thr Ser Tyr Ser
        195                 200                 205

Leu Thr Ile Asn Arg Met Glu Ala Glu Asp Ala Ala Thr Tyr Tyr Cys
        210                 215                 220

Gln Glu Trp Ser Gly Tyr Pro Tyr Thr Phe Gly Gly Gly Thr Lys Val
225                 230                 235                 240

Asp Ile Lys Arg

<210> SEQ ID NO 67
<211> LENGTH: 122
<212> TYPE: PRT
<213> ORGANISM: Homo sapiens

<400> SEQUENCE: 67

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Val Ala Ala Ala Gly Ile Asn Asp Ala Phe Asp Ile Trp
            100                 105                 110

Gly Gln Gly Thr Met Val Thr Val Ser Ser
        115                 120

<210> SEQ ID NO 68
<211> LENGTH: 107
<212> TYPE: PRT
<213> ORGANISM: Homo sapiens

<400> SEQUENCE: 68

Glu Thr Thr Leu Thr Gln Ser Pro Ala Ile Met Ser Ala Ser Pro Gly
1               5                   10                  15

Glu Arg Val Thr Met Thr Cys Ser Ala Ser Ser Ser Ile Arg Tyr Ile
            20                  25                  30
```

```
Tyr Trp Tyr Gln Gln Lys Pro Gly Ser Ser Pro Arg Leu Leu Ile Tyr
                 35                  40                  45

Asp Thr Ser Asn Val Ala Pro Gly Val Pro Phe Arg Phe Ser Gly Ser
 50                  55                  60

Gly Ser Gly Thr Ser Tyr Ser Leu Thr Ile Asn Arg Met Glu Ala Glu
 65                  70                  75                  80

Asp Ala Ala Thr Tyr Tyr Cys Gln Glu Trp Ser Gly Tyr Pro Tyr Thr
                 85                  90                  95

Phe Gly Gly Gly Thr Lys Val Asp Ile Lys Arg
             100                 105

<210> SEQ ID NO 69
<211> LENGTH: 8
<212> TYPE: PRT
<213> ORGANISM: Homo sapiens

<400> SEQUENCE: 69

Gly Phe Thr Phe Ser Ser Tyr Glu
 1               5

<210> SEQ ID NO 70
<211> LENGTH: 7
<212> TYPE: PRT
<213> ORGANISM: Homo sapiens

<400> SEQUENCE: 70

Ile Ser Ser Ser Gly Ser Thr
 1               5

<210> SEQ ID NO 71
<211> LENGTH: 15
<212> TYPE: PRT
<213> ORGANISM: Homo sapiens

<400> SEQUENCE: 71

Ala Arg Glu Val Ala Ala Ala Gly Ile Asn Asp Ala Phe Asp Ile
 1               5                  10                  15

<210> SEQ ID NO 72
<211> LENGTH: 5
<212> TYPE: PRT
<213> ORGANISM: Homo sapiens

<400> SEQUENCE: 72

Ser Ser Ile Arg Tyr
 1               5

<210> SEQ ID NO 73
<211> LENGTH: 3
<212> TYPE: DNA
<213> ORGANISM: Homo sapiens

<400> SEQUENCE: 73 dts                                                                        3

<210> SEQ ID NO 74
<211> LENGTH: 9
<212> TYPE: PRT
<213> ORGANISM: Homo sapiens

<400> SEQUENCE: 74

Gln Glu Trp Ser Gly Tyr Pro Tyr Thr
 1               5
```

<210> SEQ ID NO 75
<211> LENGTH: 232
<212> TYPE: PRT
<213> ORGANISM: Homo sapiens

<400> SEQUENCE: 75

```
Gln Val Gln Leu Gln Gln Ser Gly Thr Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Asp Ile Asn Trp Val Arg Gln Thr Pro Glu Gln Gly Leu Glu Trp Ile
        35                  40                  45

Gly Trp Ile Phe Pro Gly Glu Gly Ser Thr Glu Tyr Asn Glu Lys Phe
    50                  55                  60

Lys Gly Arg Ala Thr Leu Ser Val Asp Lys Ser Ser Ser Thr Ala Tyr
65                  70                  75                  80

Met Glu Leu Thr Arg Leu Thr Ser Glu Asp Ser Ala Val Tyr Phe Cys
                85                  90                  95

Ala Arg Gly Asp Tyr Tyr Arg Arg Tyr Phe Asp Leu Trp Gly Gln Gly
            100                 105                 110

Thr Leu Val Thr Val Ser Ser Arg Gly Gly Gly Ser Glu Thr Thr
        115                 120                 125

Leu Thr Gln Ser Pro Ala Phe Lys Ser Ala Thr Pro Gly Asp Lys Val
    130                 135                 140

Thr Ile Ser Cys Lys Ala Ser Gln Asp Ile Asp Asp Met Asn Trp
145                 150                 155                 160

Gln His Lys Pro Gly Ala Ala Ala Ile Phe Thr Thr Gln Glu Pro Thr
                165                 170                 175

Pro Leu Val Pro Gly Ile Pro Pro Arg Phe Ser Gly Ser Gly Ser Gly
            180                 185                 190

Thr Asn Phe Thr Leu Thr Ile Ile Asn Ile Glu Ser Glu Asp Ala Pro
        195                 200                 205

Tyr Tyr Phe Cys Leu Gln His Gly Asp Phe Leu Thr Trp Thr Phe Gly
    210                 215                 220

Gln Gly Thr Lys Val Asp Ile Lys
225                 230
```

<210> SEQ ID NO 76
<211> LENGTH: 120
<212> TYPE: PRT
<213> ORGANISM: Homo sapiens

<400> SEQUENCE: 76

```
Gln Val Gln Leu Gln Gln Ser Gly Thr Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Asp Ile Asn Trp Val Arg Gln Thr Pro Glu Gln Gly Leu Glu Trp Ile
        35                  40                  45

Gly Trp Ile Phe Pro Gly Glu Gly Ser Thr Glu Tyr Asn Glu Lys Phe
    50                  55                  60

Lys Gly Arg Ala Thr Leu Ser Val Asp Lys Ser Ser Ser Thr Ala Tyr
65                  70                  75                  80

Met Glu Leu Thr Arg Leu Thr Ser Glu Asp Ser Ala Val Tyr Phe Cys
                85                  90                  95
```

Ala Arg Gly Asp Tyr Tyr Arg Arg Tyr Phe Asp Leu Trp Gly Gln Gly
            100                 105                 110

Thr Leu Val Thr Val Ser Ser Arg
        115                 120

<210> SEQ ID NO 77
<211> LENGTH: 107
<212> TYPE: PRT
<213> ORGANISM: Homo sapiens

<400> SEQUENCE: 77

Glu Thr Thr Leu Thr Gln Ser Pro Ala Phe Lys Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Gln His Lys Pro Gly Ala Ala Ile Phe Thr Thr Gln
        35                  40                  45

Glu Pro Thr Pro Leu Val Pro Gly Ile Pro Pro Arg Phe Ser Gly Ser
    50                  55                  60

Gly Ser Gly Thr Asn Phe Thr Leu Thr Ile Ile Asn Ile Glu Ser Glu
65                  70                  75                  80

Asp Ala Pro Tyr Tyr Phe Cys Leu Gln His Gly Asp Phe Leu Thr Trp
                85                  90                  95

Thr Phe Gly Gln Gly Thr Lys Val Asp Ile Lys
            100                 105

<210> SEQ ID NO 78
<211> LENGTH: 8
<212> TYPE: PRT
<213> ORGANISM: Homo sapiens

<400> SEQUENCE: 78

Gly Tyr Ile Phe Thr Ser Tyr Asp
1               5

<210> SEQ ID NO 79
<211> LENGTH: 8
<212> TYPE: PRT
<213> ORGANISM: Homo sapiens

<400> SEQUENCE: 79

Ile Phe Pro Gly Glu Gly Ser Thr
1               5

<210> SEQ ID NO 80
<211> LENGTH: 12
<212> TYPE: PRT
<213> ORGANISM: Homo sapiens

<400> SEQUENCE: 80

Ala Arg Gly Asp Tyr Tyr Arg Arg Tyr Phe Asp Leu
1               5                   10

<210> SEQ ID NO 81
<211> LENGTH: 6
<212> TYPE: PRT
<213> ORGANISM: Homo sapiens

<400> SEQUENCE: 81

Gln Asp Ile Asp Asp Asp
1               5

```
<210> SEQ ID NO 82
<211> LENGTH: 3
<212> TYPE: PRT
<213> ORGANISM: Homo sapiens

<400> SEQUENCE: 82

Glu Pro Thr
1

<210> SEQ ID NO 83
<211> LENGTH: 10
<212> TYPE: PRT
<213> ORGANISM: Homo sapiens

<400> SEQUENCE: 83

Leu Gln His Gly Asp Phe Leu Thr Trp Thr
1               5                   10
```

METHODS AND COMPOSITIONS RELATED TO MODULATORS OF EUKARYOTIC CELLS

CROSS-REFERENCE TO RELATED APPLICATIONS

The subject patent application claims the benefit of priority to U.S. Provisional Patent Application Nos. 61/695,527 (filed Aug. 31, 2012) and 61/814,646 (filed Apr. 22, 2013). The full disclosures of the priority applications are incorporated herein by reference in their entireties and for all purposes.

BACKGROUND OF THE INVENTION

Functional antibodies are an important therapeutic option for treatment of a wide variety of diseases. Currently, the field of immunochemistry has turned its attention to more challenging goals such as the generation of broadly neutralizing antiviral antibodies where a useful molecule may be very rare. This frequency problem has been largely solved by the advent of combinatorial antibody libraries where today one can select from a repertoire that contains as many as $10^{11}$ different members. As an example, the power of this approach has been demonstrated in the study of influenza viruses where the selection of rare antibodies has led to the discovery of new modes of virus neutralization thereby offering previously unrealized possibilities for therapy and even the generation of a universal vaccine.

However, even with a solution to the frequency problem, isolation of an antibody whose function goes beyond simple binding is still a painstaking process. There is a need in the art for better means for identifying functional antibodies from pools of candidate molecules. The present invention is directed to this and other needs.

SUMMARY OF THE INVENTION

In one aspect, the invention provides methods for identifying modulatory protein agents (e.g., antibodies or other polypeptides) that regulate phenotypes of eukaryotic cells. The methods entail first expressing in a population of cells of a eukaryotic cell type a library of candidate agents (e.g., antibodies or antigen-binding fragments thereof). This will produce a heterogeneous population of modified cells expressing the candidate agents. Preferably, the library of candidate agents is introduced into and expressed in the starting homogeneous population of cells under conditions each cell expresses no more than 3 different members of the library of candidate agents. In some of these preferred embodiments, each cell expresses just one species of the introduced exogenous agent. This is followed by selecting at least one specific agent-expressing cell with an altered phenotype relative to that of an unmodified control cell of the same eukaryotic cell type. This allows identification of the specific candidate agent (e.g., agonist antibody) expressed in the specific agent-expressing cell as a modulator of the eukaryotic cell type.

Typically, the library of candidate agents is a combinatorial library of secreted polypeptides or peptides (e.g., secreted antibodies or intrabodies). In some embodiments, the combinatorial agent library is an antibody library expressed in the cell via a lentiviral vector or a retroviral vector. In some preferred embodiments, the cell type employed in the methods is a mammalian cell type. In some methods of the invention, the cells for which modulatory antibodies are to be identified are cultured in a diffusion restricting medium during selection. Some methods of the invention further include isolating a polynucleotide sequence encoding the specific candidate antibody and determining nucleotide and amino acid sequences of heavy chain and light chain variable regions of the identified candidate antibody.

In some embodiments, the phenotype to be modulated or regulated is a cellular response or signaling activity of the cells. In some embodiments, the eukaryotic cell type is a stem cell type, and the phenotype is differentiation of the stem cell. In some methods of the invention, the phenotype to be modulated is mediated via a target molecule. In some embodiments, the target molecule is encoded by a tumor suppressor gene or an oncogene. In some other embodiments, the target molecule is a secreted hormone or cytokine, e.g., erythropoietin, thrombopoietin or IL-1. In some embodiments, the target molecule is a signaling receptor of the cell. For example, it can be a receptor for a secreted hormone or cytokine. Some embodiments of the invention are directed to identifying phenotype modulators that are heterodimeric bispecific antibodies. In some embodiments, the identified bispecific antibody binds to two different epitopes on a target molecule.

In some embodiments, the identified modulator antibody agonizes the target molecule. In some other embodiments, the identified modulator antibody antagonizes the target molecule or antagonizes an inhibitor of the target molecule. In some of the latter embodiments, the selection can be performed in the presence of the inhibitor. In some embodiments, the selection can further comprise screening the library of candidate antibodies to identify binders of the target molecule prior to expressing the binder antibodies in the cells for phenotypic selection. For example, the binder antibodies of the target molecule can be identified via phage display. In some other methods of the invention, the phenotype to be modulated is expression of a target molecule or marker gene in the eukaryotic cell type. For example, the identified antibody modulator can regulate expression of a cell surface receptor.

In a related aspect, the invention provides methods for identifying antibodies that modulate a phenotype of a eukaryotic cell. These methods involve (a) expressing in a homogeneous population of cells of a second cell type a library of candidate antibodies or antigen-binding fragments thereof under conditions each cell expresses no more than 3 different antibody species to produce a heterogeneous population of antibody-expressing cells, (b) co-culturing a population of cells of said eukaryotic cell type and the population of antibody-expressing cells, and (c) selecting a specific antibody-expressing cell that alters a phenotype of the eukaryotic cell type. This leads to identification of a candidate antibody expressed in the specific antibody-expressing cell as a modulator of the eukaryotic cell type. In some embodiments, only one different member of the antibody library is expressed in each cell of the population of antibody-expressing cells.

Some of these methods are directed to identifying antibody modulators of a diseased mammalian cell. For example, the methods can be used for selecting antibody that modulate certain phenotypes of tumor cells, e.g., stopped or slowed growth of a tumor cell. In some embodiments, the phenotype is mediated via a target molecule. In some of these embodiments, the identified candidate antibody is an antagonist of the target molecule.

In another aspect, the invention provides methods for identifying protein or polypeptide agents (antibodies, polypeptides or peptides) which are capable of reprograming or trans-differentiating a target cell along a desired pathway. These methods involve (1) expressing a library of candidate polypeptide agents in a reporter cell bearing a signaling receptor expressed by the target cell, thereby producing a heterogeneous population of modified, agent-expressing reporter cells, (2) identifying from the heterogeneous population of cells a subpopulation of agent-expressing reporter cells having activated signaling of the receptor, (3) isolating a group of agonist agents from the identified subpopulation of cells, and (4) contacting the group of agonist agents with a population of the target cell and selecting a cell with a specific phenotype indicative of trans-differentiation.

Some of these methods are directed to reprograming target cells that are somatic cells or lineage restricted stem cells. Some methods are specifically directed to identifying agonist antibodies or antigen-binding fragments for reprograming a target cell. In some methods, the candidate agents and the receptor are co-integrated into the plasma membranes of the reporter cells. In various embodiments, the receptor to be co-expressed in the reporter cell is one that normally promotes the specific phenotype in the target cell. In some methods, the receptor used for identifying agonist agents is G-CSFR, and the specific phenotype evidencing trans-differentiation of the target cell is neurogenesis.

In another aspect, the invention provide antibodies or antigen-binding fragment thereof which bind to human erythropoietin receptor. These antibodies have the same binding specificity as that of an antibody comprising (1) heavy chain CDR1, CDR2 and CDR3 sequences respectively shown in SEQ ID NO:1, SEQ ID NO:2 and SEQ ID NO:3; and light chain CDR1, CDR2 and CDR3 sequences respectively shown in SEQ ID NO:4, SEQ ID NO:5 and SEQ ID NO:6; (2) heavy chain CDR1, CDR2 and CDR3 sequences respectively shown in SEQ ID NO:9, SEQ ID NO:10 and SEQ ID NO:11; and light chain CDR1, CDR2 and CDR3 sequences respectively shown in SEQ ID NO:12, SEQ ID NO:13 and SEQ ID NO:14; or (3) heavy chain CDR1, CDR2 and CDR3 sequences respectively shown in SEQ ID NO:15, SEQ ID NO:16 and SEQ ID NO:17; and light chain CDR1, CDR2 and CDR3 sequences respectively shown in SEQ ID NO:18, SEQ ID NO:19 and SEQ ID NO:20. In some embodiments, the antibody or antigen-binding fragment thereof have heavy chain CDR1, CDR2 and CDR3 sequences that are substantially identical to SEQ ID NO:1, SEQ ID NO:2 and SEQ ID NO:3, respectively; and light chain CDR1, CDR2 and CDR3 sequences that are substantially identical to SEQ ID NO:4, SEQ ID NO:5 and SEQ ID NO:6, respectively. Some antibodies of the invention have heavy chain CDR1, CDR2 and CDR3 sequences that are respectively identical to SEQ ID NO:1, SEQ ID NO:2 and SEQ ID NO:3; and light chain CDR1, CDR2 and CDR3 sequences that are respectively identical to SEQ ID NO:4, SEQ ID NO:5 and SEQ ID NO:6. Some antibodies of the invention have heavy chain and light chain variable region sequences show in SEQ ID NO:7 and SEQ ID NO:8, respectively.

Some other embodiments of the invention are directed to specific anti-TpoR agonist antibodies, anti-G-CSFR agonist antibodies or stem cell differentiation inducing antibodies described herein. Some of these antibodies have the same binding specificity as that of an antibody comprising (1) heavy chain CDR1, CDR2 and CDR3 sequences respectively shown in SEQ ID NO:35, SEQ ID NO:36 and SEQ ID NO:37; and light chain CDR1, CDR2 and CDR3 sequences respectively shown in SEQ ID NO:38, SEQ ID NO:13 and SEQ ID NO:39; (2) heavy chain CDR1, CDR2 and CDR3 sequences respectively shown in SEQ ID NO:43, SEQ ID NO:44 and SEQ ID NO:45; and light chain CDR1, CDR2 and CDR3 sequences respectively shown in SEQ ID NO:46, SEQ ID NO:13 and SEQ ID NO:47; (3) heavy chain CDR1, CDR2 and CDR3 sequences respectively shown in SEQ ID NO:51, SEQ ID NO:52 and SEQ ID NO:53; and light chain CDR1, CDR2 and CDR3 sequences respectively shown in SEQ ID NO:54, SEQ ID NO:55 and SEQ ID NO:56; or (4) heavy chain CDR1, CDR2 and CDR3 sequences respectively shown in SEQ ID NO:60, SEQ ID NO:61 and SEQ ID NO:62; and light chain CDR1, CDR2 and CDR3 sequences respectively shown in SEQ ID NO:63, SEQ ID NO:64 and SEQ ID NO:65.

Some of these antibodies of the invention have (1) heavy chain CDR1, CDR2 and CDR3 sequences that are the same as or substantially identical to SEQ ID NO:35, SEQ ID NO:36 and SEQ ID NO:37, respectively; and light chain CDR1, CDR2 and CDR3 sequences that are the same as or substantially identical to SEQ ID NO:38, SEQ ID NO:13 and SEQ ID NO:39, respectively; (2) heavy chain CDR1, CDR2 and CDR3 sequences that are the same as or substantially identical to SEQ ID NO:43, SEQ ID NO:44 and SEQ ID NO:45, respectively; and light chain CDR1, CDR2 and CDR3 sequences that are the same as or substantially identical to SEQ ID NO:46, SEQ ID NO:13 and SEQ ID NO:47, respectively; (3) heavy chain CDR1, CDR2 and CDR3 sequences that are the same as or substantially identical to SEQ ID NO:51, SEQ ID NO:52 and SEQ ID NO:53, respectively; and light chain CDR1, CDR2 and CDR3 sequences that are the same as or substantially identical to SEQ ID NO:54, SEQ ID NO:55 and SEQ ID NO:56, respectively; or (4) heavy chain CDR1, CDR2 and CDR3 sequences that are the same as or substantially identical to SEQ ID NO:61, SEQ ID NO:62 and SEQ ID NO:63, respectively; and light chain CDR1, CDR2 and CDR3 sequences that are the same as or substantially identical to SEQ ID NO:64, SEQ ID NO:65 and SEQ ID NO:66, respectively. Some of the antibodies have heavy chain and light chain variable region sequences show in (1) SEQ ID NO:33 and SEQ ID NO:34, respectively; (2) SEQ ID NO:41 and SEQ ID NO:42, respectively; (3) SEQ ID NO:49 and SEQ ID NO:50, respectively; or (4) SEQ ID NO:58 and SEQ ID NO:59, respectively.

In various embodiments, the receptor agonist antibodies of the invention are scFv antibody fragments. Some of these antibodies contain a scFv antibody fragment fused to Fc portion of human IgG1. In some related embodiments, the invention provides isolated or recombinant polynucleotides encoding the variable region of the heavy chain or light chain of the receptor agonist antibodies disclosed herein.

In another aspect, the invention provides heterodimeric bispecific antibodies or antigen binding fragments thereof that bind to human erythropoietin receptor or human integrin α3 chain. These bispecific antibodies have (1) a first monomer comprising HCDR1, HCDR2, HCDR3, LCDR1, LCDR2 and LCDR3 sequences that are substantially identical to SEQ ID NOs:9-14, respectively, and a second monomer comprising HCDR1, HCDR2, HCDR3, LCDR1, LCDR2 and LCDR3 sequences that are substantially identical to SEQ ID NOs:15-20, respectively; or (2) a first monomer comprising HCDR1, HCDR2, HCDR3, LCDR1, LCDR2 and LCDR3 sequences that are substantially identical to SEQ ID NOs:69-74, respectively, and a second monomer comprising HCDR1, HCDR2, HCDR3, LCDR1, LCDR2 and LCDR3 sequences that are substantially identical to SEQ ID NOs:78-83, respectively.

Some of these antibodies binds to human EpoR, and have a first monomer comprising HCDR1, HCDR2, HCDR3, LCDR1, LCDR2 and LCDR3 sequences that are the same as or substantially identical to SEQ ID NOs:9-14, respectively, and a second monomer comprising HCDR1, HCDR2, HCDR3, LCDR1, LCDR2 and LCDR3 sequences that are the same as or substantially identical to SEQ ID NOs:15-20, respectively. Some of these anti-EpoR bispecific antibodies of the invention have a first monomer comprising heavy chain and light chain variable region sequences shown in SEQ ID NO:21 and SEQ ID NO:22, respectively, and (2) a second monomer comprising heavy chain and light chain variable region sequences shown in SEQ ID NO:23 and SEQ ID NO:24, respectively.

Some of the bispecific antibodies of the invention bind to human integrin α3 chain, and have a first monomer comprising HCDR1, HCDR2, HCDR3, LCDR1, LCDR2 and LCDR3 sequences that are the same as or substantially identical to SEQ ID NOs:69-74, respectively, and a second monomer comprising HCDR1, HCDR2, HCDR3, LCDR1, LCDR2 and LCDR3 sequences that are the same as or substantially identical to SEQ ID NOs:78-83, respectively. Some of these anti-integrin α3 chain bispecific antibodies have a first monomer comprising heavy chain and light chain variable region sequences shown in SEQ ID NO:67 and SEQ ID NO:68, respectively, and (2) a second monomer comprising heavy chain and light chain variable region sequences shown in SEQ ID NO:76 and SEQ ID NO:77, respectively.

In some embodiments, each monomer of the bispecific antibody is a scFv antibody fragment, and the variable region sequence of each of the monomers is fused to Fc portion of human IgG1. In some related embodiments, the invention provides isolated or recombinant polynucleotide sequences that encode the variable region of the heavy chain or light chain of the first monomer or the second monomer of the bispecific antibodies disclosed herein.

A further understanding of the nature and advantages of the present invention may be realized by reference to the remaining portions of the specification and claims.

DETAILED DESCRIPTION OF THE INVENTION

I. Overview

The invention is predicated in part on the development by the present inventors a method that uses combinatorial antibody libraries to endow cells with new binding energy landscapes for the purpose of regulating their phenotypes. As detailed in the Examples below, the method employs large combinatorial antibody libraries expressed inside cells which allow for direct selection of potent phenocopies of agonists. Specifically, antibodies expressed in cells were selected directly for function (i.e., an altered phenotype of the cells expressing the antibodies) rather than simple binding. To ensure easy association of a modulated phenotype with a specific antibody species, the antibody library is introduced into and expressed in the cells under conditions that will allow each cell to express no more than about 2 or 3 different antibody species. This can be accomplished by introducing members of the antibody library into the cells via a lentiviral based vector system exemplified herein. In some embodiments, the cells are infected with the antibody-encoding viruses at a low multiplicity of infection (MOI), e.g., less than one. Under such conditions, each individual cell will likely express just one different member of the antibody library. Antibodies selected in these embodiments typically are homodimeric molecules. In some other embodiments, additional diversity of the antibody library beyond the initial combinatorial diversity once introduced into the cells is desired, e.g., for generating heterodimeric bispecific antibodies as exemplified herein. This can be achieved via infecting the antibody-encoding viruses at a slightly higher MOI (e.g., at around 2 or 3) because more than one lentivirus can infect a single cell. In the case of scFv antibody libraries, re-assortment of the different Fv domains of the antibody molecules themselves inside cells leads to additional diversity.

The advantage of the methods of the invention derives partially from selection rather than screening. The selection scheme disclosed herein enables direct correlation of an altered phenotype with a specific antibody modulator or ligand (e.g., EpoR antibody or TpoR antibody). Such an effect is difficult to achieve by screening only for binding or by design. This is also unlike some conventional high throughput screening schemes that different pooled antibody-encoding sequences are transfected into same host cells for functional analysis (see, e.g., U.S. Pat. No. 7,884,054). Once positive clones are identified in such screening schemes, isolation of antibody sequences and additional testing are required to identify a specific molecule that is responsible for an observed phenotype.

Figure 6:
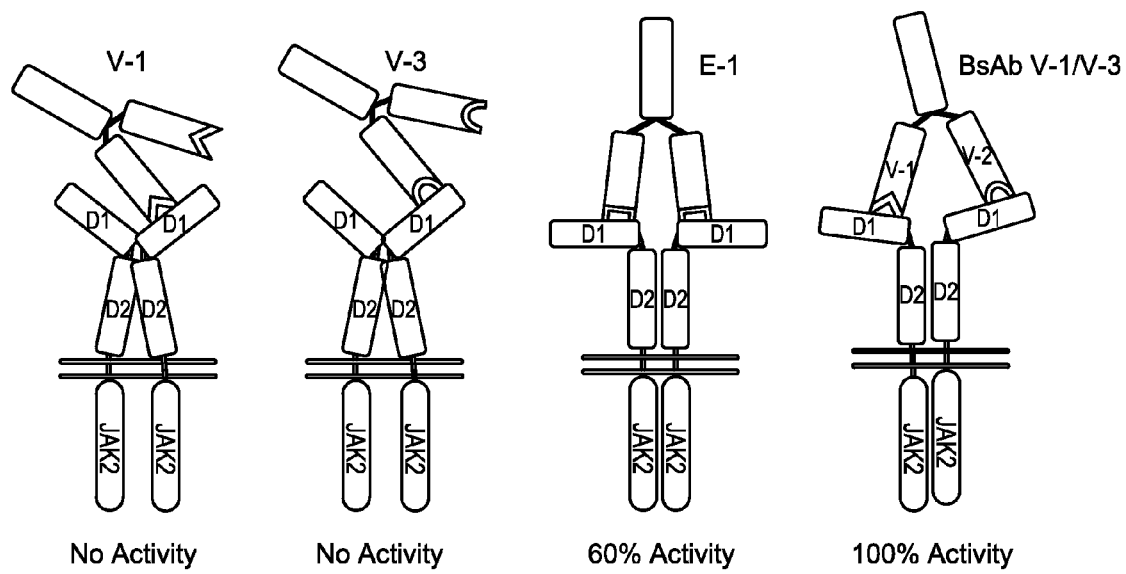
FIG. 6 shows potential mechanisms of activation of EpoR by agonist antibodies. Potent agonist activity is likely to be associated with asymmetric binding of the heterodimeric bispecific antibodies as for EPO. Asymmetric binding reorients the D1 and D2 ectodomains for optimal signaling via the JAK2/Stat5 pathway. A homodimeric antibody (E-1) is only a partial agonist, suggesting a more symmetric interaction with less activation as for a peptide agonist (Livnah et al., Science 273: 464, 1996). Antibodies that bind EpoR, but don't activate, likely bind to only one arm of the EpoR unliganded dimer in an orientation that precludes bivalent association of the antibody.

The advantage of the selection methods of the invention is also demonstrated by an ability to select very unusual antibodies (e.g., bispecific EpoR antibodies or trans-differentiating G-CSFR antibodies). Some of these rare antibodies are potent full erythropoietin agonists whose ontogeny depends on the recombination at the protein level of pairs of antibodies expressed in the same cell to generate heterodimeric bispecific antibodies. The obligate synergy between the different binding specificities of the antibody's monomeric subunits appears to replicate the asymmetric binding mechanism of authentic erythropoietin (Epo). As exemplification, the bispecific EpoR antibody selected herein has full agonist activity and appears to require cooperatively of two different binding specificities whose agonist mechanism is similar to the asymmetric interaction of EPO with the EpoR. Thus, the fact that antibodies with both specificities can bind to the EpoR but they are only agonists when they are combined in the same molecule suggests that their function goes beyond simple dimerization of the EpoR or differ from other dimer configurations generated by partial agonists, antagonists, antagonists, or unliganded dimers (FIG. 6).

The selection system described herein can reveal a myriad of effects as a consequence of the perturbation of cellular phenotypes by expression of new protein binding energies inside cells. As demonstrated in the Examples below, the methods of the invention allow identification of both homodimeric mono-specific antibody agonists and heterodimeric bispecific antibody modulators of cellular phenotypes and signaling cascades. In some preferred embodiments, the viruses employed in constructing the antibody library are vesicular stomatitis virus/lentivirus pseudotypes. These viruses have a broad host range and, thus, can be used in a wide variety of cells. While exemplified with antibodies, the application also encompasses direct phenotypic selection of libraries of other polypeptides each with different binding potential upon expression inside a population of cells.

In related embodiments, the invention demonstrated that the selection scheme can allow one to identify protein agonists which are capable of reprograming a differentiated target cell or lineage-restricted stem cell. Exemplified herein is selection for antibody agonists of G-CSFR which can trans-differentiate human myloid lineage CD34+ stem cells into neural progenitor cells. Specifically, antibodies that are agonists for the granulocyte colony stimulating factor receptor were selected from intracellular libraries on the basis of their ability to activate signaling pathways in reporter cells. With a specialized "near neighbor" approach, the entire antibody library and its target receptor are co-integrated into the plasma membranes of a population of reporter cells. This format favors unusual interactions between receptors and their protein ligands and ensures that the antibody acts in an autocrine manner on the cells that produce it. As a result, it was found that, unlike the natural granulocyte-colony stimulating factor that activates cells to differentiate along a predetermined pathway, some isolated agonist antibodies trans-differentiated human myeloid lineage CD-34+ bone marrow cells into neural progenitors. This trans-differentiation by agonist antibodies is different from more commonly used methods because initiation is agenetic. Antibodies that act at the plasma membrane may have therapeutic potential as agents that trans-differentiate autologous cells.

As exemplified herein, one powerful format utilizes positive selection because it lends itself to easy recovery of the functioning antibodies. However, a slight change in the format also allows for negative selection of events such as cell death that could be important for finding new targets for cancer therapy. In some of these embodiments, one can use co-cultivations of differentially labeled feeder cells that produce the antibodies ("producer cell") and target cells ("indicator cell") followed by selection for colonies or plaques where only feeder cells are present because the target cells have been killed. In some embodiments, an antibody library not preselected on any target can be used to isolate antibody agonists that act indirectly by perturbation of regulatory molecules. For example, this can be useful for selecting antibodies that regulate the differentiation of stem cells, identifying tumor suppressor gene products, or for generating therapeutic agonists not otherwise available (e.g., a thrombopoietin phenocopy). Exemplified herein include selection of agonist antibody agonist for thrombopoietin, selection of antibody modulators of stem cell differentiation based on morphogenic phenotype, and selection of granulocyte colony stimulating factor (GCSF) agonist antibodies based on autocrine signaling. Finally, the method of the invention may be useful in identifying new therapeutic targets, even when they are not addressable by antibodies. Thus, when molecules that are exclusively intracellular are identified, they can be novel targets for small molecule therapeutics. This may be especially important in cancer where targets may be exclusive to certain types of cancer or even tumors isolated from individual patients.

Some of the antibodies exemplified herein are useful immunochemical reagents with novel functional and structural properties (e.g., the EpoR bispecific antibody or the trans-differentiating G-CSFR antibody). For example, the selection methods of the invention was powerful enough to identify potent bispecific heterodimeric Epo-agonist antibodies that replicate the complicated asymmetric binding mechanism used in the natural cytokine receptor signaling pathway.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (Oxford Paperback Reference), Martin and Hine (Eds.), Oxford University Press ($4^{th}$ ed., 2000). In addition, the following definitions are provided to assist the reader in the practice of the invention.

The term "antibody" or "antigen-binding fragment" refers to polypeptide chain(s) which exhibit a strong monovalent, bivalent or polyvalent binding to a given antigen, epitope or epitopes. Unless otherwise noted, antibodies or antigen-binding fragments used in the invention can have sequences derived from any vertebrate, camelid, avian or pisces species. They can be generated using any suitable technology, e.g., hybridoma technology, ribosome display, phage display, gene shuffling libraries, semi-synthetic or fully synthetic libraries or combinations thereof. Unless otherwise noted, the term "antibody" as used in the present invention includes intact antibodies, antigen-binding polypeptide fragments and other designer antibodies that are described below or well known in the art (see, e.g., Serafini, J Nucl. Med. 34:533-6, 1993).

An intact "antibody" typically comprises at least two heavy (H) chains (about 50-70 kD) and two light (L) chains (about 25 kD) inter-connected by disulfide bonds. The recognized immunoglobulin genes encoding antibody chains include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Each heavy chain of an antibody is comprised of a heavy chain variable region ($V_H$) and a heavy chain constant region. The heavy chain constant region is comprised of three domains, $C_{H1}$, $C_{H2}$ and $C_{H3}$. Each light chain is comprised of a light chain variable region ($V_L$) and a light chain constant region. The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system and the first component (Clq) of the classical complement system.

The $V_H$ and $V_L$ regions of an antibody can be further subdivided into regions of hypervariability, also termed complementarity determining regions (CDRs), which are interspersed with the more conserved framework regions (FRs). Each $V_H$ and $V_L$ is composed of three CDRs and four FRs, arranged from amino-terminus to carboxyl-terminus in the following order: FR1, CDR1, FR2, CDR2, FR3, CDR3, FR4. The locations of CDR and FR regions and a numbering system have been defined by, e.g., Kabat et al., *Sequences of Proteins of Immunological Interest*, U.S. Department of Health and Human Services, U.S. Government Printing Office (1987 and 1991).

Antibodies to be used in the invention also include antibody fragments or antigen-binding fragments which contain the antigen-binding portions of an intact antibody that retain capacity to bind the cognate antigen. Examples of such antibody fragments include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an intact antibody; (v) disulfide stabilized Fvs (dsFvs) which have an interchain disulfide bond engineered between structurally conserved framework regions; (vi) a single domain antibody (dAb) which consists of a $V_H$ domain (see, e.g., Ward et al., Nature 341:544-546, 1989); and (vii) an isolated complementarity determining region (CDR).

Antibodies suitable for practicing the present invention also encompass single chain antibodies. The term "single chain antibody" refers to a polypeptide comprising a $V_H$ domain and a $V_L$ domain in polypeptide linkage, generally linked via a spacer peptide, and which may comprise additional domains or amino acid sequences at the amino- and/or carboxyl-termini. For example, a single-chain antibody may comprise a tether segment for linking to the encoding polynucleotide. As an example, a single chain variable region fragment (scFv) is a single-chain antibody. Compared to the $V_L$ and $V_H$ domains of the Fv fragment which are coded for by separate genes, a scFv has the two domains joined (e.g., via recombinant methods) by a synthetic linker. This enables them to be made as a single protein chain in which the $V_L$ and $V_H$ regions pair to form monovalent molecules.

Antibodies that can be used in the practice of the present invention also encompass single domain antigen-binding units which have a camelid scaffold. Animals in the camelid family include camels, llamas, and alpacas. Camelids produce functional antibodies devoid of light chains. The heavy chain variable ($V_H$) domain folds autonomously and functions independently as an antigen-binding unit. Its binding surface involves only three CDRs as compared to the six CDRs in classical antigen-binding molecules (Fabs) or single chain variable fragments (scFvs). Camelid antibodies are capable of attaining binding affinities comparable to those of conventional antibodies.

The various antibodies or antigen-binding fragments described herein can be produced by enzymatic or chemical modification of the intact antibodies, or synthesized de novo using recombinant DNA methodologies, or identified using phage display libraries. Methods for generating these antibodies or antigen-binding molecules are all well known in the art. For example, single chain antibodies can be identified using phage display libraries or ribosome display libraries, gene shuffled libraries (see, e.g., McCafferty et al., Nature 348:552-554, 1990; and U.S. Pat. No. 4,946,778). In particular, scFv antibodies can be obtained using methods described in, e.g., Bird et al., Science 242:423-426, 1988; and Huston et al., Proc. Natl. Acad. Sci. USA 85:5879-5883, 1988. Fv antibody fragments can be generated as described in Skerra and Plückthun, Science 240:1038-41, 1988. Disulfide-stabilized Fv fragments (dsFvs) can be made using methods described in, e.g., Reiter et al., Int. J. Cancer 67:113-23, 1996. Similarly, single domain antibodies (dAbs) can be produced by a variety of methods described in, e.g., Ward et al., Nature 341:544-546, 1989; and Cai and Garen, Proc. Natl. Acad. Sci. USA 93:6280-85, 1996. Camelid single domain antibodies can be produced using methods well known in the art, e.g., Dumoulin et al., Nature Struct. Biol. 11:500-515, 2002; Ghahroudi et al., FEBS Letters 414:521-526, 1997; and Bond et al., J Mol Biol. 332:643-55, 2003. Other types of antigen-binding fragments (e.g., Fab, F(ab')$_2$ or Fd fragments) can also be readily produced with routinely practiced immunology methods. See, e.g., Harlow & Lane, *Using Antibodies, A Laboratory Manual*, Cold Spring Harbor Laboratory Press, Cold Spring Harbor, N.Y., 1998.

An intrabody is an antibody that works within the cell to bind to an intracellular protein. Due to the lack of a reliable mechanism for bringing antibodies into the cell from the extracellular environment, this typically requires the expression of the antibody within the target cell. Because antibodies ordinarily are designed to be secreted from the cell, intrabodies require special alterations, including the use of single-chain antibodies (scFvs), modification of immunoglobulin $V_L$ domains for hyperstability, selection of antibodies resistant to the more reducing intracellular environment, or expression as a fusion protein with maltose binding protein or other stable intracellular proteins.

Binding affinity is generally expressed in terms of equilibrium association or dissociation constants ($K_a$ or $K_d$, respectively), which are in turn reciprocal ratios of dissociation and association rate constants ($k_d$ and $k_a$, respectively). Thus, equivalent affinities may correspond to different rate constants, so long as the ratio of the rate constants remains the same.

The term "contacting" has its normal meaning and refers to combining two or more agents (e.g., polypeptides or phage), combining agents and cells, or combining two populations of different cells. Contacting can occur in vitro, e.g., mixing two polypeptides or mixing a population of antibodies with a population of cells in a test tube or growth medium. Contacting can also occur in a cell or in situ, e.g., contacting two polypeptides in a cell by coexpression in the cell of recombinant polynucleotides encoding the two polypeptides, or in a cell lysate.

A "fusion" protein or polypeptide refers to a polypeptide comprised of at least two polypeptides and a linking sequence or a linkage to operatively link the two polypeptides into one continuous polypeptide. The two polypeptides linked in a fusion polypeptide are typically derived from two independent sources, and therefore a fusion polypeptide comprises two linked polypeptides not normally found linked in nature.

"Heterologous", when used with reference to two polypeptides, indicates that the two are not found in the same cell or microorganism in nature. Allelic variations or naturally-occurring mutational events do not give rise to a heterologous biomolecule or sequence as defined herein. A "heterologous" region of a vector construct is an identifiable segment of polynucleotide within a larger polynucleotide molecule that is not found in association with the larger molecule in nature. Thus, when the heterologous region encodes a mammalian gene, the gene will usually be flanked by polynucleotide that does not flank the mammalian genomic polynucleotide in the genome of the source organism.

A "ligand" is a molecule that is recognized by a particular antigen, receptor or target molecule. Examples of ligands that can be employed in the practice of the present invention include, but are not restricted to, agonists and antagonists for cell membrane receptors, toxins and venoms, viral epitopes, hormones, hormone receptors, polypeptides, peptides, enzymes, enzyme substrates, cofactors, drugs (e.g. opiates, steroids, etc.), lectins, sugars, polynucleotides, nucleic acids, oligosaccharides, proteins, and monoclonal antibodies.

"Linkage" refers to means of operably or functionally connecting two biomolecules (e.g., polypeptides or polynucleotides encoding two polypeptides), including, without limitation, recombinant fusion, covalent bonding, disulfide bonding, ionic bonding, hydrogen bonding, and electrostatic bonding. "Fused" refers to linkage by covalent bonding. A "linker" or "spacer" refers to a molecule or group of molecules that connects two biomolecules, and serves to place the two molecules in a preferred configuration with minimal steric hindrance.

Multiplicity of infection or MOI refers to the ratio of infectious agents (e.g. phage or virus) to infection targets (e.g., cell). For example, when referring to a group of cells inoculated with infectious virus particles, the multiplicity of infection or MOI is the ratio of the number of infectious virus particles to the number of target cells present in a defined space.

The term "operably linked" when referring to a nucleic acid, refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

As used herein, phenotypic selection or selection for an altered phenotype refers to a process in which a library of candidate antibodies expressed inside a producer cell (a population of cells of a eukaryotic cell type) are examined for ability to cause a change in a specific phenotype of an indicator cell. The indicator cell can be the same cell producing the antibodies (producer cell) or a different cell. The specific phenotype of the indicator cell to be altered can be any activity or cellular process other than specific binding of the antibodies to target molecules. Upon contacting the antibody library (or the producer cells expressing the antibodies) with a homogeneous population of indicator cells, those antibodies which cause an alteration in the phenotype of interest are then identified as phenotypic modulators of the indicator cell.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

Polypeptides are polymer chains comprised of amino acid residue monomers which are joined together through amide bonds (peptide bonds). The amino acids may be the L-optical isomer or the D-optical isomer. In general, polypeptides refer to long polymers of amino acid residues, e.g., those consisting of at least more than 10, 20, 50, 100, 200, 500, or more amino acid residue monomers. However, unless otherwise noted, the term polypeptide as used herein also encompass short peptides which typically contain two or more amino acid monomers, but usually not more than 10, 15, or 20 amino acid monomers.

Proteins are long polymers of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies. In some embodiments, the terms polypeptide and protein may be used interchangeably.

Unless otherwise noted, the term "receptor" broadly refers to a molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. A typical example of receptors which can be employed in the practice of the invention is cell surface signaling receptor.

The term "subject" refers to human and non-human animals (especially non-human mammals). In addition to human, it also encompasses other non-human animals such as cows, horses, sheep, pigs, cats, dogs, mice, rats, rabbits, guinea pigs, monkeys.

Trans-differentiation, also known as lineage reprogramming, is a process where one mature somatic cell or lineage-restricted stem cell transforms into another mature somatic cell without undergoing an intermediate pluripotent state or progenitor cell type. It is a type of metaplasia, which includes all cell fate switches, including the interconversion of stem cells. Current uses of trans-differentiation include disease modeling and drug discovery and in the future may include gene therapy and regenerative medicine. The term 'trans-differentiation' was originally coined by Selman and Kafatos (Cell differentiation 3: 81-94, 1974) to describe a change in cell properties as cuticle producing cells became salt-secreting cells in silk moths undergoing metamorphosis.

The term "target," "target molecule," or "target cell" refers to a molecule or biological cell of interest that is to be analyzed or detected, e.g., a ligand such as a cytokine or hormone, a polypeptide, a cellular receptor or a cell.

A cell has been "transformed" by exogenous or heterologous polynucleotide when such polynucleotide has been introduced inside the cell. The transforming DNA may or may not be integrated (covalently linked) into the genome of the cell. In prokaryotes, yeast, and mammalian cells for example, the transforming polynucleotide may be maintained on an episomal element such as a plasmid. With respect to eukaryotic cells, a stably transformed cell is one in which the transforming polynucleotide has become integrated into a chromosome so that it is inherited by daughter cells through chromosome replication. This stability is demonstrated by the ability of the eukaryotic cell to establish cell lines or clones comprised of a population of daughter cells containing the transforming polynucleotide. A "clone" is a population of cells derived from a single cell or common ancestor by mitosis. A "cell line" is a clone of a primary cell that is capable of stable growth in vitro for many generations.

A tumor suppressor gene, or anti-oncogene, is a gene that protects a cell from one step on the path to cancer. When this gene is mutated to cause a loss or reduction in its function, the cell can progress to cancer, usually in combination with other genetic changes. Examples of tumor suppressor genes include the p53 gene and the p27Kip1 cell-cycle inhibitor gene.

A "vector" is a replicon, such as plasmid, phage or cosmid, to which another polynucleotide segment may be attached so as to bring about the replication of the attached segment. Vectors capable of directing the expression of genes encoding for one or more polypeptides are referred to as "expression vectors".

III. Expressing Combinatorial Antibody Library Inside Eukaryotic Cells

The invention provides novel methods that allow one to select directly for functional antibodies in eukaryotic cells. The methods rely on construction of a combinatorial antibody library (e.g., via lentiviral vectors) which, upon infection, lead to efficient expression of antibodies inside the eukaryotic host cells. The antibodies expressed inside the cells can be secreted from the cells or remain inside the cell as intrabodies. As a result, modulation of both intracellular and extracellular targets by the antibodies can be accessed. Typically, to directly correlate an observed phenotype alteration with a specific antibody molecule or antibody-encoding sequence, the antibody library is introduced into and expressed in the cells under conditions each cell expresses no more than about 2 or 3 different antibodies or antibody-encoding sequences (e.g., scFv sequences). In some embodiments, each individual cell of the heterogeneous population of recombinantly produced cells expresses no more than one different member of the antibody library. With a lentiviral or retroviral based vector system as exemplified herein, this can be accomplished by infecting the producer or indicator cells the antibody-expressing viruses at a relatively low multiplicity of infection (MOI), e.g., not higher than 2 or 3. For selection of homomeric antibodies only, infection of the cells by the viruses can be performed at a lower MOI, e.g., less than about 1. To allow for selection of bispecific heterodimeric antibody modulators, the antibody-expressing sequences can be transduced into the cells at a higher MOI, e.g., about 2 or 3. Under these conditions, an antibody modulator can be directly identified from an observed phenotype alteration with little or no further test of the antibodies that are isolated from positive clones in the phenotype assay.

The methods described herein can be used to select antibodies that modulate various phenotypes of eukaryotic cells. In some embodiments, the identified antibody modulators are phenocopies of a target molecule which modulates a phenotype of or effectuates a cellular response in the host eukaryotic cell (e.g., erythropoietin). Typically, the phenotype is mediated directly or indirectly by a target molecule (e.g., a receptor or a signaling ligand) against which an antibody modulator is to be selected in the methods of the invention. The candidate antibodies can be selected for modulators that agonize the target molecule (e.g., Epo or EpoR). The candidate antibodies can also be selected for modulators that antagonize the target molecule (e.g., TNFα or an oncogene product) or antagonize an inhibitor (e.g., IL-1 receptor antagonist IL-1Rα) of the target molecule (e.g., IL-1α or IL-1β).

In some embodiments, the combinatorial antibody library is expressed inside a population of cells to select antibody modulators of a phenotype of the same type of cells ("indicator cells"). In these embodiments, the antibodies can be either secreted from the cells or stay inside the cells as intrabodies. In some other embodiments, the antibodies are expressed in and secreted from a population of cells of a second cell type ("producer cells") for selection of modulators of a phenotype of the indicator cells. In these embodiments, the indicator cells are typically co-cultured under suitable conditions with the antibody-expressing producer cells to allow interaction of the secreted antibodies with the indicator cells.

The antibody library can express intact full length antibodies or antigen-binding fragments containing the antigen-binding portions of an intact antibody (i.e., antibody fragments that retain capacity to bind the cognate antigen). The antibodies produced by the antibody library can be single or double chain. In some embodiments, a single chain antibody library is expressed inside a eukaryotic producer cell. Single chain antibody libraries can comprise the heavy or light chain of an antibody alone or the variable domain thereof. More typically, members of single-chain antibody libraries are generated by a fusion of heavy and light chain variable domains separated by a suitable spacer within a single contiguous protein. See e.g., Ladner et al., WO 88/06630; McCafferty et al., WO 92/01047. In other embodiments, double-chain antibodies may be formed inside the producer cell by noncovalent association of separately expressed heavy and light chains or binding fragments thereof. The diversity of antibody libraries can arise from obtaining antibody-encoding sequences from a natural source, such as a non-clonal population of immunized or unimmunized B cells. Alternatively, or additionally, diversity can be introduced by artificial mutagenesis of antibodies for a target molecule. Typically, antibody libraries employed in the present invention contains at least $10^2$, $10^3$, $10^4$, $10^5$, $10^6$, $10^7$, $10^8$, $10^9$, $10^{10}$ or more different members or species.

Various known libraries of antibodies can be utilized and modified as necessary in the practice of the selection methods of the invention. The antibody library can comprise unrelated antibodies from a naïve antibody library. For example, libraries of naïve antibodies (e.g., scFv libraries from human spleen cells) can be prepared as described in Feldhaus et al., Nat. Biotechnol. 21:163-170, 2003; and Lee et al., Biochem. Biophys. Res. Commun. 346:896-903, 2006. Park et al. (Antiviral Res. 68:109-15, 2005) also described a large non-immunized human phage antibody library in single-chain variable region fragment (scFv) format. Antibodies library derived from a subject with a specific disease can be prepared from RNA extracted from peripheral blood lymphocytes of the subject, using methods as described in Kausmally et al. (J. Gen. Virol. 85:3493-500, 2004). Alternatively, the antibody library can comprise synthetic antibodies or antibodies derived from a specific antibody, e.g., by DNA shuffling or mutagenesis. For example, Griffiths et al. (EMBO J 13:3245-3260, 1994) described a library of human antibodies generated from large synthetic repertoires (lox library). Some embodiments of the invention can employ libraries of antibodies that are derived from a specific scaffold antibody. Such antibody libraries can be produced by recombinant manipulation of the reference antibody using methods described herein or otherwise well known in the art. For example, Persson et al. (J. Mol. Biol. 357:607-20, 2006) described the construction of a focused antibody library for improved hapten recognition based on a known hapten-specific scFv.

In some preferred embodiments of the invention, the antibody library expresses single chain antibodies such as single chain variable region fragments (scFv). A specific scFv library suitable for the present invention is described in the Examples below and also in the art, e.g., Gao et al., Proc. Natl. Acad. Sci. 99:12612-6, 2002. Such an antibody library can be generated with and expressed from various vectors well known in the art. Preferably, the antibody library used in the invention is constructed via a lentiviral or retroviral based vector. Construction of such antibody library for expression inside a eukaryotic host cell can be performed in accordance with the techniques exemplified herein and other methods well known in the art. In some embodiments, the antibody library is constructed with a lentiviral vector. Lentiviral vectors are retroviral vectors that are able to transduce or infect both dividing and non-dividing cells and typically produce high viral titers. Examples of lentiviral based vectors suitable for the invention include, e.g., lentiviral vector pLV2 exemplified herein. For example, as detailed in the Examples below, a lentiviral based combinatorial scFv antibody library can be generated by cloning SfiI digested genes encoding the scFv into SfiI digested pLV2 vector to express scFv in the same frame as the Fc portion of human IgG1 (from hinge to $C_H3$). Other lentiviral vectors that may be employed and modified for practicing the invention include, e.g., pLVX-Puro, pLVX-IRES-Neo, pLVX-IRES-Hyg, and pLVX-IRES-Puro. The various lentiviral vectors with cloned antibody sequences can be introduced into an appropriate host cell for expressing the antibody library. For example, the TF-1 cell line and HEK293T cell line exemplified herein, as well as other packaging cell lines well known in the art (e.g., Lenti-X 293T cell line), may be employed for expressing the antibody library in the invention. In addition to lentiviral based vectors and host cells, other retroviral based vectors and expression systems may also be employed in the practice of the methods of the invention. These include MMLV based vectors pQCXIN, pQCXIQ and pQCXIH, and compatible producer cell lines such as HEK 293 based packaging cell lines GP2-293, EcoPack 2-293 and AmphoPack 293, as well as NIH/3T3-based packaging cell line RetroPack PT67.

As noted above, the antibodies produced from the host or producer cells can be either contained inside the cells (i.e., as intrabodies) or secreted from the cells. In some embodiments, the antibody-producing cell is the same cell to be studied for obtaining an antibody modulator of its phenotype. In these embodiments, depending on the specific phenotype to be modulated, the antibodies can be either secreted from the cell or present as intrabodies inside the cell. Because antibodies ordinarily are designed to be secreted from the producer cell, intrabodies require special alterations, including the use of single-chain antibodies (scFvs), modification of immunoglobulin $V_L$ domains for hyperstability, selection of antibodies resistant to the more reducing intracellular environment, or expression as a fusion protein with maltose binding protein or other stable intracellular proteins. Such optimizations can improve the stability and structure of intrabodies. A library expressing intrabodies can be used in selecting for modulators of cellular phenotypes through intracellular target molecules. For example, a combinatorial library of intrabodies can be used to select for modulators of intracellular pathways in a healthy or diseased cell. Identification of such antibody modulators could in turn lead to discovery of novel drug targets against which smaller, cell-penetrable compounds can be designed or screened (e.g., siRNA or small organic agents).

In some embodiments, the antibody library is constructed for secreting the expressed antibodies so that the antibodies can be selected for modulators of a target molecule that is extracellular or present on cell surface (e.g., a cell surface receptor or integrin). In these embodiments, the indicator cells expressing the antibodies (or both the indicator cells and antibody expressing cells for the co-culturing selection format described herein) are preferably grown and maintained in a diffusion restricting matrix, e.g., methylcellulose or agarose. The diffusion restricting culture medium can trap the secreted antibodies around the cells to ensure physical interaction of the antibodies with the indicator cells during the selection process.

In some embodiments, the antibody library is expressed in a population of cells of a second cell type ("producer cell"). As noted above, to allow for direct correlation of an observed phenotype with a specific antibody molecule, the antibody library is typically introduced into the producer cells under conditions each cell expresses no more than about 2 or 3 different antibody species. In some embodiments, each cell expresses only one different member of the antibody library. While the second cell type can be the same or different from the cell type of the indicator cell, the producer cell and the indicator cell are typically of different cell types or strains. In these embodiments, the second cell (the antibody producing cells) is typically present in close vicinity of the indicator cell, e.g., by co-culturing the two types of cells in a diffusion restricting medium such as methylcellulose agar. For example, the indicator cell can be a tumor cell (or other diseased cells) against which a growth-inhibiting or apoptosis-stimulating antibody modulator is to be selected. Thus, in some of such co-culturing selection formats, antibodies expressed in and secreted from a second cell are selected for modulators that kill or inhibit (slow or stop) the growth of an indicator cell. Some embodiments of the invention are directed to identifying functional antibodies for a target molecule in various tumors. For example, candidate antibodies can be selected for therapeutic antibodies targeting EGF receptor in colon cancer or targeting VEGF in several types of cancer (e.g., colorectal cancer, lung cancer and metastatic breast cancer). In some other embodiments, candidate antibodies can be selected for therapeutic antagonist antibodies targeting HER1/EGFR for inhibiting tumor cell motility, adhesion and metastatic potential. In some other embodiments, the antibodies can be selected for agents targeting HER2 and HER3 which are implicated in breast cancer. In still some other embodiments, the antibody library expressed inside a producer cell can be employed to select agonist antibodies targeting TRAIL-R1, TRAIL-R2 or other death receptors for inducing selective apoptosis in a variety of tumor cells.

As disclosed herein, the selection methods of the invention in general do not require the target molecule of the to-be-identified antibodies to be known in advance. Nevertheless, some embodiments of the invention are directed to identify modulators of a phenotype that is mediated by a specific known target molecule. The target molecule can be an endogenous or heterologous molecule of the indicator cell. For example, the phenotype can be a signaling activity mediated by a receptor (e.g., EpoR or IL-1R) located inside or on the surface of the cell or a corresponding ligand of the receptor. For example, the selection methods of the invention are suitable for identifying antibody modulators of various secreted cytokines or hormones. Examples include Epo, thrombopoietin (Tpo), IL-1β, TNFα and Glucagon-like peptide-1 (GLP-1). Modulators of a phenotype mediated by these molecules typically include agonists or antagonists of the target molecule (the receptor or the ligand), as well as modulators (e.g., neutralizing antibodies) of an inhibitor of the target molecule. For example, the antibody library can be selected for agonists of EpoR or IL-1R as exemplified herein. The candidate antibodies can also be selected for antagonists of an inhibitor (e.g., IL-1Rα) of a target molecule (e.g., IL-1R). In some other embodiments, the candidate antibodies are selected for antagonists that neutralize a signaling ligand (e.g., TNFα) which mediates an undesired cellular response (e.g., undesired inflammatory response or apoptosis). In some other embodiments, candidate antibodies can be selected for agonist antibodies for a tumor suppressor gene product (e.g., p53) or antagonist antibodies against an oncogene product. For example, erbB2 oncogene encodes a growth factor receptor. In these embodiments, candidate antibodies are selected for antagonists of the receptor.

When the phenotype to be modulated is mediated by a known target molecule, the combinatorial antibody library used in the selection methods of the invention can comprise antibodies raised against the specific target molecule. Various target molecules are suitable for use in the practice of the invention. They can be any biomolecule such as a protein, carbohydrate, lipid or nucleic acid. The target molecules can be associated with a cell ("cell surface expressed") or other particle ("particle surface expressed") such as a virus. They can be intracellular or extracellular. Suitable target molecules include, e.g., signaling ligands such as cytokines or growth hormones and their cellular receptors, viral proteins and host receptors, vitamin receptors, cell surface markers (e.g., CD41), and cell enzymes and their substrates. In some embodiments, the selection methods are directed to identifying modulators of secreted proteins of interest such as cytokines and chemokines, e.g., interleukins (IL-1 through IL-18), tumor necrosis factors α & β, interferons α, β and γ, transforming growth factor alpha and beta (TGF-α and TGF-β), colony stimulating factor (CSF), tumor necrosis factor and granulocyte monocyte colony stimulating factor (GM-CSF). Preparation of a library of antibodies against any of these known target molecules and its expression inside a eukaryotic host cell can be carried out in accordance with standard techniques well known in the art or specifically exemplified herein.

While the antibody modulators of a phenotype of the indicator cells are identified via functional selection (phenotypic selection), the candidate antibodies may be optionally first screened for binding activity prior to functional selection. Thus, when the target molecule against which antibody modulators are to be selected is known, the methods of the invention can include an additional step of screening the combinatorial antibody library to enrich members for recognition of and desired affinity for the target molecule. Screening antibodies for binder to a target molecule can be performed with a number of methods well known in the art. For example, a combinatorial antibody library can be expressed via phage display to select for binding affinity for a target polypeptide. Phage system has been employed successfully for the display of functional proteins such as antibody fragments (scFv or Fab'), hormones, enzymes, and enzyme inhibitors, as well as the selection of specific phage on the basis of functional interactions (antibody-antigen; hormone-hormone receptor; enzyme-enzyme inhibitor). See, e.g., Paschke, Appl. Micbiol. Biotechnol. 70:2-11, 2006; and Kehoe and Kay, Chem Rev. 105:4056-72, 2005. Detailed procedures for screening a combinatorial scFv antibody library for binders to a target molecule (e.g., Epo) via phage display is exemplified herein. More general guidance for using phage display platforms are provided in the art. See, e.g., Barbas et al., *Phage Display: A Laboratory Manual*, Cold Spring Harbor Laboratory Press (2001).

IV. Phenotypic Selection of Antibody Modulators

The invention provides methods for identifying antibody modulators (agonists or antagonists) of a phenotype of interest in eukaryotic cells, especially mammalian cells. The selection methods can be applied to identifying antibody modulators of various phenotypes of interest in the cells, including any cellular response, physiological activity or biological characteristic of the cell (the indicator cell). For example, the modulated phenotypes can be initiation of or alteration in a process or activity linked to signal transduction cascades, induction or repression of expression of a specific gene (e.g., a differentiation indicating marker gene as noted below), a change in a diseased state or pathological condition, an altered morphology or other physical attribute of the cell (e.g., colony formation in a conditional growth medium), and an alteration in cell differentiation or proliferation related activities. As exemplified herein, phenotypes of the indicator cells to be modulated by the candidate antibodies can also be altered growth (stopped or slowed growth), apoptosis, or survival of a particular treatment or inhibition. However, it is important to note that the phenotypes to be modulated by the candidate antibodies in the selection methods of the invention do not encompass specific binding or physical interaction of the antibodies with any target molecule or antigen.

To select for antibody modulators of the cell of interest ("indicator cell" or "target cell"), the library of candidate antibodies can be expressed inside a population of cells of the same indicator cell strain. Alternatively, the antibodies can be expressed inside a population of cells of a second cell type ("producer cells") prior to being contacted with the indicator cells. In the latter case, the antibody expressing producer cells and the indicator cells whose phenotype is to be examined are typically co-cultured under appropriate conditions. Modulation of the phenotype in the examined cells is typically determined by comparing to the same phenotype of control cells which are not subject to interaction with the antibodies. A significant departure or change of the phenotype in the cell contacted with a specific antibody relative to that of the control cell would identify the specific antibody as a modulator of the cell. Except for selecting intrabodies, the antibody-expressing indicator cells (or both the producer cells and the indicator cells in the co-culturing format) can be preferably grown and maintained in a diffusion restricting matrix during the selection process. This is to ensure sufficient contact and interaction between the secreted antibodies and the indicator cells to allow potential antibody modulators to exert their effects on the cells. Thus, some embodiments of the invention can employ diffusion restricting growth media such as methylcellulose or agarose.

Various cell types can be employed as the indicator cell in the selection methods of the invention. These include established cell lines as well as primary cells isolated from a eukaryotic organism (e.g., a mammal such as human). As exemplified herein, primary cells such as stem cells isolated from bone marrow of a subject can be readily used as the indicator cell to select for antibody modulators of its phenotype (e.g., differentiation). In some of these embodiments, the indicator cell can be put into contact with a library of candidate antibodies expressed in a producer cell. Similarly, established mammalian cells lines such as TF-1 and HEK293T can be readily used for selecting antibody modulators of many phenotypes of mammalian cells, e.g., agonists or antagonist of signaling transduction pathways. Other well-known mammalian cell lines that can be used and modified for practicing the methods of the invention include, e.g., CHO, HeLa, D10S, COS, MDCK, 293, WI38 and Jurkat E6 cells. In some other methods, primary cells can be employed to select antibody modulators of a specific phenotype of the cell. For example, stem cells isolated from a mammalian species (e.g., human) can be used to select for antibody modulators that promote proliferation or differentiation of the cells. These cells are suitable for identifying antibody modulators of various cellular responses and signaling pathways, e.g., thrombopoietin agonist antibodies for promoting hematopoietic stem cell differentiation. Similarly, a tumor cell isolated from a mammalian subject can be employed to select for antibody modulators that inhibit growth or stimulate apoptosis of the cell. Apoptosis or altered growth of the indicator cell can be readily assessed via various methods well known in the art. For example, apoptosis of the indicator cell can be monitored via an ethidium homodimer (EthD-1) assay which is a routinely practiced assay used to detect dead or dying cells. In some other embodiments, antibodies expressed in and secreted from a producer cell are selected for modulators of other phenotypes of the indicator cell. As detailed below, alteration of the various phenotypes and/or morphology of the indicator cells can be examined by standard techniques readily available in the art. These include introducing a reporter gene or specific biomarker into the indicator cell that can be easily detected (e.g., by immunofluorescence).

Phenotypic selection can be performed by either positive or negative selection. In positive phenotypic selection, antibody modulators are identified through a positive response or activity in the cell relative to a control cell not subjected to interaction with the antibodies. As exemplified herein for selecting Epo agonist antibodies, the indicator cells can be selected for positive cell growth or proliferation that depends on activation by an agonist antibody of a relevant signaling pathway. In addition, agonist antibodies that elicit a signaling pathway can be selected for expression of a reporter gene placed under the control of a specific promoter (e.g., TNF-β promoter or GLP-1 responsive promoter) that is activated by the signaling pathway (e.g., IL-2 mediated Jak-STAT signal pathway). Reporter genes used in this type of selection can be, e.g., genes conferring a detectable physical attribute (e.g., GFP and beta-lactamase) or antibiotic resistance (e.g., aminoglycoside phosphotransferase) to the cell. For example, Tpo agonist antibodies can be selected in an antibody-expressing reporter cell line in which expression of a fluorescent marker gene is controlled by TpoR signaling pathway.

In negative phenotypic selection, antibody modulators are identified for their activity to inhibit or suppress a phenotype, activity or response that is otherwise detectable in control cells that are not subject to the antibodies. For example, a toxin-encoding reporter gene (e.g., diphteria toxin gene) can be placed under the control of a promoter (e.g., TNF-β promoter) that is activated by a signaling cascade (e.g., IL-2 mediated Jak-STAT signal pathway). Antagonist antibodies of the signaling pathway can be selected for their ability to inhibit the signaling pathway, and as a result, to suppress expression of the toxin and ensure growth of the cell. Thus, a normal or less inhibited growth of the cell, relative to suppressed growth of a control cell (which are not contacted with the antibodies) due to toxin expression, would identify an antagonist antibody modulator of the specific signaling pathway in the cell.

To identify antibody modulators of various phenotypes of the target cell, many assays can be modified and adapted for use in the selection methods of the invention. Exemplary methods for evaluating phenotypes of cells include microscopy (e.g., light, confocal, fluorescence, scanning electron, and transmission electron), fluorescence based cell sorting, differential centrifugation, differential binding, immunoassays, enzymatic assays, growth assays, and in vivo assays. As exemplified herein for Tpo agonist antibodies, fluorescence based cell sorting can be used to select antibody modulators of a signaling cascade in cells wherein expression of a fluorescent marker gene is linked to activation of that signaling pathway. In some embodiments, phenotypic behaviors of the cell such as chemotaxis, morphological changes, or apoptosis can be monitored via visual inspection or microscope examination. Optionally, computer software programs can be used to automatically detect cells with altered phenotype. To this end, various high-content screens ("HCS") have been developed to address the need for more detailed information about the temporal-spatial dynamics of cell constituents and processes. High-content screens automate the extraction of multicolor fluorescence information derived from specific fluorescence-based reagents incorporated into cells (see, e.g., Giuliano and Taylor, Curr. Op. Cell Biol. 7:4, 1995). Cells are analyzed using an optical system that can measure spatial, as well as temporal dynamics. In addition, many fluorescent physiological indicators and "biosensors" are available to monitor changes in biochemical and molecular activities within cells (see, e.g., Giuliano et al., Ann. Rev. Biophys. Biomol. Struct. 24:405, 1995).

In various embodiments of the invention, phenotypes of the indicator cells can be evaluated using a biochemical assay or other indicator associated with the desired phenotype. As exemplification, the Examples below describe specific TF-1 cell proliferation assay, colony formation assay for monitoring erythroid differentiation of human stem cells, hemoglobin expression assay for monitoring TF-1 cell differentiation, and STAT5 phosphorylation assay for monitoring EpoR signaling pathway. These assays can all be employed and modified as necessary in the practice of the present invention. Thus, in some embodiments, antibody modulators which cause cells to proliferate at an altered rate relative to a control cell are identified via suitable proliferation assays. For example, antagonist antibodies for IL-1Rα can be selected by recovering cell proliferation activity mediated by IL-1β of an appropriate indicator cell (e.g., D10S cell; Orencole et al., Cytokine 1:14-22, 1989) from the inhibitory effect of IL-1Rα. In some embodiments, cells that have an altered response to a stimulatory signal (e.g., a growth factor or other mitogen) are identified via biochemical assays or other reporter assays corresponding to the specific signaling pathway. Assays for detecting and evaluating the intracellular transduction of an extracellular signal using recombinant cells that express cell surface receptors and contain reporter gene constructs are well known in the art (see, e.g., U.S. Pat. Nos. 5,401,629 and 5,436,128).

In some other embodiments, antibody modulators of cell differentiation are selected. Suitable marker proteins can be used to modulate the differentiative and proliferative capacity of a variety of cells, including stem cells, such as ES cells and somatic stem cells. Differentiation of cells (e.g., stem cells) can be readily examined via many techniques well known in the art. For example, expression of marker genes and marker proteins can be utilized to evaluate cell differentiation. Examples of such markers include CD41 for hematopoietic stem cell to differentiate into megakaryocytes; FLK1 for endothelial cells (Cho et al., Blood 98:3635-42, 2001; Nishikawa et al., Development 125: 1747-1757, 1998), vascular smooth muscle cell-specific myosin heavy chain for smooth muscle (Drab et al., FASEB J. 11:905-15, 1997), Bone-specific alkaline phosphatase (BAP) and osteocalci for osteoblasts (Demers et al., Cancer 88:2919-26, 2000), CD4, CD8 and CD45 for white blood cells (Ody et al., Blood 96:3988-90, 2000; and Martin et al., Blood 96:2511-9, 2000), Flk-2 and CD34 for hematopoietic stem cells (Julie et al., Proc. Natl. Acad. Sci. USA, 98:14541-14546, 2001; Woodward & Jenkinson. Eur. J. Immunol. 31:3329-38, 2001; and George et al., Blood 97:3925-30, 2001), CFU for hematopoietic stem cells and MSC progenitors (Frimberger et al., Exp. Hematol. 29:643-52, 2001), Muc-18 (CD146) for bone marrow fibroblasts (Filshie et al., Leukemia 12:414-21, 1998), collagen type II, collagen type IV and chondrocyte expressed protein-68 for chondrocytes (Carlberg et al., Differentiation 67:128-38, 2001, Steck et al., Biochem. J. 353:169-74, 2001), adipocyte lipid-binding protein (ALBP) and fatty acid transporter for adipocytes (Amri, et al., J. Biol. Chem. 270:2367-2371, 1995; Bastie et al., J. Biol. Chem. 274:21920-5, 1999; Frohnert et al., J. Biol. Chem. 274: 3970-3977, 1999; and Teboul et al., Biochem. J. 360:305-312, 2001), CD133 for neural stem cells (Uchida N et al., Proc. Natl. Acad. Sci. USA 97:14720-5, 2000), GFAP for astrocytes (Dai et al., Genes Dev. 15:1913-25, 2001), and microtubule-associated protein-2 for neurons (Roy et al., Nat. Med. 6:271-7, 2000).

The methods of the invention can also be used for selecting antibody modulators of other properties of mammalian cells such as anti-tumorigenesis, altered apoptosis, and anti-viral phenotypes. For example, the methods can be adapted for selecting antibody modulators that confer to the cells resistance to viral infection or virus production. Similarly, modulators that lead to changes in cell signaling pathways can be detected by the use of probes correlated with activity or inactivity of the pathway or by observable indications correlated with activity or inactivity of the pathway. In some other embodiments, the selection is intended for identifying modulators that cause an alteration in the expression or synthesis a compound of interest in the indicator cells, e.g., a metabolite, a secreted protein, and a post-translationally modified protein. Such antibody modulators can be identified by a variety of means, including the use of a responder cell, microarrays, chemical detection assays, and immunoassays. In some embodiments, antibody modulators are selected for enhancing transfection efficiency by a virus or viral vector into the indicator cell. Selection for such phenotypic modulators can be performed by transfecting the cell with a reporter or marker construct at limiting concentrations and selecting antibodies that facilitate uptake of the reporter construct by the cell.

In some embodiments, the selection methods are directed to identifying antibody modulators that modulate proliferation or differentiation of stem cells. The antibody modulators may modulate stem cell proliferation or differentiation by exerting an effect (inhibition or activation) on key cytokines and growth factors. An ability to control the differentiative and proliferative potential of stem cells could enable, among other things, the provision of a large supply of undifferentiated cells, and the regulated differentiation toward specific cell types. Thus, in some embodiments of the invention, a combinatory library of candidate antibodies expressed inside the producer cells can be selected for modulators that promote differentiation of stem cells towards a defined post-mitotic cell subtype (e.g., a dopaminergic or cholinergic neuron) or that direct embryonic stem (ES) cells to differentiate into a restricted lineage (e.g., neuronal progenitor cells or hematopoietic stem cells). In some embodiments, candidate antibodies are selected for modulators that cause a differentiated cell to adopt a different differentiated state or that allow a differentiated cell to adopt a non-differentiated state, e.g., thereby generating a stem cell or a pluripotent progenitor cell. In some other embodiments, the candidate antibodies are selected for modulators that increase the potential for self-renewal, that prevent differentiation, or that direct the extent and character of differentiation. In various embodiments for selecting modulators of stem cells, the antibodies can be expressed inside the stem cells or stem cell progenitor cells, which is followed by evaluating a specific phenotype of the cell.

As noted above, modulation of many phenotypes of the indicator cells can be examined via the use of a reporter construct. The reporter construct is introduced into the indicator cell to provide a measurable signal (detectable label) in response to modulation of a corresponding phenotype of the cell (e.g., a signaling activity at a cell surface receptor). The reporter gene in the reporter construct can encode an enzyme (e.g., β-lactamase or β-galactosidase) which can catalyze a detectable enzymatic reaction (e.g., one linked to a detectable colorimetric or fluorimetric reaction). The reporter construct can also express a molecule that provides a detectable fluorescent signal or chemiluminescent (e.g., green fluorescent protein GFP).

Reporter constructs for monitoring activities of various signaling cascades can be generated and introduced into the indicator cell in accordance with methods well known in the art. For example, vectors suitable for making the reporter constructs can be plasmids (e.g. pUC18, pYES2, pCDM8) or viral genomes such as adenovirus, AAV or retroviral vectors (Moloney murine leukemia virus (MoMuLV), gibbon ape leukemia virus (GaLV). Depending on the phenotype to be modulated, the reporter gene (e.g., a gene encoding an addressable enzyme, a toxin or GFP) can be placed under the control of various promoters that are responsive to modulation of the phenotype. Examples include bcl-x promoter (for erythropoietin pathway), TNF-β promoter (for IL-2 signaling), U6 or tRNA$^{met}$ promoter, retroviral long terminal repeats, and T7 RNA polymerase promoter. Other suitable vectors and promoter elements suitable for the reporter constructs and protocols for cloning, transfecting, transient gene expression and obtaining stable transfected cell lines are described in the art, e.g., Sambrook et al., Molecular Cloning: A Laboratory Manual, Cold Spring Harbor Press, N.Y., ($3^{rd}$ ed., 2000); and Brent et al., Current Protocols in Molecular Biology, John Wiley & Sons, Inc. (ringbou ed., 2003).

V. Tans-Differentiating Target Cells Via Protein Agonists

The present invention provides methods for selecting protein agents capable of reprograming or trans-differentiating target cell, e.g., differentiated somatic cells or lineage-restricted stem cells. Some related embodiments of the invention are directed to methods of using such protein agents (e.g., a receptor agonist antibody) to reprogram or tans-differentiate the target cells. For example, protein agents (e.g., polypeptides or antibody agonists) can be selected for activity in reprograming a target cell (e.g., myloid lineage CD34+ cells) along a different path (e.g., to trans-differentiate into neural progenitors). As demonstrated herein, the selection format of the invention allows one to identify protein agents such as antibody agonists which possess rare properties, e.g., ability to modulate a target receptor in a manner that is different from that of the natural ligand of the receptor. As exemplified with G-CSF agonist antibodies selected by the inventors, while both the selected G-CSF agonist antibody and G-CSF bind to the G-CSFR and induce cell proliferation, only the selected G-CSF antibody can initiate neurogenesis.

To reprogram a target cell to trans-differentiate along a desired path, one needs first to identify protein modulators (e.g., agonist antibodies or polypeptide agents), e.g., in a reporter cell, that can activate a signaling pathway or activity indicative of the desired differentiation path. The identified agents can then be further examined to confirm that they are indeed able to reprogram the target cell in the desired manner. Typically, candidate polypeptide agents are expressed in the reporter cell line co-expressing a signaling receptor that is normally present on the target cell. The chosen signaling receptor should be one that in the target cell normally mediates or activates cellular events or specific signaling pathways reflecting or corresponding to the desired differentiation pathway. The candidate protein agents can be, e.g., a library of antibodies or antigen-binding fragments thereof that is raised against the receptor which mediates or activates a specific signaling pathway. The candidate agents can also be other polypeptides or peptides capable of modulating the receptor, e.g., variants or derivatives of a natural ligand of the receptor. The signaling pathway to be monitored in the selection should reflect or correspond to cellular events that initiate or activate the desired differentiation pathway for the target cell, e.g., expression of specific molecular markers indicative of the desired differentiation pathway. For example, to trans-differentiate a target cell into neurons or neural progenitor cells, the receptor to be co-expressed in the reporter cell can be G-CSFR because activation of this receptor can leads to induction of neurogenesis in the central nervous system. An intracellularly expressed library of antibody agents can be first selected in the G-CSFR bearing reporter cells to obtain one or more agonist agents for the receptor. The identified agonists are then applied to the target cell (e.g., myloid CD34+ cells) under appropriate conditions to select for cells with a phenotype or signaling activities evidencing neural lineage, e.g., presence of neuronal tubulin. The identified agents can be additionally subject to other testing to confirm that they are indeed capable of trans-differentiate the target cell alone the desired differentiation path.

In some embodiments, the library of candidate polypeptide agents is co-integrated with the chosen receptor into the plasma membranes of a population of reporter cells. Such a co-localization format favors unusual interactions between receptors and their protein ligands and ensures that the protein agent (e.g., antibody) acts in an autocrine manner on the cells that produce it. The invention has exemplified reprograming of CD34+ myloid cells to become neural progenitors via selecting agonists that activate the co-localized G-CSFR. The generic selection scheme described herein can be broadly applied in identifying agents that can trans-differentiate target cells via modulating other cellular receptors. In the case of GPCRs and cytokine receptors, pluripotency of signaling is a growing area of pharmacology where one aims at finding agonists that bias signaling via a receptor to a particular downstream pathway. To accomplish this, one needs to test a large number of agonists. While this is relatively easy for small molecule ligands, the generation and study of a large and diverse library of protein agonists is more problematic. The methods of the invention provide a solution to this problem in that it facilitates study of a large number of potential protein agonists that bind to different regions of the receptor and favor alternative downstream signaling pathways. The screening autocrine systems by FACS as exemplified herein greatly facilitate phenotypic selections of rare events (e.g., trans-differentiation) and protein agents capable of mediating such rare events. Further, because such interactions occur in the natural milieu of the receptor, they have a higher potential for physiological relevance.

The methods and antibodies of the invention can have various therapeutic applications, e.g., in regenerative medicine. As therapeutics, protein agents such as antibodies have the advantage that they are long lived and do not need to enter cells to function. The antibodies agents could trans-differentiate autologous stem cells in vivo or in vitro to generate differentiated cells that are self. Such cells can be useful in a variety of ways, including the repair of an injured region of the brain or spinal cord.

VI. Bispecific Antibodies

By controlling multiplicity of infection (MOI), more than one antibody-encoding lentivirus or other retrovirus can infect a single cell. In the case of scFv-Fc fusion antibodies as exemplified herein, this allows re-assortment of the antibody Fv domains themselves inside cells to yield heterodimeric antibodies. Accordingly, some embodiments of the invention are directed to identifying heterodimeric bispecific antibodies which target two different antigenic epitopes. While the bispecific antibodies of the invention encompass antibodies which recognize two antigenic epitopes present on two different molecules (trans-reactivity), they typically refer to heterodimers which bind to two different sites within the same molecule (cis-reactivity). The modulator function (agonist or antagonist) of such antibodies depend on the obligate synergy between two different antigen-binding specificities that must be contained within the same antibody molecule. As exemplified herein for anti-Epo bispecific agonist antibodies, this asymmetric binding of the heterodimeric antibody replicates the mechanism of the authentic target molecule (e.g., Epo) whose full agonist activity depends on asymmetric binding to two binding sites on its receptor.

The ability to select directly synergistic antibodies from cells expressing more than one antibody offers a second combinatorial degree of freedom that operates at the level of whole scFv antibodies and can add to the diversities already achieved by the random association of very large numbers of antibody heavy and light chains. Thus, the first combinatorial parameter is the random association of heavy and light chains of the antibody molecule to give large numbers of monospecific fragments of variation. Since the association of the scFv-Fc fusions is degenerate, the second combinatorial parameter derives from the random re-assortment of the multiple binding domains (scFvs) of the antibody molecules themselves to give bispecific heterodimers. As used herein, the term bispecificity refers to the ability of the heterodimer to bind to two different sites within the same molecule (cis-reactivity) which differs from the way the term is usually used in immunochemistry where it refers to the potential to bind to two different molecules (trans-reactivity).

The antibody libraries and the selection schemes described herein can be readily employed and adapted for obtaining bispecific antibody modulators of any phenotype of eukaryotic cells, especially for selecting antibody modulators (e.g., agonists) of ligands that require obligate synergy in binding to their cognate cellular receptors and activating the corresponding signaling pathways. In addition to the anti-Epo bispecific antibodies exemplified herein, the bispecific agonist antibodies of the invention also include antibodies which are identified by morphology selection and which are capable of inducing stem cell differentiation (e.g., 12-1/12-2 bispecific antibody). To ensure re-assortment of multiple antibody chains (e.g., scFv chains) inside the same cell and production of bispecific antibodies for selection, the antibody-encoding viral vectors can be introduced into the producer cells with a slightly higher MOI. MOI is the number of transducing viral particles (e.g., lentiviral particles) per cell to be transduced. With high MOI transduction, both homodimeric and heterodimeric antibodies can be generated for functional selection. In some embodiments, an election scheme can entail testing of a range of MOI to obtain optimal antibody production and desired ratio of homodimeric/heterodimeric antibodies. Thus, when heterodimeric antibodies are primarily desired, the MOI used in the viral infection can be, e.g., around 2 or 3. Once the antibodies are introduced and expressed inside the producer cells or indicator cells, an appropriate assay corresponding to the phenotype for which antibody modulators are to be selected can be performed. Similar to selection of heterodimeric Epo antibodies as exemplified herein, indicator cell lines and phenotype assays for selecting bispecific antibody modulators for other phenotypes of a eukaryotic cell can also be obtained in accordance with methods routinely practiced in the art.

In addition to controlling MOI, certain modifications can be introduced into the antibody chains to promote heterodimer formation. For example, formation of heterodimers is facilitated by single residue substitutions such as T366Y and Y407T in Fc portion of the scFv-Fc fusion antibodies for EpoR as exemplified herein. The T366Y and Y407T Fc mutants prefer to form heterodimer because the larger side chain of Tyr366 in one IgG chain (Knob) can preferentially interact with the smaller side chain of Thr407 of the other antibody chain. Depending on the specific structure of the employed antibody library, other modifications may also be designed to enhance formation of heterodimers. For example, fusing scFv to leucine zipper Fos/Jun can facilitate production of bispecific antibody heterodimer

VII. Agonist Antibodies of Signaling Receptors or Surface Markers

As further exemplification, the invention provides antibodies or antigen-binding molecules that specifically bind to and modulate a cellular signaling receptor such as erythropoietin receptor (EpoR), thrombopoietin receptor (TpoR) and granulocyte colony stimulating factor receptor (G-CSFR). These agonist antibodies are capable of agonizing signaling activities mediated by the respective receptor, e.g., EpoR for mediating Jak2 phosphorylation and activation, stem cell proliferation or hemoglobin synthesis as described in the Examples below. General methods for preparation of monoclonal or polyclonal antibodies are well known in the art. See, e.g., Harlow & Lane, *Using Antibodies, A Laboratory Manual*, Cold Spring Harbor Laboratory Press, Cold Spring Harbor, N.Y., 1998; Kohler & Milstein, *Nature* 256:495-497, 1975; Kozbor et al., Immunology Today 4:72, 1983; and Cole et al., pp. 77-96 in Monoclonal Antibodies and Cancer Therapy, 1985. The specific agonist antibodies (e.g., anti-EpoR antibodies) disclosed herein were identified by selecting antibodies from a lentiviral vector based antibody library for activities in activating signaling pathway mediated by the respective receptor (e.g., EpoR). As detailed in the Examples below, some of the identified EpoR agonist antibodies are homodimeric antibodies, while others are heterodimeric bispecific antibodies. In addition to anti-EpoR functional antibodies, functional antibodies which are agonists of thrombopoietin receptor (TpoR) or granulocyte colony stimulating factor receptor (G-CSFR) are also provided in the invention.

Antibody agonists of the invention (e.g., the anti-EpoR functional antibodies) are preferably monoclonal antibodies like the antibodies exemplified in the Examples below. Preferably, they have the same binding specificities as that of the exemplified functional antibodies (e.g., E-1, V-1 and V-3 anti-EpoR antibodies, 3D9 and 14F12 anti-TpoR antibodies, the 3B3 anti-G-CSFR antibody, and the 9-3, 11-3 and 12-1/12-2 antibodies exemplified herein). These antibodies typically harbor variable region sequences that are the same or substantially identical to that of the exemplified antibodies. In addition to containing variable regions sequences derived from the exemplified antibodies, some agonist antibodies of the invention can also contain other antibody sequences fused to the variable region sequences. For example, the antibodies can contain the Fc portion of human IgG1 sequence (from hinge to $C_H3$) as described in the Examples herein. Further, various modifications can be introduced into the antibody sequences for desired properties. For example, to enhance formation of heterodimeric antibodies, the scFv-Fc fusions can harbor "Knobs-Into-Hole" $C_H3$ mutations (e.g., T366Y and/or Y407T mutations).

Some of the anti-EpoR agonist antibodies are derived from the specific homodimer scFv antibody (E-1) which comprises the heavy chain and light chain variable region sequence shown in SEQ ID NO:7 and SEQ ID NO:8, respectively. The CDR sequences of the heavy chain variable region of this antibody are GYTFTGYY (CDR1; SEQ ID NO:1), INPNSGGT (CDR2; SEQ ID NO:2), and CARLSSGWTFDYW (CDR3; SEQ ID NO:3). The CDR sequences of its light chain variable region are QSV-LYSPNNKNY (CDR1; SEQ ID NO:4), WAS (CDR2; SEQ ID NO:5), and CQQSYSLPFTF (CDR3; SEQ ID NO:6). Some other anti-EpoR agonist antibodies of the invention are derived from the specific heterodimeric scFv antibody (V-1/V-3) which comprises a first monomer (V-1) containing the heavy chain and light chain variable region sequences respectively shown in SEQ ID NO:21 and SEQ ID NO:22, and a second monomer (V-3) containing the heavy chain and light chain variable region sequences respectively shown in SEQ ID NO:23 and SEQ ID NO:24. The CDR sequences of the heavy chain variable region of the first monomer (V-1 monomer) are GGTFSSYA (CDR1; SEQ ID NO:9), IIPIFGTA (CDR2; SEQ ID NO:10), and CARDQGYYYGSGGLDYW (CDR3; SEQ ID NO:11). The CDR sequences of its light chain variable region are QSISSY (CDR1; SEQ ID NO:12), AAS (CDR2; SEQ ID NO:13), and CLQDYNYPLTF (CDR3; SEQ ID NO:14). The CDR sequences of the heavy chain variable region of the second monomer (V2 monomer) are GYTFTSYG (CDR1; SEQ ID NO:15), ISAYNGNT (CDR2; SEQ ID NO:16), and CARGVAAALSYW (CDR3; SEQ ID NO:17). The CDR sequences of its light chain variable region are SSDVGAYNY (CDR1; SEQ ID NO:18), EVT (CDR2; SEQ ID NO:19), and CISFTASSTWAF (CDR3; SEQ ID NO:20).

Some of the anti-TpoR agonist antibodies of the invention are derived from the 3D9 scFv antibody which is detailed in the Examples below. This scFv antibody has an amino acid sequence shown in SEQ ID NO:32. The sequences of the heavy chain and the light chain portions of the scFv are respectively shown in SEQ ID NOs:33 and 34. The CDR sequences of the heavy chain variable region of this antibody are RDTFNTYG (CDR1; SEQ ID NO:35), IIPIFGTA (CDR2; SEQ ID NO:36), and CARDRKLGGSDYW (CDR3; SEQ ID NO:37). The CDR sequences of its light chain variable region are QGLGRW (CDR1; SEQ ID NO:38), AAS (CDR2; SEQ ID NO:13), and QQSNSFPWT (CDR3; SEQ ID NO:39).

Some of the anti-G-CSFR agonist antibodies of the invention are derived from the 3B3 antibody exemplified in the Examples herein. This scFv antibody has an amino acid sequence shown in SEQ ID NO:40. The sequences of the heavy chain and the light chain portions of the scFv are respectively shown in SEQ ID NOs:41 and 42. The CDR sequences of the heavy chain variable region of this antibody are GGSISSGGYY (CDR1; SEQ ID NO:43), IYYSGST (CDR2; SEQ ID NO:44), and CARWNGVNNAFDI (CDR3; SEQ ID NO:45). The CDR sequences of its light chain variable region are QGISSW (CDR1; SEQ ID NO:46), AAS (CDR2; SEQ ID NO:13), and LQHNTYPFT (CDR3; SEQ ID NO:47).

Some agonist antibodies of the invention are derived from the specific antibodies which are capable of inducing differentiation of stem cells, antibodies 9-3, 11-3, 12-1 and 12-2. As detailed in the Examples below, these exemplified antibodies are identified via direct morphogenic selections of naive antibody libraries. Amino acid sequences of these four scFv antibodies are shown in SEQ ID NOS:48, 57, 66 and 75, respectively. The heavy and light chain variable region sequences of these antibodies are respectively shown in SEQ ID NOS:49 and 50 (antibody 9-3), SEQ ID NOS:58 and 59 (antibody 11-3), SEQ ID NOS:67 and 68 (antibody 12-1), and SEQ ID NOS:76 and 77 (antibody 12-2). The CDR sequences of the heavy chain variable region of antibody 9-3 are GFSFTTYG (CDR1; SEQ ID NO:51), ISSSSST (CDR2; SEQ ID NO:52), and ARGGDNSRGYYYIAGGDY (CDR3; SEQ ID NO:53). The CDR sequences of the light chain variable region of antibody 9-3 are SSIRY (CDR1; SEQ ID NO:54), DTS (CDR2; SEQ ID NO:55), and QEWSGYPYT (CDR3; SEQ ID NO:56). The CDR sequences of the heavy chain variable region of antibody 11-3 are GYTFTGYY (CDR1; SEQ ID NO:60), INPNSGGT (CDR2; SEQ ID NO:61), and ARGGPSYGDYFRWFDP (CDR3; SEQ ID NO:62). The CDR sequences of the light chain variable region of antibody 11-3 are HAVSSNS (CDR1; SEQ ID NO:63), GAS (CDR2; SEQ ID NO:64), and QQYGSSPPIT (CDR3; SEQ ID NO:65). The CDR sequences of the heavy chain variable region of antibody 12-1 are GFTFSSYE (CDR1; SEQ ID NO:69), ISSSGST (CDR2; SEQ ID NO:70), and AREVAAAGINDAFDI (CDR3; SEQ ID NO:71). The CDR sequences of the light chain variable region of antibody 12-1 are SSIRY (CDR1; SEQ ID NO:72), DTS (CDR2; SEQ ID NO:73), and QEWSGYPYT (CDR3; SEQ ID NO:74). The CDR sequences of the heavy chain variable region of antibody 12-2 are GYIFTSYD (CDR1; SEQ ID NO:78), IFPGEGST (CDR2; SEQ ID NO:79), and ARGDYYRRYFDL (CDR3; SEQ ID NO:80). The CDR sequences of the light chain variable region of antibody 12-2 are QDIDDD (CDR1; SEQ ID NO:81), EPT (CDR2; SEQ ID NO:82), and LQHGDFLTWT (CDR3; SEQ ID NO:83). In various embodiments, these antibodies derived from the 9-3, 11-3 or 12-1/12-2 antibodies can be used to induce differentiation of stem cells (e.g., human $CD34^+$ cells) in a lineage specific manner, e.g., to form dendritic cells.

A typical intact antibody interacts with target antigen predominantly through amino acid residues that are located in the six heavy and light chain complementarity determining regions (CDR's). The functional agonist antibodies of the invention (e.g., anti-EpoR antibodies) encompass antibodies or antigen-binding fragments having at least one of their heavy chain CDR sequences and light chain CDR sequences that is the same as or substantially identical to the corresponding CDR sequence of exemplified anti-EpoR, anti-TpoR, anti-G-CSFR or stem cell inducing antibodies (e.g., antibody 9-3). Some of the agonist antibodies of the invention have the same binding specificity as that of the exemplified antibodies disclosed in the Examples below. These antibodies can compete with the exemplified antibodies for binding to the respective receptor (e.g., EpoR). The antibodies can additionally possess the same or similar functional properties as that of the exemplified antibodies, e.g., anti-EpoR antibodies for agonizing EpoR signaling pathway. Some agonist antibodies of the invention are homodimers having all CDR sequences in their variable regions of the heavy chain and light chain respectively identical to the corresponding CDR sequences of the exemplified antibodies (e.g., the 3D9 anti-TpoR antibody, the 3B3 anti-G-CSFR antibody, or the anti-EpoR antibody E-1, V-1 or V-3). In other embodiments, the antibodies are heterodimers that have the three heavy and light chain CDR sequences respectively identical to that of the first monomer or the second monomer of the V-1/V-3 anti-EpoR heterodimeric antibody. Some other anti-EpoR antibodies are heterodimers with two monomers having heavy chain and light chain CDRs respectively identical to the CDR sequences of the two monomers of the exemplified V-1/V-3 bispecific antibody. In addition to their binding specificities, some of the agonist antibodies of the invention (e.g., anti-EpoR antibodies) are also functionally active in modulating (e.g., agonizing) the signaling activities mediated by the respective receptor (e.g., EpoR).

In addition to having CDR sequences respectively identical to the corresponding CDR sequences of an exemplified antibody (e.g., the E-1, V-1, V-3 or V-1/V-3 anti-EpoR antibodies, the 3D9 anti-TpoR antibody, the 3B3 anti-G-CSFR antibody or the 12-1/12-2 anti-integrin α3 antibodies), some of the agonist antibodies of the invention have their entire heavy chain and light chain variable region sequences respectively identical to the corresponding variable region sequences of the exemplified antibodies. In some other embodiments, other than the identical CDR sequences, the antibodies contain amino acid residues in the framework portions of the variable regions that are different from the corresponding amino acid residues of the exemplified antibodies. Relative to the exemplified antibodies, the agonist antibodies of the invention can undergo non-critical amino-acid substitutions, additions or deletions in the variable region without loss of binding specificity or effector functions, or intolerable reduction of binding affinity or receptor agonizing activities. Usually, antibodies incorporating such alterations exhibit substantial sequence identity to a reference antibody (e.g., the 3B3 anti-G-CSFR antibody, the 3D9 anti-TpoR antibody, anti-EpoR antibody E-1, V-1, V-3 or V-1/V-3, or anti-integrin α3 antibody 12-1 and 12-2) from which they were derived. For example, the mature light chain variable regions of some of the agonist antibodies of the invention have at least 75% or at least 85% sequence identity to the sequence of the mature light chain variable region of the exemplified antibodies. Similarly, the mature heavy chain variable regions of the antibodies typically show at least 75% or at least 85% sequence identity to the sequence of the mature heavy chain variable region of the exemplified agonist antibodies. In various embodiments, the antibodies typically have their entire variable region sequences that are substantial identical (e.g., 75%, 85%, 90%, 95%, or 99%) to the corresponding variable region sequences of the exemplified antibodies. Some agonist antibodies of the invention have the same specificity but improved affinity or receptor-agonizing activities if compared with the exemplified antibodies (e.g., 3B3, 3D9, E-1, V-1, V-3, 12-1 and 12-2).

VIII. Polynucleotides, Vectors and Host Cells for Producing Anti-EpoR Agonist Antibodies The invention provides substantially purified polynucleotides (DNA or RNA) which encode polypeptides comprising segments or domains of the receptor agonist antibody chains or antigen-binding molecules described herein. Some of the polynucleotides of the invention comprise the nucleotide sequence encoding the heavy chain variable region as shown in SEQ ID NO:25, 27 or 29 and/or the light chain variable region sequence as shown in SEQ ID NO:26, 28 or 30. Some other polynucleotides of the invention comprise nucleotide sequences that are substantially identical (e.g., at least 65, 80%, 95%, or 99%) to one of the nucleotide sequences shown in SEQ ID NOS: 25-30. When expressed from appropriate expression vectors, polypeptides encoded by these polynucleotides are capable of exhibiting antigen binding capacity.

Also provided in the invention are polynucleotides which encode at least one CDR region and usually all three CDR regions from the heavy or light chain of the agonist antibodies described in the Examples below. Some other polynucleotides encode all or substantially all of the variable region sequence of the heavy chain and/or the light chain of the exemplified antibodies. For example, some of these polynucleotides encode the amino acid sequence of the heavy chain variable region shown in SEQ ID NO:7, 21 or 23, and/or the amino acid sequence of the light chain variable region shown in SEQ ID NO:8, 22 or 24. Some other polynucleotides of the invention comprise a nucleotide sequence encoding the heavy chain variable region as shown in SEQ ID NO:33, 41, 49, 58, 67 or 76, and/or the light chain variable region sequence as shown in SEQ ID NO:34, 42, 50, 59, 68 or 77. Because of the degeneracy of the code, a variety of nucleic acid sequences will encode each of the immunoglobulin amino acid sequences.

The polynucleotides of the invention can encode only the variable region sequence of an agonist antibody. They can also encode both a variable region and a constant region of the antibody. Some of polynucleotide sequences of the invention nucleic acids encode a mature heavy chain variable region sequence that is substantially identical (e.g., at least 80%, 90%, or 99%) to the mature heavy chain variable region sequence shown in SEQ ID NO:7, 21, 23, 33, 41, 49, 58, 67 or 76. Some other polynucleotide sequences encode a mature light chain variable region sequence that is substantially identical to the mature light chain variable region sequence shown in SEQ ID NO:8, 22, 24, 34, 42, 50, 59, 68 or 77. Some of the polynucleotide sequences encode a polypeptide that comprises variable regions of both the heavy chain and the light chain of one of the exemplified anti-EpoR antibody. Some other polynucleotides encode two polypeptide segments that respectively are substantially identical to the variable regions of the heavy chain and the light chain of one of the exemplified antibodies (e.g., 3B3, 3D9, E-1, V-1, V-3 or 9-3).

The polynucleotide sequences can be produced by de novo solid-phase DNA synthesis or by PCR mutagenesis of an existing sequence (e.g., sequences as described in the Examples below) encoding an anti-EpoR antibody or antigen-binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458, 066. Introducing mutations to a polynucleotide sequence by PCR can be performed as described in, e.g., *PCR Technology: Principles and Applications for DNA Amplification*, H. A. Erlich (Ed.), Freeman Press, NY, N.Y., 1992; *PCR Protocols: A Guide to Methods and Applications*, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the receptor agonist antibodies described herein. Specific examples of lentiviral based vectors for expressing the antibodies are described in the Examples below (see FIG. 7). Various other expression vectors can also be employed to express the polynucleotides encoding the agonist antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat. Genet. 15:345, 1997). For example, nonviral vectors useful for expression of the anti-EpoR polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on lentiviruses or other retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an agonist antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an agonist antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted agonist antibody sequences. More often, the inserted agonist antibody sequences are linked to a signal sequences before inclusion in the vector. Vectors to be used to receive sequences encoding the agonist antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the agonist antibody chains can be either prokaryotic or eukaryotic. In some preferred embodiments, mammalian host cells are used to express and produce the antibody polypeptides of the present invention. For example, they can be either a hybridoma cell line expressing endogenous immunoglobulin genes or a mammalian cell line harboring an exogenous expression vector (e.g., the TF-1 cells or HEK293T cells exemplified below). These include any normal mortal or normal or abnormal immortal animal or human cell. In addition to the cell lines exemplified herein, a number of other suitable host cell lines capable of secreting intact immunoglobulins are also known in the art. These include, e.g., the CHO cell lines, various Cos cell lines, HeLa cells, myeloma cell lines, transformed B-cells and hybridomas. The use of mammalian tissue cell culture to express polypeptides is discussed generally in, e.g., Winnacker, *From Genes to Clones*, VCH Publishers, N.Y., N.Y., 1987. Expression vectors for mammalian host cells can include expression control sequences, such as an origin of replication, a promoter, and an enhancer, and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, EF1α and human UbC promoters exemplified herein, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transformation is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express the antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate for the cell type.

EXAMPLES

The following examples are provided to further illustrate the invention but not to limit its scope. Other variants of the invention will be readily apparent to one of ordinary skill in the art and are encompassed by the appended claims.

Example 1 Materials and Methods for Functional Selection of Agonist Antibodies

This Example describes some materials and methods employed in selecting Epo agonist antibodies.

Cell lines. The TF-1 cell line was maintained in RPMI 1640 (Gibco-Invitrogen) containing 10% fetal calf serum (FCS) (Gibco-Invitrogen), penicillin and streptomycin (Gibco-Invitrogen) and 2 ng/mL GM-CSF (R & D Systems). The HEK293T cell line was maintained in DMEM medium containing 10% FCS, penicillin and streptomycin (Gibco-Invitrogen). The HEK293F cell line was maintained in Freestyle 293 Expression Media with 4 mM Glutamax (Gibco-Invitrogen).

Construction of plasmids. The toolkit plasmids were constructed for making the lentiviral combinatorial antibody library and expression of the scFv-Fc fusion proteins. The relevant features of the plasmids are labeled in the vector maps shown in FIG. 7. All the vectors were designed so that the antibody genes could be exchanged between them with a simple SfiI digestion and ligation.

Construction of the lentiviral combinatorial antibody library. A pair of SfiI sites which are compatible with the phagemid vector were introduced into the lentiviral vector. Bacteria infected with phage were plated at 30° C. The phagemids were prepared directly from isolated bacteria.

The phagemids were digested with SfiI and the ~800 bp insert was ligated into the SfiI digested lentiviral vector.

Construction of the ScFv-Fc fusion expression vector. The genes encoding the scFv and the Fc portion of human IgG1 (from hinge to $C_H3$) were fused by overlap PCR and were cloned into the pFUSE protein expression vector (Invitrogen).

Engineering the "Knobs-Into-Hole" $C_H3$ mutants for bsAb expression. The $C_H3$ region of the immunoglobulin molecule containing mutated residues T366Y and Y407T were separately constructed in the scFv-Fc fusion expression vector. Mutations are denoted by amino-acid residue and number followed by the replacement amino acid.

Construction of the scFv-Flag expression vector. The oligonucleotides corresponding to flag tag were synthesized, annealed and ligated into the scFv-Fc expression vector to replace the Fc. To generate constructions containing the Thoseaasigna virus 2A (T2A) such that the EpoR and GFP could be cotranslated, the EpoR and T2A oligonucleotides encoding the peptide GSGEGRGSLLTCGDVEENPGP (SEQ ID NO:31) and GFP were assembled with overlap PCR and cloned into the lentiviral vector containing the UbC promoter.

Selection of EpoR binding antibodies from combinatorial antibody libraries in phage. Two protocols of panning were used. In the first, the combinatorial antibody scFv library in phage was selected in the first round on a EpoR ECD Fc fusion protein using magnetic protein G beads (NEB). In the second and third rounds phage were selected on EpoR ECD-his tag monomer protein using Nickel coated magnetic beads (Invitrogen) and were eluted with glycine-HCl (pH 2.2). In the second protocol, a combinatorial antibody scFv library displayed in phage was incubated with the EpoR ectodomain Fc fusion protein. The phage antibody-EpoR complex was captured with magnetic Protein G beads and unbound phage were removed by washing. Bound phage were eluted with either EPO or glycine-HCl (pH 2.2). XL1-blue cells were infected with the eluted phage and grown at 30° C. overnight. Bacteria were scraped from the plate and the helper phage VCSM13 was added to amplify phage for the next round of panning. Prior to the second and third rounds of panning, phage were pre-incubated with irrelevant human IgG1 to remove phage that bound to the Fc. The phage were selected on the EpoR ECD Fc fusion protein and bound phage were eluted with EPO only. 48 clones from each protocol were harvested and their ability to bind to the EpoR was analyzed by phage ELISA. The selected phagemids were sequenced by Sanger sequencing. Sequences were analyzed with Vbase2. Heavy chain CDR3s were aligned with Clustal X and a phylogenetic tree was constructed with Njplot.

Preparation of lentivirus. Virus was produced in HEK293T cells by co-transfection of lentiviral vectors with the pCMVD8.9 and pVSVg viral packaging vectors at ratio of 1:1:1. Supernatants containing virus were collected at 48 h post transfection. Cell debris was removed by centrifugation and filtering through 0.22 um PES membrane Filter Unit (Millipore). The titer of lentivirus prep was determined using Lenti-X p24 ELISAs (Clontech). The virus preparations were aliquoted and frozen at 80° C.

Transduction of TF-1 cells with lentivirus. Lentivirus was added to TF-1 cells in 1 mL medium containing 5 ug/mL polybrene and 2 ng/mL GM-CSF. The "Spinoculation" was performed by centrifugation of the lentivirus and cell mixture at 30° C. for 90 min at 1200 g. The cells were incubated with lentivirus overnight at 37° C. Excess virus was removed and fresh medium free of GM-CSF was added the next day.

Immunofluorescence staining. Cells were fixed with 4% paraformaldehyde (PFA) at room temperature for 20 min, blocked and stained with 1 ng/mL anti-human IgG1 Fc:PE antibody for 30 min at RT. Cells were also permeabilized with 0.1% Triton in PBS at RT for 20 min and incubated with anti-human IgG1 Fc:PE antibody for 30 min at RT. After washing in blocking solution three times for 15 min images were collected using a Zeiss inverted fluorescence microscope.

Selection of EpoR agonist antibody by a colony forming cell (CFC) assay using methylcellulose-based media. The wt hEpoR overexpressing TF-1 cells (TF-1/hEpoR) were transduced with the lentiviral antibody library at a multiplicity of infection (MOI) of 2. This MOI resulted in a 80% transduction efficiency as determined by immunofluorescence analysis with anti-human IgG1 Fc:PE antibody. The TF-1/hEpoR cells induced with the antibody library were added to methylcellulose media such that the methylcellulose final concentration was 1.27% and the cell concentration was approximately $3 \times 10^4$ cells/mL. 1.5 mL of cell suspension was added to 35-mm diameter dishes. The cells in soft agar were cultured for 2-3 weeks. The colonies were harvested with the aid of micromanipulator (model MM33A/L Sutter Instruments Company) and lysed with lysis Buffer containing Protease K for 1 h at 50° C. The antibody genes from each colony were amplified by PCR with primer pairs customized for our lentiviral vector. The PCR was carried out in a UV3 TEPA PCR cabinet (TSS inc.). The amplified antibody genes were analyzed by electrophoresis and recovered. After digestion with SfiI, the genes were ligated into the lentiviral vector and X1-1 blue bacteria were transformed. Four colonies selected from each bacterial transformation were sequenced with Sanger sequencing (Eton Bioscience or BATJ). The heavy chain CDR3 sequences were extracted by Vbase2.

TF-1 proliferation assay. TF-1 cells were washed with RPMI to remove any residual GM-CSF and plated in a 96 well microplate at $2 \times 10^4$ cells per well in RPMI1640 with 10% heat inactivated FBS. Conditioned medium from transfected HEK293T cells, purified antibodies or Epo at various concentrations were added and the wells were brought to a volume of 100 uL and incubated for 72 h at 37° C. 20 uL of MTS solution (CellTiter 96 Aqueous Non-Radioactive Cell Proliferation Assay, Promega) was added to each well. After 2 hours, the absorbance at 490 nm was measured.

Inhibition with an EpoR ectodomain. TF-1 cells were plated in microtitre wells at $2 \times 10^4$ cells per well in presence of 1 µg/mL BsAb and increasing concentrations of the truncated (Met 1-Pro 250) EpoR-Fc receptor. The cells were incubated for 72 h at 37° C. MTS solution was added to each well and the absorbance at 490 nm was measured after 2 hours.

Expression and purification of scFv-Fc fusion and scFv-flag proteins. For single antibodies, the antibody expression vector was transfected into HEK293F cells. For the BsAb, the knob-into-hole antibody pair plasmids were co-transfected into HEK293F cells. Antibodies from the pooled supernatants were purified using HiTrap Protein G HP Columns (GE) with AKTAxpress purifier. The vector encoding the scFv-flag tag fusion protein was transfected into HEK293F cells for transient expression. The scFv-flag was purified from culture media with an anti-Flag M2 affinity gel (Sigma-Aldrich) packed column under gravity flow. The buffer was exchanged to DPBS, pH 7.4 and stored at 4° C.

Phosphorylation Assay. TF-1 cells were starved in RPMI1640 medium containing 5% FBS and no GM-CSF for 24 h. $5 \times 10^6$ cells were used for each assay. Cells were treated at 37° C. for 30 min with RPMI serum-free medium containing 4 units/ml EPO 2 ng/mL GM-CSF or BsAb at various concentrations. The cells were washed once with ice-cold PBS containing 1× Halt protease and a phosphatase Inhibitor Cocktail and lysed on ice for 30 min with occasional vortexing in 500 ul of Pierce IP lysis buffer containing 2× Halt Protease and the phosphatase inhibitor cocktail. Cell debris was removed by centrifugation at ~13,000 g for 10 minutes. The phosphorylation status of STAT-5 was determined by Western blot analysis of the cell lysates using anti-phospho STAT-5 (Tyr694) antibody (Cell Signaling Technology, Cat #9356) and the amount of protein in the gel bands was quantitated using anti-total STAT-5 antibody (Cell Signaling Technology, Cat #9363). The other half of the cell lysates were incubated overnight at 4° C. with 2 µg of anti-JAK2 antibody (Santa Cruz Biotechnology, cat #HR-758) per sample to form immune complexes. The antigen-antibody complexes were captured with Protein A/G magnetic beads after incubation for 1 hour at RT. After 3 washes, the immune complexes were eluted with Low-pH Elution Buffer (Pierce, Cat #88804). The immunoprecipitates were analyzed by Western blots that were probed with anti-phosphotyrosine antibody (clone 4G10 Millipore Cat #05-321X) and the amount of protein in the gel bands was quantitated with anti-total JAK2 antibody.

TF-1 cell differentiation assay. TF-1 cells were cultured for at 37° C. for 2 weeks in the presence of 0.1 ng/mL of GM-CSF plus EPO. (4 IU/mL) or various concentrations of the BsAb. The color of the pelleted cells was observed. The cells were then lysed in RIPA and expression of hemoglobin was analyzed by Western blotting using anti-hemoglobin antibodies.

Erythroid colony formation from human hematopoietic stem cells. CD34+ stem cells were isolated from human bone marrow using a direct immunomagnetic CD34 Micro-Bead labeling system (All Cells, Cat #ABM010). CD34+ cells in Iscove's MDM with 2% FBS (Stem cells biotechnology, cat #07700) were diluted 1:10 in 3 mL Methocult methylcellulose medium (Cat #H4230, Stem Cell Technologies) supplemented with 50 ng/mL rh-SCF, 20 ng/mL rh-IL-3 and 20 ng/mL rh-IL-6 in the presence of EPO (4 IU/mL) or different concentrations of the BsAb. 3000-4000 cells were plated in duplicate in 35 mm dishes and colony formation was scored at day 14.

Kinetic characterization using bio-layer interferometry (BLI). Experiments were performed using the Octet Red (Fortebio Inc.). The scFv Fe fusion proteins were captured with anti-Human IgG Capture (AHC) Biosensors (kinetics grade Cat #18-5060). A titration series of the purified EpoR ectodomain monomer protein was measured against the immobilized scFv Fc in the association/dissociation cycle. The data set was fit to a 1:1 binding model to determine ka, kd and Kd.

Example 2 Isolation of EpoR Binding Antibodies from a Combinatorial Library

Figure 1:
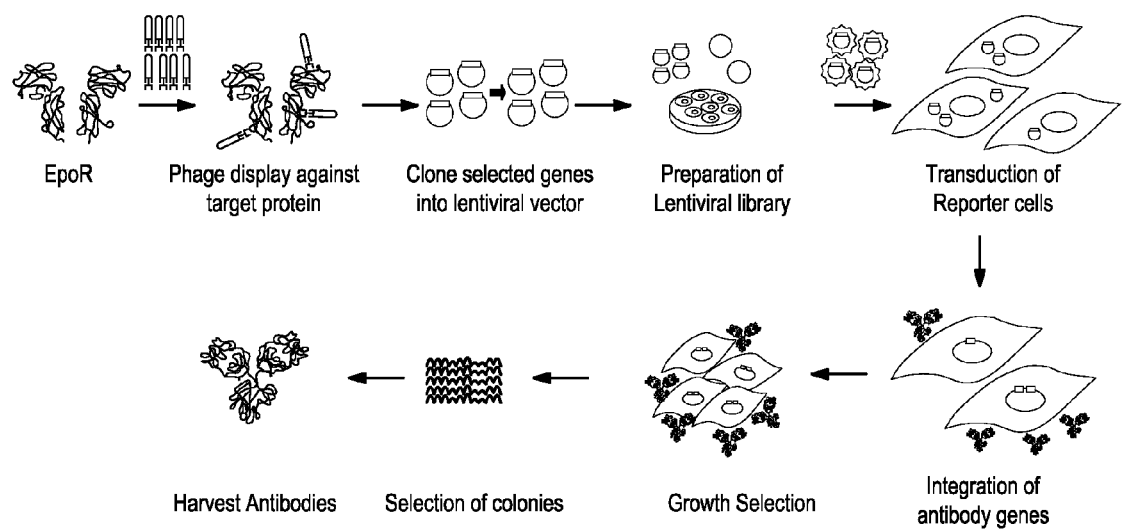
FIG. 1 is a scheme for selection of antibody agonists from combinatorial libraries. Antibodies that bound EpoR were selected from a combinatorial antibody library displayed in phage by affinity-based selection. The antibody genes from the selected phage were cloned into lentiviral vectors to allow phenotypic selections after infection of eukaryotic cells and integration of the antibody genes into the genome. The transduced cells were plated in methylcellulose agar such that the secreted antibodies were trapped around the cells producing them. The colonies that formed were harvested using a micromanipulator and the antibody genes were recovered by PCR. The PCR products were cloned and sequenced and the respective antibodies or antibody combinations were tested for their activity. The active antibodies were expressed in mammalian cells and purified for further characterization.
Figure 7:
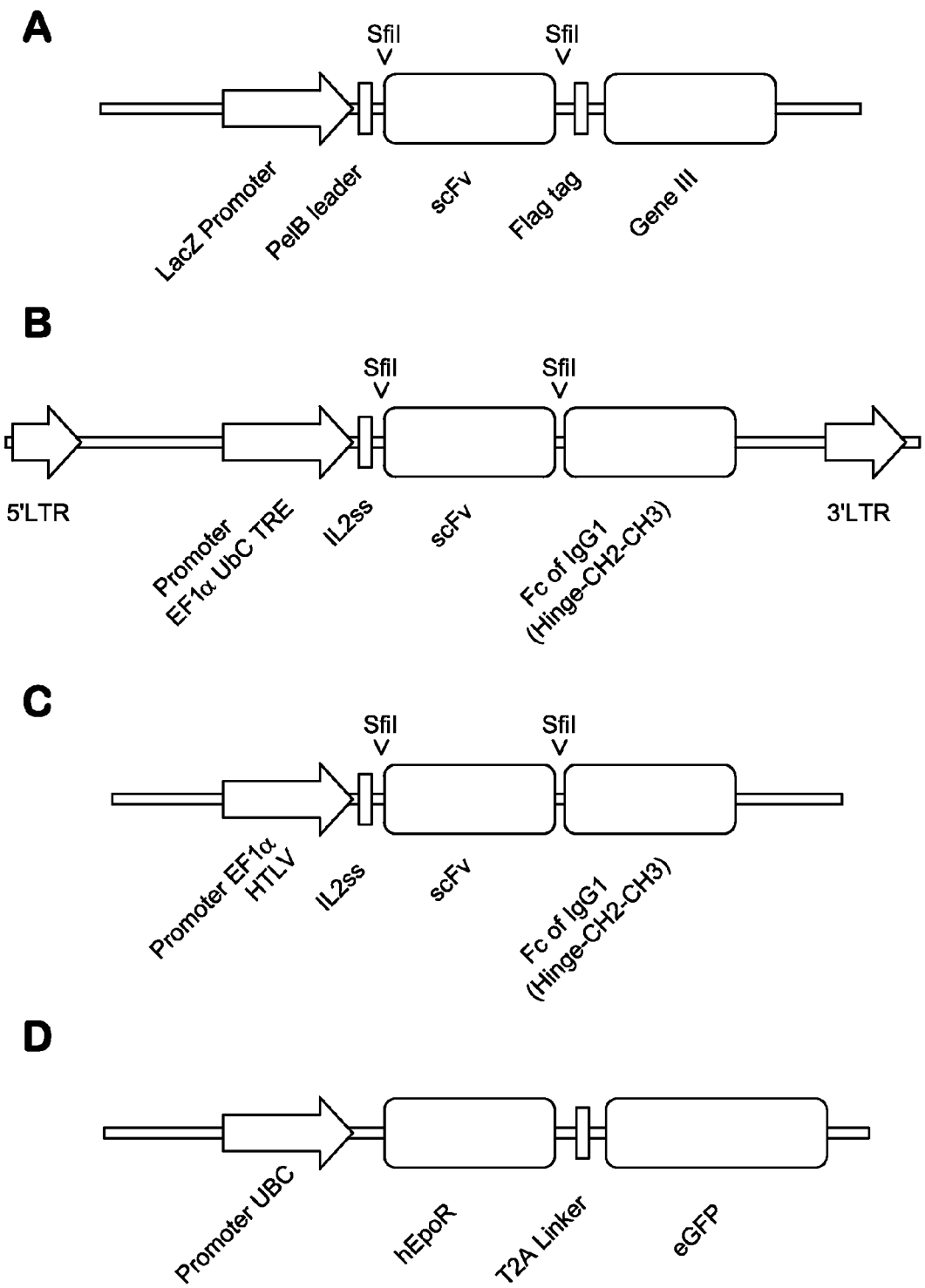
FIGS. 7A-7D show a schematic illustration of the structure of the toolkit plasmids constructed for expressing svFv-Fv fusion proteins. (A) Phagemid vector. (B) Lentiviral plasmid with optional promoters and the gene encoding the IL2 signal peptide as a secretory signal sequence. The gene encoding the scFv is fused to that encoding the Fc portion of IgG. (C) Mammalian expression plasmid with scFv fused to Fc. (D) Lentiviral vector co-translating hEpoR and GFP by T2A-mediated ribosomal skipping.

The initial goal of the method was to express as large an antibody library as possible inside eukaryotic cells where the antibodies can either be contained in the cytoplasm or secreted. To accomplish this in a way that gives the greatest degree of freedom, we used both M-13 phage and lentivirus vectors that were constructed so that the antibody genes could be easily interchanged (FIG. 7). In general there are two approaches to this problem that depend on whether the target is known. One could use either conventional panning of a combinatorial antibody library in phage to enrich for antibodies against the target proteins and then switch the selected genes into lentiviruses or we could use the lentivirus library directly without prior selection (FIG. 1). Initial selection in phage is optimal when the target is known because phage systems can interrogate a much larger diversity space (approx. $1.0 \times 10^{11}$) than is possible in eukaryotic systems. However, when little is known about the molecular components of a pathway, direct phenotypic selection in eukaryotic cells is the preferred option. In the experiment reported here, one already knew that the Erythropoietin receptor (EpoR) is the target of Erythropoietin (EPO) and, thus, we first selected antibodies that bound to the EpoR from combinatorial libraries in phage. Since, it may be critical to select antibodies to the correct configuration of the EpoR, only panning in solution was attempted. The target proteins were an EpoR dimer constructed as an Fc fusion or His-tagged monomeric EpoR. Two different protocols were used. The first protocol (P1) was designed to address epitopes that were not directly competitive with the EPO binding site but were still accessible in the dimer. The first two panning rounds alternated between the EpoR dimer-Fc fusion and the His-tagged monomeric EpoR. These rounds were followed by a third round that used the monomeric EpoR to eliminate any residual phage that targeted the Fc region of the construct. Glycine-HCl (pH 2.2) was used to elute bound phage. Thus, in the first round all antibodies that that bound to the EpoR dimer Fc-fusion protein were selected and in the second round the pool was narrowed to eliminate antibodies whose reactivity was dependent on the Fc-fusion partner. In the second protocol (P2) phage attached to the EPOR dimer Fc-fusion were collected on protein G beads after which specific elution with EPO was carried out. This protocol was used to enrich for antibodies that bound at or near the EPO binding site of the EpoR. To sample the results of the panning, 48 clones from each protocol were randomly picked for phage ELISA using adsorbed His-tagged monomeric EpoR as the antigen. About half of the clones from each procedure bound specifically to the EpoR relative to nonspecific binding to BSA. There was a spectrum of reactivity as determined by phage ELISA. Sequence analysis of the reactive clones showed that they could be arranged into 21 different families. In some cases the same antibodies were selected using both protocols whereas in others the selected antibodies were from only one protocol (P1 versus P2).

Example 3 Selection of Agonist Antibodies

Figure 2:
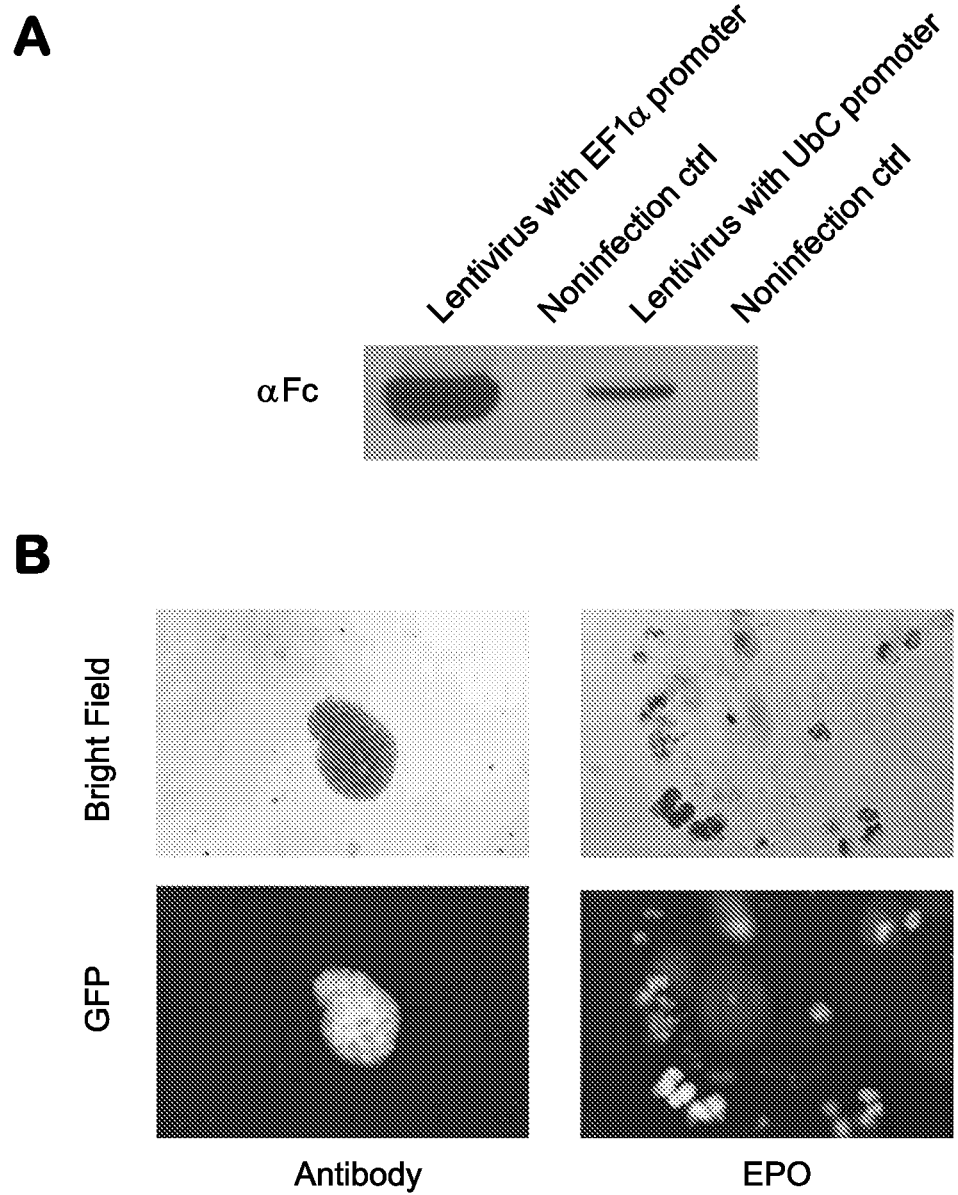
FIGS. 2A-2B show selection of agonist antibodies. (A) Western blot analysis showing that EF1α is a much stronger promoter for antibody synthesis than the UbC promoter. Therefore, lentiviral vectors with EF1α promoters were used in all further experiments. The TF-1 cells co-transduced with hEpoR-T2A-GFP and antibody libraries were cultured in cytokine free methylcellulose agar for 2-3 weeks. (B) Colonies are shown where either bright field microscopy to study the morphology and the color of the colonies or fluorescence microscopy to monitor the expression of the EpoR were used. TF-1 cells transduced with the EPO gene were used as positive controls. The colonies whose growth was independent of EPO were harvested with a micromanipulator. To produce antibodies, single antibody genes from the selected cell colonies were transfected into HEK293T cells.

The genes encoding the antibodies that bound to the EpoR that were selected in phage by each protocol were transferred separately to lentiviruses which were used to infect TF-1 cells that we had engineered to overexpress the wild type EpoR. Expression of wild type EpoR (wt EpoR) in TF-1 cells is a necessary complement to their endogenous truncated EpoR for sustained cell growth. To facilitate study of the expression of the EpoR, the wt EPOR and GFP were linked with a T2A linker (FIG. 7). The expression of antibodies in the cells infected with lentiviruses, using either the EF1α or the UbC promoter, was analyzed by western blot analysis (FIG. 2A). The amount of antibody expressed was higher with the EF1 α promoter. (FIG. 2A).

The human TF-1 cells that we engineered to express wt EpoR required EPO for growth. To determine if any expressed antibodies could substitute for EPO, infected and control cells were plated in EPO-free soft agar and observed after 14 days for growth of red colonies (FIG. 2B). Only the cells infected with viruses that encoded antibodies yielded red colonies (FIG. 2B). The fact that a control vector that only encoded GFP did not induce growth of any colonies showed that the observed colony growth was not the result of insertional mutagenesis induced by integration of the lentiviral genome. Whereas authentic EPO induced growth in most of the plated cells, growth of cells containing only antibody genes was much less frequent even though more than 80% of cells were infected. Thirty-three colonies from infected cells were picked and the antibody genes were recovered by PCR and cloned into the lentiviral vector (FIG. 7). The genes encoding the antibody CDR3 regions were analyzed to determine the number of different sequences in a given clone. This analysis showed that between one and four different lentiviruses were recovered from each colony. Since the initial sequencing of the antibody genes isolated from phage that bound to the EpoR was only a sampling of the available diversity, some new sequences were found in the clones that were selected by lentivirus infection.

Similar experiments were performed to select agonist antibodies of thrombopoietin (Tpo). Following expression of the antibody library in a Tpo reporter cell line constructed with a chimeric receptor encoding a fluorescent marker, Tpo-mimicking antibodies were selected via fluorescence-activated cell sorting. See below for detail.

Example 4 Epo Agonizing Activity of Selected Antibodies

Figure 3:
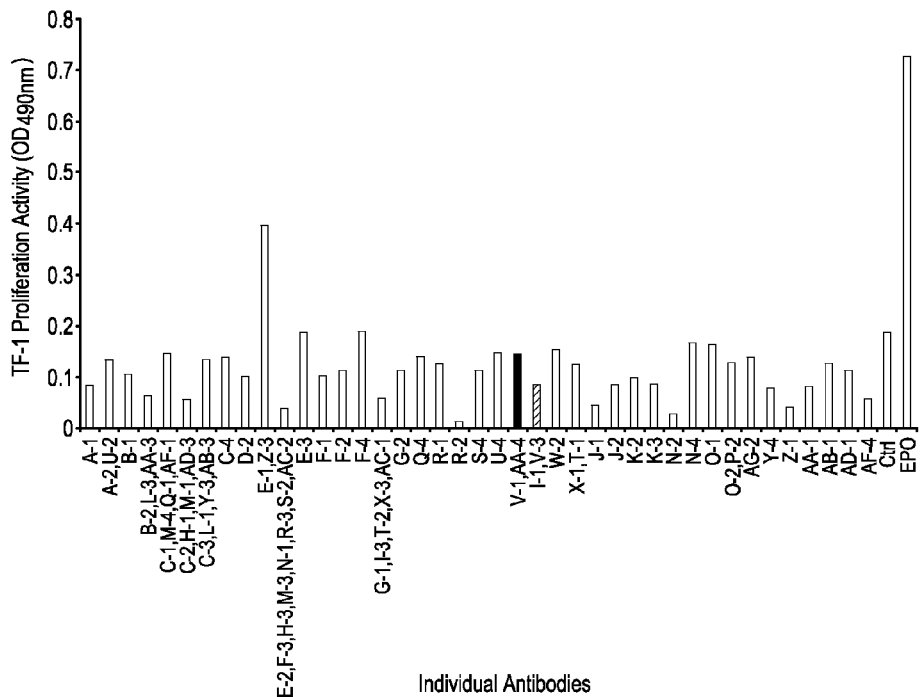
FIGS. 3A-3B show antibody synergy from transfections. (A) The ability of the individual antibodies to induce TF-1 cell proliferation was tested using the conditioned medium from HEK293T cells 48 h post-transfection. The TF-1 cells were mixed with an equal volume of conditioned medium in micro-titer wells and cultured in absence of EPO for 72 h. The number of viable cells was determined by an MTS assay. Antibody E-1 was the strongest agonist with about 60% of the activity of authentic EPO. (B) To study synergy, combinations of two different antibody genes isolated from the same colonies were transfected into HEK293T cells. TF-1 cell proliferation was tested using conditioned medium obtained 48 h post-transfection. The TF-1 cells were mixed with an equal volume of conditioned medium and cultured without EPO for 72 h. The number of viable cells was determined by an MTS assay. Co-transfection with the V-1/V-3 genes gave the strongest activity that was equal to that of EPO.
Figure 3:
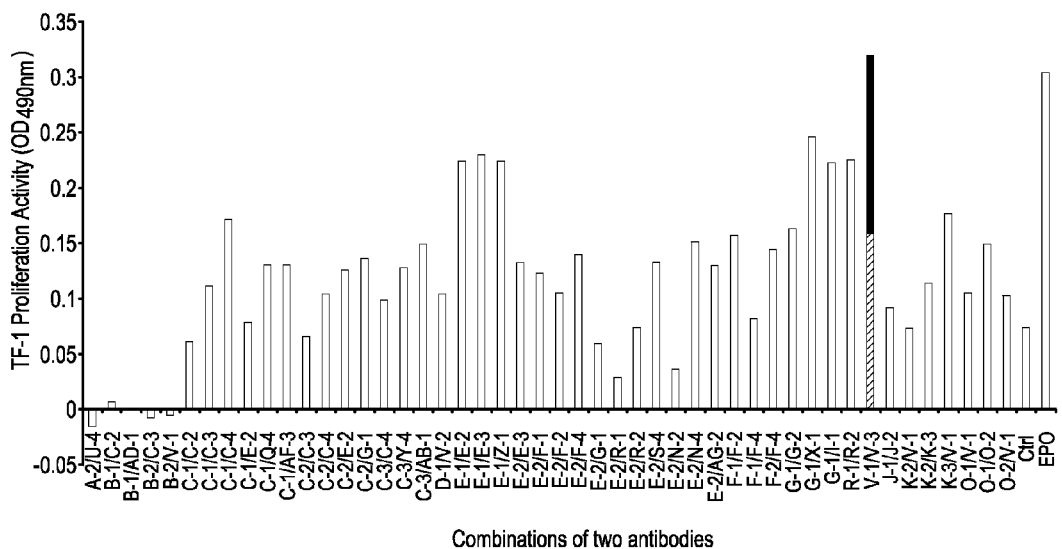

The antibodies encoded by the lentiviruses were produced by transient transfection of HEK-293T cells and tested for their ability to induce proliferation of TF1 cells. Two antibodies were active EpoR agonists, which had around 60% of the activity of authentic EPO. Although they are harvested from the different colonies at different days, they have the same sequence (FIG. 3A).

Example 5 Obligate Bispecificity of Selected Epo Agonist Antibody

Since many clones expressed more than one antibody, there was the possibility that the observed agonist activity was dependent on the synergy between different antibody specificities. To test this idea, conditioned medium of HEK293T cells transfected with two antibodies originated from the same colonies were observed for their cell proliferation by an MTS assay. For example, for colonies that had antibody sequences A, B, and C, the co-transfected pairs included sequences AB, AC, and BC. A total of 49 combinations were tested (FIG. 3B). Some of these combinations gave markedly enhanced agonist activity that in one case (V-1/V-3) was as strong as authentic EPO (FIG. 3B).

There are two possible routes to these synergistic effects. In one scenario two different homodimeric antibody molecules could be simply additive in effect. However, because of the format used here where the scFvs are fused to the Fc fragment of the immunoglobulin molecule there is the alternate possibility that heterodimers will be formed in a cell that expresses more than one antibody.

Figure 4:
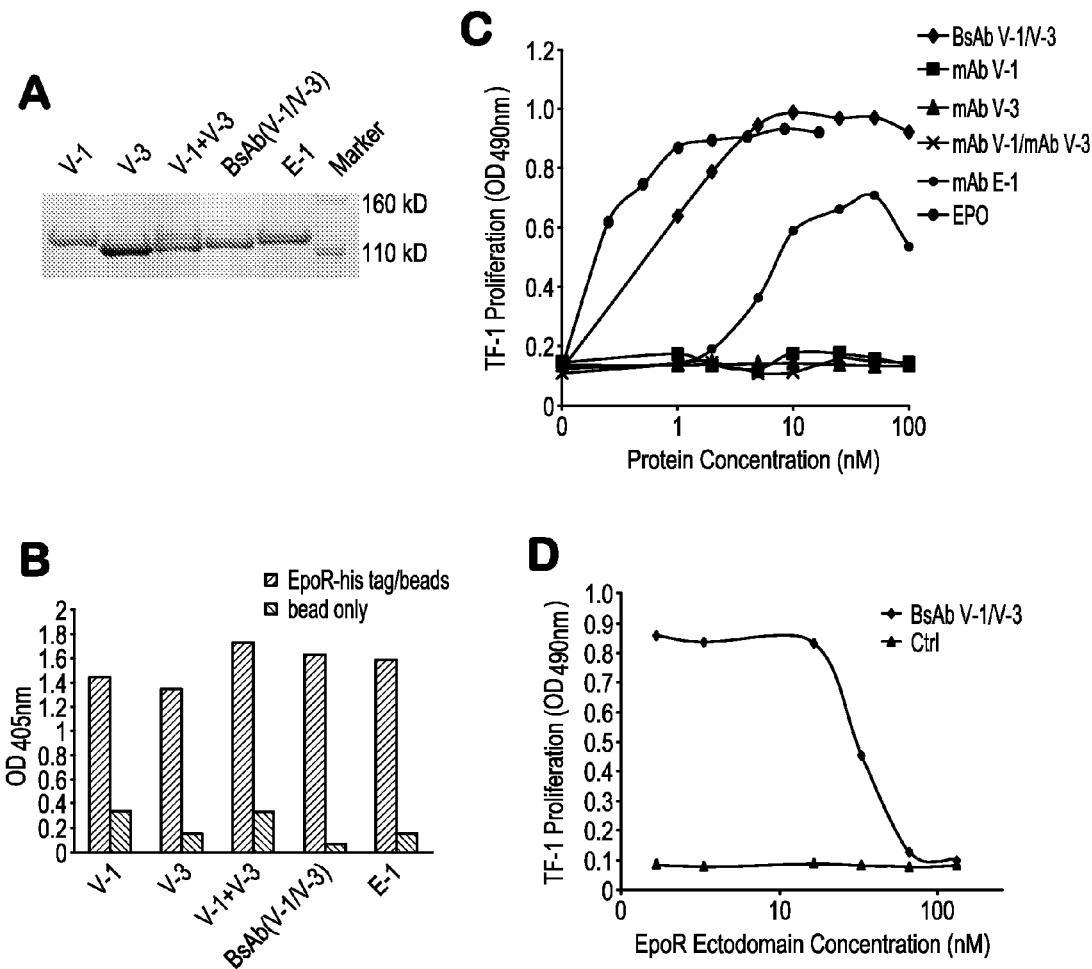
FIGS. 4A-4D show synergy in antibody protein constructs. The single antibodies V-1 and V-3 and the bispecific antibody V-1/V-3 (BsAb) that were generated using "Knob-into-Hole" technology were purified from HEK293F cells. (A) The purified proteins were analyzed using 7% Tris-Acetate gels with TA running buffer. (B) Antibody binding to the EpoR was tested by a "pull down" experiment. Different antibodies were mixed with the extracellular domain of hEpoR-his tag. The complexes were captured with His-tag Dynabeads and bound antibodies were detected with an anti-Fc:HRP antibody. (C) The dose response curve for the abilities of the heterodimeric BsAb and the homodimeric antibody E-1, the most potent single antibody (FIG. 3A) to stimulate the proliferation of the EPO-dependent TF-1 human erythroleukemic cells. The maximum response of the BsAb is equal to EPO showing that it is a full agonist while the strongest homodimeric antibody E-1 showed only 60% of the maximum response generated by authentic EPO. (D) To show that the purified EpoR ectodomain Fc chimera inhibits the antibody agonist activity, TF-1 cells were treated with antibodies at a concentration of 10 nM in presence of increased concentrations of the EpoR ectodomain Fc fusion protein.

To determine the molecularity of the observed synergy, we studied whether the two different binding specificities had to be present in the same immunoglobulin molecule. To purify the possible antibody combinations, cells were transfected with an expression vector encoding either a homodimeric antibody or a heterodimer whose partners were dictated by "knob in hole" engineering of the Fc fragment (Ridgway et al., Protein Engineering 9:617, 1996). The "knob in hole" engineering promotes heterodimer formation by introducing respectively a T366Y mutation and a Y407T mutation into the $C_H3$ region of the Fc portion of the two different monomers. Fortunately, the potential antibody partners had slightly different sizes so that the purity of the "knobs into hole construct" after protein G chromatography could be confirmed by acrylamide gel analysis (FIG. 4A). Although all of the purified antibodies bound to the EpoR (FIG. 4B), neither the individual antibodies nor simple mixtures of two different antibodies had any agonist effect (FIG. 4C). However, when the two specificities were combined in a single antibody molecule, the protein had strong EPO like activity that is equivalent to that seen when multiple antibody species were generated inside cells by co-transfection (FIG. 4C). The maximum response of the bispecific heterodimeric antibody and EPO were similar (FIG. 4C). Importantly, the heterodimeric bispecific antibody (V-1/V-3) was a full agonist, unlike any of the homodimeric antibodies; notwithstanding the fact that one of the homodimeric antibodies (antibody E-1) did show a maximum agonist effect of about 60% (FIG. 4C). The specificity of the agonist effect was confirmed by showing that it could be completely inhibited by the purified EpoR ectodomain (FIG. 4D). Furthermore, the binding specificity of the anti-EpoR antibodies was confirmed by showing that they did not react with other proteins including the thrombopoietin receptor.

Figure 5:
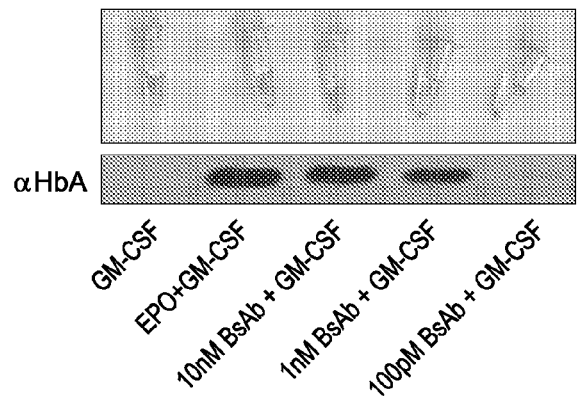
FIGS. 5A-5C show activation of the EpoR signaling pathway. (A) TF-1 cells were maintained in suboptimal concentration of GM-CSF (0.1 ng/mL) plus EPO or the BsAb at various concentrations for 1 week. Cells were pelleted and lysates were analyzed for the production of hemoglobin by observation of the color of the pellets and Western blots that were probed with anti-hemoglobin antibodies. (B) To study the induced phosphorylation of JAK2 and Stat5, cytokine-depleted TF-1 cells were treated with 2 ng/mL GM-CSF, 4 IU/mL EPO or the BsAb for 30 min at 37° C. Unstimulated cells were used as a control. Half of the cell lysate was subjected to immunoprecipitation (IP) with anti-JAK2 antibody, followed by Western blot analysis (WB) with anti-phosphotyrosine antibody (B). After striping the film, the total amount of JAK2 in the gel bands was detected with anti-JAK2 antibody. Western blot analysis of the other half of the cell lysates was carried out using antibodies against phospho-Stat5 (Tyr694) and Stat antibodies. The experiments were carried out on both TF-1 cells (left) or engineered TF-1 cells complemented with wt hEpoR (right). (C) The BsAb induced erythroid differentiation of human stem cells. Human CD34+ hematopoietic stem cells freshly isolated from bone marrow were incubated for 14 days with the BsAb or Epo incorporated in soft agar. Typical red CFU-E colonies are shown.
Figure 5:
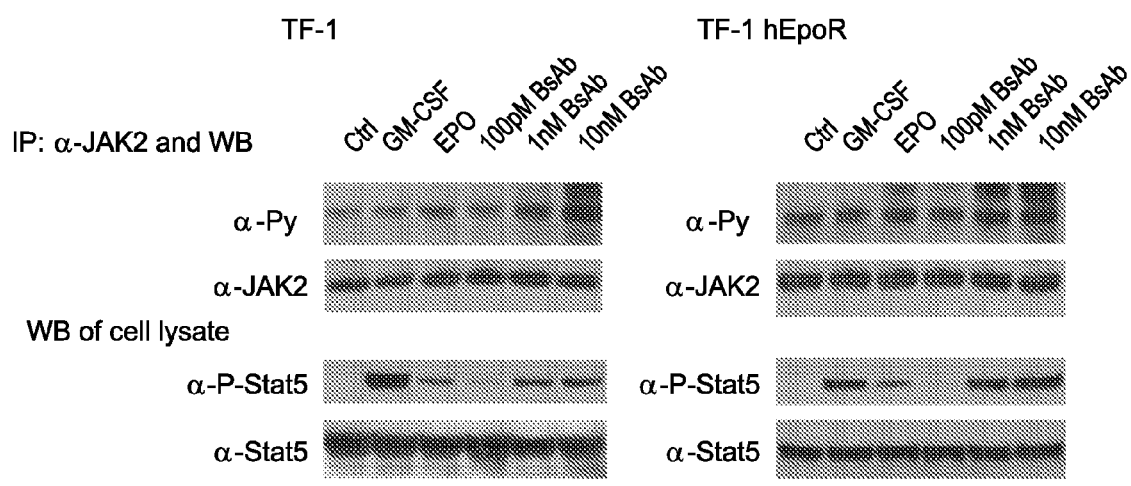
Figure 5:
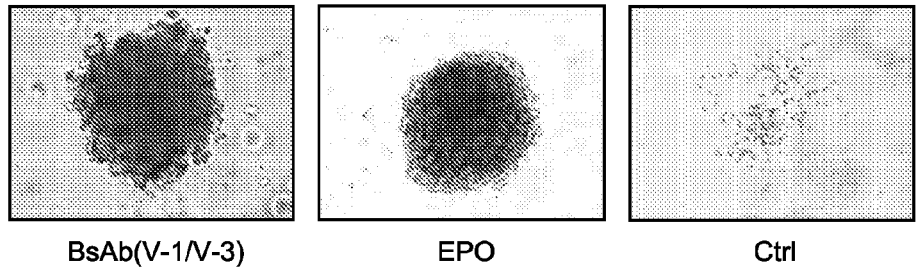

To confirm the agonist activity of the various antibody constructs, their ability to induce hemoglobin synthesis and protein phosphorylation was studied in TF-1 and TF-1 wtEpoR cells (FIGS. 5A-5B). The heterodimeric bispecific antibody induced hemoglobin synthesis (FIG. 5A) and much greater phosphorylation of JAK-2 and STAT-5 than either EPO or GM-CSF, themselves (FIG. 5B). Since GM-CSF is required for maintenance of TF-1 cells, its effects on phosphorylation of JAK-2 and STAT-5 were also studied as an additional positive control (FIG. 5B).

Example 6 Asymmetric Cooperativity of Selected Epo Agonist Antibody

A biolayer interferometry analysis of the binding parameters of the component antibodies showed that each bound to the EpoR where V-1 had an affinity of 26 nM compared to 45 nM for V-3. Authentic EPO competed with antibody V-3 but not V-1 for binding to the EpoR, demonstrating that only one of the antibodies bound in the vicinity of the EPO binding site whereas the other bound elsewhere. Thus, both EPO and the bispecific antibody achieve the obligatory asymmetric binding to the EpoR that is necessary for full agonist activity, albeit in different ways. In the case of EPO, asymmetry is achieved by the use of two distinct interfaces (site 1 and site 2) that bind with different affinities to a single site in the homodimeric EpoR (Watowich, J. Invest. Med. 59:1067, 2011). By contrast, the heterodimeric bispecific antibody achieves asymmetry by using its two different binding specifies to interact with different sites on the EpoR (FIG. 6).

To determine the nature of the binding cooperativity between the two different specificities, a competition experiment was designed that allowed study of the effect that each antibody had on the binding of the other to an EpoR monomer. Thus, competition between an unlabeled scFv-flag fusion and a biotinylated scFv-flag fusion could be monitored with HRP-labeled streptavidin to measure the effect of the binding of one antibody on the off rate of the other. As expected, the homodimeric antibody pairs with the same specificity in each arm of the dimer competed with each other. This finding is in striking contrast to the results for the homodimeric pairs with different specificities that did not compete with each other, again confirming that they bound to different regions of the EpoR. This result also indicates that the two different antibodies were not allosteric partners.

Example 7 Induction of Human Bone Marrow Stem Cells

The TF-1 cells that we studied here are widely used to assay for activities a variety of cytokines (30). However, as a cell line they might not be faithful representatives of the actual red cell progenitors in the bone marrow. Thus, we wanted to demonstrate that our agonist antibodies induced erythropoiesis from human bone marrow hematopoietic stem cells. The bispecific agonist antibodies were used to stimulate CD34+ stem cells that were freshly isolated from human bone marrow. After one week, cell proliferation and hemoglobin synthesis were already evident (FIG. 5C). To put the results on a more quantitative basis, the number of induced colonies was counted after 14 days. It was found that authentic EPO and the bispecific antibody induced approximately the same number of colonies.

Example 8 Selecting Thrombopoietin (Tpo) Agonist Antibodies

This Example describes selection of antibody agonists that are complete thrombopoietin phenocopies. The antibodies were selected directly for activation of cellular pathways, rather than cellular replication. As detailed below, the selection scheme utilized a fluorescent reporter system that operates at the level of single cells. The reporter system is based on activation of signaling pathways, and allows one to select directly in a matter of weeks antibody agonists that engage all the downstream pathways activated by authentic Tpo. Because there is co-packaging of the genes encoding the candidate agonist molecules with their targets, each cell is a selection system unto itself.

Construction of a Chimeric TpoR Reporter System:

One could study potential antibody agonists using growth of cells expressing the wtTpoR as the selectable parameter. However, such a system is not as robust as one would like because the number of selectable events that can be interrogated does not match the vast number of potential input events from the library. Also, such selections can be confounded by high backgrounds caused by the appearance of mutant cells that have sustained cellular proliferation in vitro in the absence of an agonist. To increase the number of observable events, we constructed a fluorescent reporter system that allowed screening at the level of single cells. Two reporter cell lines that were responsive to Tpo were constructed starting with HEK293T cell lines that contain an integrated beta-lactamase gene under control of the Sis-inducing element (SIE) promoter sequence. These HEK293T (Sie-bla) cells can be activated by IL6 via the Jak-Stat signaling pathway. Unfortunately, Tpo does not activate the nascent fluorescent reporter system in these cells even when the wild type Tpo receptor (TpoR) is introduced into them. To overcome this problem, we constructed chimeric receptors by splicing the TpoR ectodomain to the IL6st (gp130) signal transducing intracellular domain at two different crossover points. In one case, the ectodomain of the TpoR from the N-terminus to the box I region (amino acids 1-527) was linked to the IL6st signal transducing intracellular domain from after the box I region to the C-terminus (amino acids 651-918). Alternatively, the TpoR ectodomain from the N terminus to before the transmembrane helix (amino acids 1-491) was linked to the IL6st domain from the trans-membrane helix to the C-terminus (amino acids 605-918). When Tpo binds to the TpoR ectodomain of these chimeric receptors, their intracellular IL6 signal transduction component should be engaged leading to activation of a pathway that can be detected by generation of a unique FRET based fluorescent signal. Indeed, cells containing these chimeric receptors were now responsive to Tpo as determined by flow cytometry, analysis of the OD460 nm-to-OD530 nm ratios in cells, and fluorescent microscopy of transduced cells. Cells expressing the signal could be easily selected by fluorescence activated cell sorting (FACS), thereby allowing selective recovery of activated clones. The first construction gave the strongest fluorescent enhancement, indicating that the box 1 element is important for efficient signal transduction and it was used for further experiments.

Validation of Single Cell Formats:

Because we wished to use a single cell selection format, two strategies were used to confine the antibodies to the cells that produced them. In one, the cells were coated with a thin layer of agar to limit diffusion of antibodies to neighboring cells. In the other, the endoplasmic reticulum (E.R.) retention signal peptide Lysine-Glutamic acid-Aspartic acid-Leucine (KEDL) was appended to the C-terminus of the antibody molecule so that it was retained in the E.R. lumen.

Antibody candidates in phage were selected initially for their ability to bind to the purified TpoR by two rounds of panning. The selected antibodies were characterized by phage ELISA followed by nucleic acid sequencing of a sampling of the positive clones. Twenty-two sequences were recovered. Out of these, two different sequences were found to be repeated 3 and 9 times respectively, indicating a strong enrichment parameter.

To select for antibodies that were agonists, antibody genes from the entire enriched population of the selected phage were transferred to lentiviral vectors for infection of reporter cells. Because the antibody genes are integrated into the genome, each candidate antibody remains linked to a single reporter cell. Prior to analysis of the antibody library, the optimal time for observing induction of the signal after exposure to the FRET substrate was determined by a kinetic analysis. Specifically, the cells expressing the chimeric receptor were transduced with the lentiviral antibody library that contained genes that were recovered from phage after Tpo or Glycine Elution from the TpoR. At different time points after the transduction, the cells were collected and FRET substrate was loaded. The cells were analyzed with Flow cytometry. Non-treatment or Tpo treatment was used as a negative or positive control. The maximum 460 nm emission was observed at around 20 h and disappeared by 48 h.

Sixteen hours after infection with the antibody library in its secretory format, the reporter cells were incubated with the FRET substrate and sorted by flow cytometry. The induction frequency of cells that were infected with antibodies that were selected after two rounds of panning against the TpoR was compared to that of cells infected with a naive unselected library. Authentic Tpo served as a positive control. As expected, antibodies that were pre-selected on the TpoR induced far more cells than those from the unselected library.

Individual fluorescent cells were deposited into microtiter wells and grown to confluence. The growth media harvested from these clones was used to test which ones produced active antibodies as determined both by proliferation of cells containing the wtTpoR and generation of fluorescence in the reporter cells containing the chimeric receptor. There was a strong positive correlation for the two assays. It should be noted that although the cell proliferation assay is not robust for selections, it is a useful assay once a candidate agonist is obtained. The antibody genes from the selected cell clones that were producing active antibodies were recovered by PCR and cloned into the pFUSE mammalian expression vector for sequencing. The majority of clones carried a single sequence that, remarkably, was repeated in many different clones. As seen earlier in our studies of the EPO system, some clones had more than one sequence, consistent with the multiplicity of infection used.

The system would be most useful if active antibodies that are present in a variety of sub-cellular compartments could be selected. To test this, one agonist antibody (3D9) was constructed in both the secretory and E.R. retention formats. The intracellular confinement of antibodies that carried the retention signal was confirmed by analysis of the growth medium and cell lysates from cells producing it. The antibody with an E.R. retention sequence was present at high concentration in the cell lysate but none was detected in the growth media. By contrast, a large amount of the antibody that had a secretory signal was present in the growth media. The induction of cells was observed for antibodies expressed from both formats. These results indicate that secretion is not obligatory for receptor activation by antibodies expressed intracellularly, likely because the receptor has the same overall topology irrespective of whether it is retained in the E.R lumen or anchored in the plasma membrane. In the secretory pathway the receptor active site is oriented to the E.R lumen whereas when anchored in the plasma membrane it faces the extracellular environment, but in both cases the signal-transduction domain faces the cytoplasm.

Figure 8:
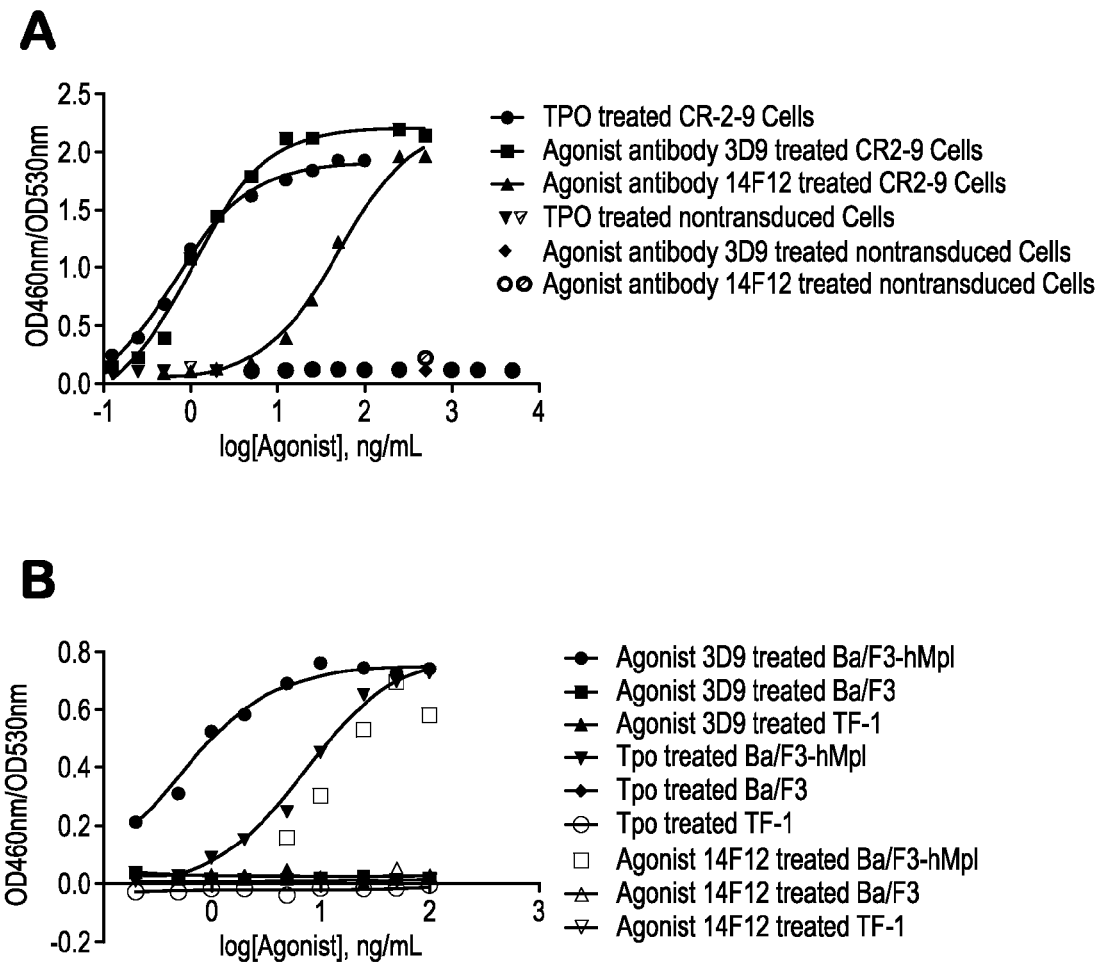
FIGS. 8A-8B show dose response of Tpo agonist antibodies in both fluorescence reporter and cell proliferation assays. (A) Reporter cells expressing the TpoR-IL6ST chimeric receptor were stimulated for 5 hours with agonist antibodies or Tpo over the indicated concentration range after which the cells were incubated for 2 hours with the LiveBLAzer-FRET B/G Substrate. Fluorescence emission ratios (460 nm-to-530 nm) were plotted against the indicated concentrations. HEK293T SIE-BLA cells were used as a negative control. (B) Tpo-dependent Ba/F3-hMPL cells were stimulated with agonist antibodies or Tpo for 72 hours over the indicated concentration range and cell proliferation was measured using a MTS assay. Ba/F3 cells or EPO-dependent TF-1 cells were used as negative controls. To calculate the EC50s, the data were fitted to 4-parameter logistic model with GraphPad Prism 6.

Thrombogenesis by Selected Antibodies:

Two of the most active antibodies (3D9 and 14F12) were expressed in HEK293F cells and were purified using protein-G affinity chromatography. The EC50 of the antibodies was determined using both the cell proliferation and fluorescent reporter assays (FIGS. 8A and 8B). Both antibodies are full agonists. In the short-term fluorescence assay, the EC50 of antibodies 3D9 and 14F12 are approximately 10 and 500 pM respectively, compared to the endogenous protein agonist Tpo that is about 20 pM. By contrast, in the long-term proliferation assay, the EC50 of antibodies 3D9 and 14F12 are 5 and 50 pM respectively compared to Tpo which, in this assay, has an Ec50 of 70 pM. The differences in these assays may reflect the superior stability of the antibody molecule which can have a half-life of weeks in serum as compared to about 20-40 hours for authentic Tpo. To determine if the antibodies and Tpo acted at the same site in the TpoR, we studied whether there was synergy between the different agonist antibodies and authentic Tpo. No synergy was observed and the activities of the endogenous agonist Tpo and the agonist antibodies were simply additive when both were employed at submaximal concentrations, indicating that the agonist antibodies and Tpo bind to different mutually exclusive binding sites, or to the same binding site in the TpoR.

To determine if the antibodies could induce megakaryocyte formation from human bone marrow stem cells, fresh CD34 positive cells were treated with the antibodies or Tpo and analyzed by flow cytometry using antibodies against the megakaryocytic marker CD41 as compared to the leukocyte marker CD45 RA. Both antibody 3D9 and Tpo markedly induced megakaryocyte formation from human stem cells. These studies were confirmed by confocal microscopic imaging using different channels and measurement of the characteristic multinuclear feature of mature megakaryocytes using nuclear staining and flow cytometry.

Figure 9:
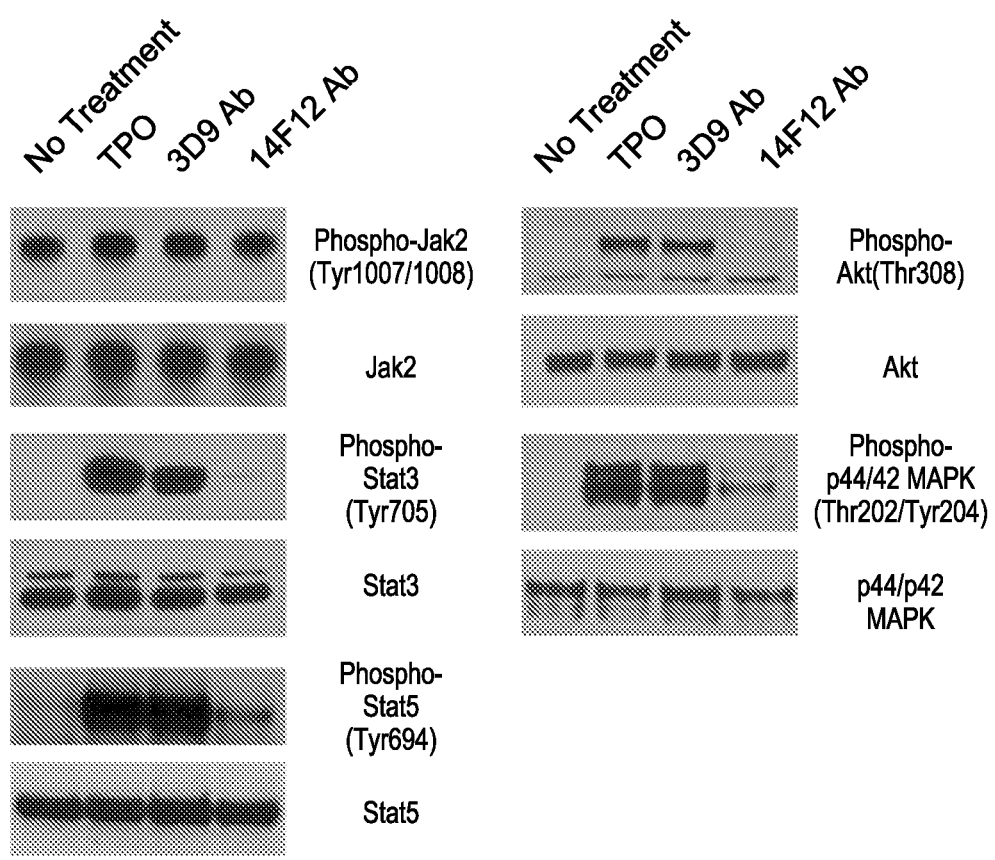
FIG. 9 shows signal transduction mediated by Tpo agonist antibodies. JAK2 was purified from cell lysates using affinity to anti-JAK2 agarose and its phosphorylation was detected by Western blotting using anti-phosphotyrosine antibodies. Phosphorylation of STAT3, STAT5, Akt and MAPK induced by agonist antibodies or rhTpo stimulation was detected by direct Western blotting of cell lysates.

The activation of cells by Tpo is accompanied by a characteristic pattern of protein phosphorylation in which the Jak2-Stat3/Stat5, PI3K-Akt, and MAPK pathways are engaged. We studied the ability of both Tpo and the agonist antibodies to activate these pathways using BAF-3 cells that expressed the wild type human TpoR which, unlike unmodified HEK293T (Sie-bla) cells, can respond to Tpo. Importantly, the agonist antibodies activated all three pathways, as did authentic Tpo, indicating that their mechanisms of action were similar (FIG. 9). As in other studies, antibody 3D9 was had a lower EC50 than antibody 14F12.

As an orthogonal measure of overall mechanistic similarity, highly specific kinase inhibitors were studied using the cell proliferation assay. If the agonist antibodies and authentic Tpo operate on the same pathway, the profile of inhibition should also be the same. We studied the kinase inhibitors LY294002, PD98059 and SD-1029 that are specific for the phosphatidylinositol 3(PI3), Jak2, and MEK-1 mediated pathways. The cell proliferation induced by both the agonist antibodies and authentic Tpo was inhibited in a dose dependent manner by the PI3K and JAK2 but not the MEK-1 inhibitors, again indicating that they activate similar pathways.

Figure 10:
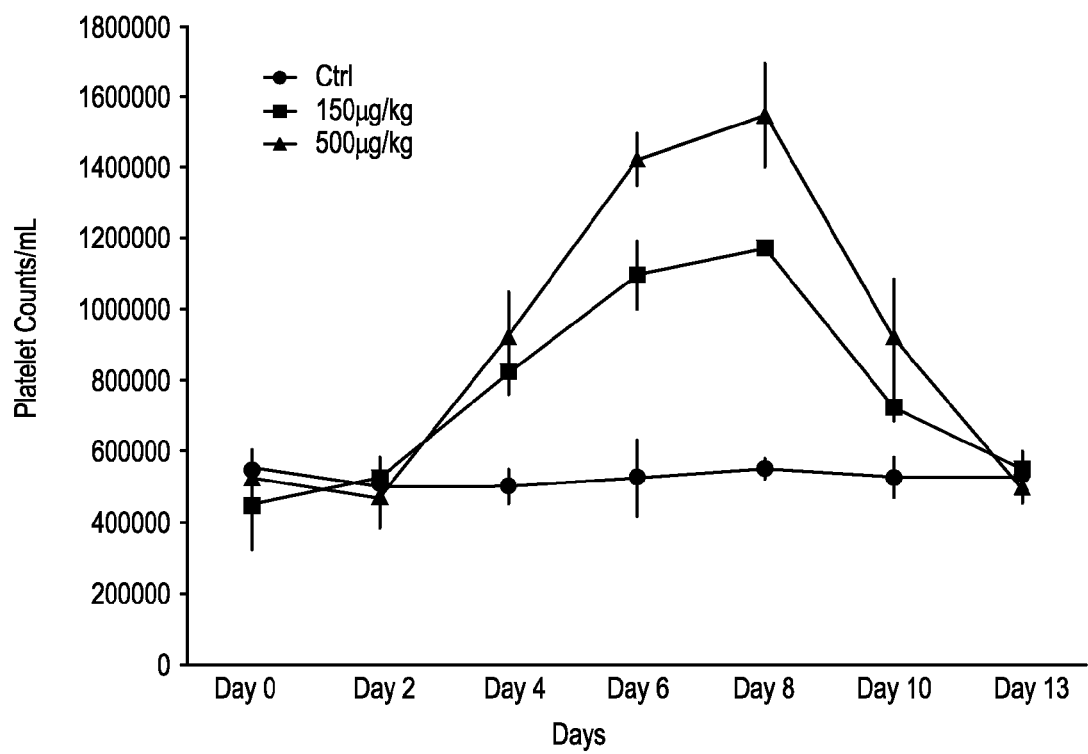
FIG. 10 shows in vivo activity of the Tpo agonist antibody 3D9 in the Balb/C mouse. Antibody at concentrations of 150 µg/kg, 500 µg/kg or the PBS vehicle were injected s.c. once at Day 0 and blood was collected every other day for 2 weeks using a Unopette. Platelets were counted with a Hemacytometer.

Activation of Platelet Formation In Vivo:

There is a high degree of sequence similarity between the murine and human TpoRs. This relatedness makes study of the activity of our agonist antibodies in the mouse feasible, thereby greatly simplifying assessment of their putative therapeutic utility. Immunochemical studies showed that antibody 3D9 reacts with both the human and mouse TpoRs. Also, both purified mouse and human TpoR ectodomains can inhibit the activation of the fluorescent reporter cells by the agonist antibody. We took advantage of this cross reactivity to study the ability of the agonist antibodies to induce platelet formation in vivo in the mouse. At a single dose of 540 micrograms per kilogram the agonist antibody 3D9 increased the platelet count three fold by eight days (FIG. 10). This degree of induction is better than the thrombogenesis seen with rhTpo in mice even though it was administered twice per day for five consecutive days.

More detailed description of materials and methods employed in this Example are provided below.

Cell Lines: The murine interleukin 3 dependent cell line Ba/F3 (Catalog No. ACC 300, DSMZ) was maintained in RPMI-1640 (Life Technologies) containing 10% (vol/vol) FCS (Life Technologies), penicillin, and streptomycin (Life Technologies) and 2 ng/mL rmIL3 (R&D Systems, Catalog No. 403-ML-010). The HEK293F cell line was maintained in Free Style F17 medium with 4 mM GlutaMAX (Life Technologies). The SIE-BLA HEK293T cell line (Life Technologies, Catalog No. K1649) was maintained in DMEM containing 10% (vol/vol) dialyzed fetal bovine serum (FBS), penicillin, and streptomycin, non-essential amino acids and HEPES (Life Technologies).

Selection of EPOR Binding Antibodies from Combinatorial Antibody Libraries in Phage: Recombinant purified human Thrombopoietin Receptor (TpoR) extracellular domain (Ser25-Trp491) (R&D systems, Catalog No. 4444-TR-050) was biotinylated with EZ-Link NHS-PEG4-Biotin and Biotinylation kits (Thermo Scientific, Catalog No.

21455) and the biotinylated protein was used for panning in solution. The combinatorial antibody scFv library in phage was incubated with the biotinylated TpoR extracellular domain after which Streptavidin coated Dynabeads M-280 (Life technologies, Catalog No. 11205) were added to pull down the TpoR-phage complex. Unbound phage were removed by washing. Bound phage were eluted with either Thrombopoietin (Tpo) (Sino Biological Inc., Catalog no. 10381-H08C) or glycine.HCl (pH 2.2). XL1-Blue cells were infected with the eluted phage and grown at 30° C. overnight. Bacteria were scraped from the plate and the helper phage VCSM13 was added to amplify phage for the next round of panning. Twenty-four clones from each protocol were harvested and their binding to the TpoR was analyzed by phage ELISA. The selected phagemids were sequenced by Sanger sequencing. Sequences were analyzed with Vbase2. The heavy chain CDR3s were aligned using Clustal W.

Establishment of Tpo responsive reporter cell lines and construction of a TpoR-IL6st chimeric receptor: Two Chimeric Receptors composed of the human TpoR and human IL6 signal transducer (IL6st, GP130) intracellular domain were constructed. In one case, the ectodomain of TpoR [from the N-terminus to the box I region (amino acids 1-527)] was linked to the IL6 signal transducer intracellular domain [from after the box I region to the C-terminus (amino acids 651-918)]. Alternatively, the TpoR ectodomain [from the N terminus to before the transmembrane helix (amino acids 1-491)] was linked to the IL6ST domain [from the transmembrane helix to the C-terminus (amino acids 605-918)]. The chimeric receptors were cloned into the lentiviral vector that used the Ubiquitin C promoter (UbC) to drive expression of the receptor.

The CellSensor SIE-bla HEK 293T cell line that contains a beta-lactamase reporter gene under control of the SIE response element was infected with Lentiviruses carrying the TpoR-IL6st chimeric receptor gene. The transduced cells were stimulated with recombinant Tpo and cells showing the greatest response to Tpo (having the highest OD460 nm-to-OD530 nm Ratio) were sorted into 96 well micro-titer plates using a MoFlo XDP Flow Cytometry Sorter. Single cell clones were allowed to reach confluence and the response of single clones to Tpo was measured in black-wall, clear-bottom assay plates using a fluorescence plate reader (Tecan, Infinite M200Pro) using an excitation filter of 409 nm and emission filters of 460 nm and 530 nm. The clone with the highest response to Tpo was designated CR2-9.

Establishment of BaF3/hMpl cell line: The wild-type human TpoR gene was cloned into the lentiviral vector and expressed under control of the UbC promoter. The murine interleukin 3 dependent cell Ba/F3 was transduced with lentiviruses carrying the TpoR gene and Tpo dependent cells were selected in RPMI 1640 medium containing 20 ng/mL rhTpo (R&D Systems, Catalog No. 288-TP-005).

Construction of the Lentiviral Combinatorial Antibody Library:scFv genes were cut from phagemid vector and sub-cloned into the lentiviral vector at the compatible asymmetric SfiI sites as described before.

Single Cell Selections Screening of TpoR Agonist Antibodies using FACS: Secreted antibody generated during lentivirus preparations was removed using protein G magnetic beads (New England Biolabs, Catalog No. S1430S). The completeness of the antibody depletion was confirmed by western blotting with HRP conjugated anti-human Fc antibody. The Tpo responsive HEK293T cell CR2-9 was plated at low density one day before transduction. After the cells were transduced with lentiviruses, methylcellulose based media was placed on top of cell layer prior to overnight culture to confine the secreted antibodies to the cells that produced them. Prior to harvesting the cells, the methylcellulose-based medium was dissolved using excess medium and discarded. Cells were detached and Live-BLAzer FRET BSG Loading substrate was added (Life Technologies, Catalog No. K1095). Cells with highest OD460 nm-to-OD530 nm ratio were sorted into 96 well micro-titer plates using a MoFlo XDP Flow Cytometry Sorter. Single cell clones were allowed to reach confluence and the conditioned medium harvested from them was added to 384 well black-wall, clear-bottom micro-titer assay plates containing CR2-9 cells for secondary screening. The conditioned media was also tested in 384 well micro-titer plates containing Ba/F3-hMpl cells. The effect on cell proliferation was determined using the CellTiter 96 Aqueous non-radioactive cell proliferation assay (Promega Corporation, Catalog No. G3580). Antibody genes from the clones giving highest signal were recovered by PCR and cloned into the pFUSE mammalian expression vector for sequencing and the unique antibody sequences were transfected into HEK293F cells to produce antibodies. Antibodies were purified using HiTrap Protein G HP columns (GE Healthcare Biosciences, Catalog No. 17-0405-01,) with ÄKTAxpress purifier.

Differentiation of Human CD34+ Hematopoietic Stem Cells (HSC):

The assays were done in duplicate with HSC cells from 2 different donors. CD34+ stem cells were isolated from human bone marrow using a direct immunomagnetic CD34 MicroBead labeling system (All Cells, catalog no. ABM010). About 50,000 CD34+ HSC cells were cultured in StemSpan serum-free media (SFEM) (Stemcell technologies, Catalog No. 09600) supplemented with 50 ng/mL human stem cell factor (SCF) only or SCF plus different concentrations of human Tpo agonist antibodies 3D9 or 14F12 for 14 days. For immunofluorescence assays, cells were fixed with 3% paraformaldehyde in PBS and blocked for 30 minutes in 2% BSA in PBS. The Fc Receptor on the cells was blocked for 10 minutes with purified IgG from human serum using a concentration of 100 ug/mL. (Sigma Life science, Catalog No. 14506,). Cells were stained with PE conjugated anti-human CD41 (Biolegend, Catalog No. 303705) and APC conjugated anti-human CD45RA (eBioscience, Catalog No. 17-0458-41).

Cell nuclei were stained with Hoechst Dye, washed with PBS, and analyzed with a LSRII Flow Cytometer (Becton Dickinson). For imaging by confocal microscopy, in addition to nuclear staining, the cell surface was stained with WGA Lectin FITC (Genetex, Catalog No. GTX 01502). Confocal microscopic imaging was carried out on cells deposited on slides using a cytospin centrifuge.

Phosphorylation Assays:

Ba/F3-hMpl cells were starved in RPMI-1640 medium containing 5% FBS without Tpo for 18 h. A total of $8 \times 10^6$ cells was used for each assay. Cells were treated at 37° C. for 20 min with RPMI serum-free medium containing 50 ng/mL Tpo, 100 ng/mL agonist antibody 3D9, or 200 ng/mL agonist antibody 14F12. The cells were washed once with ice-cold PBS containing 1× Halt protease and a phosphatase inhibitor mixture (Pierce Chemical, Catalog No. 78428) and lysed on ice for 30 min with occasional vortexing in 500 μL immunoprecipitation lysis buffer containing 2× Halt Protease and the phosphatase inhibitor mixture. Cell debris were removed by centrifugation at 13,000×g for 10 min. The phosphorylation status of Stat3, Stat5, Akt and p44/42 MAPK was determined by Western blot analysis of the cell lysates using anti-phospho-Stat3 (Tyr705) (D3A7) XP antibody (Cell Signaling Technology, Catalog No. 9145P), anti-Phospho-Stat5 (Tyr694) (D47E7) XP antibody (Cell Signaling Technology, Catalog No. 4322P,), anti-phospho-p44/42 MAPK (Erk1/2) (Thr202/Tyr 204) (197G2) antibody (Cell Signaling Technology, Catalog No. 4377S) and anti-phopho-Akt(Thr 308) (244F9) antibody (Cell Signaling Technology, Catalog No. 4056S). The amount of protein in the gel bands were quantitated using anti-total Stat3 (C-20)(Santa Cruz Biotechnology, Cat No.sc-482), anti-total Stat5 (C-17)(Santa Cruz Biotechnology, Catalog No. sc-835), anti-Akt (Cell Signaling Technology, Catalog No. 9272S) and anti-p44/42 MAPK antibody (Cell Signaling Technology, Catalog No. 9102S).

JAK2 was purified from cell lysates by immunoprecipitation for 3 hours at 4° C. with anti-JAK2 Agarose (EMD Millipore, Catalog No. 16-121). JAK2 was eluted with Low-pH Elution Buffer (Pierce, Catalog No. 88804) and neutralized with 2M Tries buffer. The immunoprecipitates were analyzed by Western blots using anti-phospho-JAK2 (Tyr1007/1008)(C80C3) antibody (Cell signaling Technology, Catalog No. 3776) and anti-total JAK2 antibody (C-14) (Santa Cruz Biotechnology, Catalog No. sc-34479).

Thrombogenesis in Mice:

Normal Balb/C mice, 9 weeks of age were divided into 3 groups of 6 mice each. The groups of mice were treated s.c. with 150 µg/kg or 500 µg/kg of 3D9 agonist antibody or PBS as control at Day 0. The antibody preparations contained Less than 0.0025 EU of endotoxin per µg of protein as determined by the Chromogenic LAL Endotoxin Assay (Genscript Corporation, Catalog No. L00350). Each mouse was anesthetized and 10 uL of blood was collected from the retro-orbital sinus using a capillary provided with Unopette Replacement (Medix, Catalog No. BTP-4015) every other day for 14 days (Day 0 before injection, days 2, 4, 6, 8, 10, 13 post treatment). The blood was transferred into an eppendorf tube prefilled with 1 mL Lysis buffer. The platelets were counted using a C-Chip INCYTO Disposable hemacytometer (Skc Inc. America, Catalog No. DHC-N01) using 40× objective and 10× ocular Zeiss lenses.

The studies described in this Example demonstrated that the cytokine pathways activated via JAK/STAT signaling can be selected by FACS and the antibody gene(s) recovered. The system is also applicable to selection of other important antibodies such as those that modulate GPCR pathways where one can study, for example, β-arrestin based systems by employing the same FRET substrate used here.

While discovery systems based on pathway activation are in use for small molecules, the system reported here differs in that it can simultaneously interrogate many more potential agonists among the antibodies in the infecting lentiviruses because the library size is very large, and can be interrogated using single cell formats. Another important difference is that candidate agonists replicate thereby allowing the selected molecules to be identified and produced in quantity without any need for initial addressability.

Because we employed a genetics based method, large numbers of potential agonists are produced in the very small volume element of a single cell or its compartments such that their molar concentrations at the receptor expressed by the same cell are very high. Indeed, as described herein, we have used this method to generate rapidly agonist antibodies to other cytokine receptors, integrins, and ion channels, as well as those that regulate morphogenesis and inhibit viral replication. In some of these cases pre-selection against known targets was used, whereas in others the selection was blind. These studies also showed that the method is not confined to secreted antibodies that only act at the external face of the plasma membrane, thereby generalizing it to any molecule that coexists with an antibody in a variety of sub-cellular compartments.

Example 9 Selection of Antibody Agonists that Trans-Differentiate Human Stem Cells This Example describes generation and selection of antibody agonists from intracellular combinatorial libraries that trans-differentiate human stem cells. We used combinatorial antibody libraries in their "near neighbor" format to co-express antibodies and the granulocyte colony stimulating factor receptor (G-CSFR). Remarkably, using this method, we isolated an agonist antibody to the G-CSFR that can induce human CD34+ stem cells to form neural progenitor cells. Because CD34+ stem cells are of the myeloid lineage, this antibody appears to induce a trans-differentiation process.

Construction of "Near Neighbor" Antibody Libraries:

Many different antibody formats that address diverse cellular compartments can be used for intracellular combinatorial libraries. In our previous studies using intracellular libraries coupled to single cell selection systems, we generated many antibodies that were phenocopies of the natural agonists. Since antibody agonists have the potential to bind to receptors in a way that is different from the natural agonists, they are potentially capable of pleiotropic effects. To favor the selection of antibodies that bind to receptors in unusual ways, we generated a new format in which members of the combinatorial antibody libraries are integrated into the plasma membranes of target cells. Selections using anchored antibodies are based on an autocrine mechanism in which one ensures that the antibody acts on the cell that produced it.

A single chain ScFv that is dimerized by the appended Fc domains is linked via a flexible linker to a platelet derived growth factor receptor (PDGFR) membrane-spanning domain such that the antibody molecules are integrated as dimers into the plasma membrane with their binding sites facing the solvent. We termed these libraries "near neighbor" libraries because the reactivity of the antibody is likely constrained to available regions of neighboring molecules. The central concept was that by using "near neighbor" libraries, unusual antibodies that are not seen frequently when selections are carried out in solution might be favored because of the coupling of constrained reaction geometries to a very high effective molarity for the interacting pairs. The method also has the important advantage that the target receptor is present in its natural milieu, thus, ensuring the presence of physiologically relevant conformations.

We then tested the potential for an antibody that is a known thrombopoietin (Tpo) phenocopy in its soluble form to function when it is co-expressed and anchored in the plasma membrane along with its thrombopoietin receptor (TpoR) target. The antibody still functioned as an agonist when it was integrated into the plasma membrane suggesting that it could activate a neighboring TpoR. Two separate assays were used. In one, a FRET fluorescence reporter assay that measured activation of the signal transduction pathway was studied. The second assay measured stimulation of cell growth. To confirm that the antibody activated the same cell that expressed it, and not an adjacent one by cell-cell interaction, cells were plated at a low density so they could be studied individually. When the culture was exposed to the FRET substrate, cells in isolation were found to be activated, strongly suggesting that the membrane bound antibody activated the cell expressing it by binding to a neighboring receptor. No activation was observed in cells infected with a virus expressing red fluorescent protein alone.

Isolation of G-CSF Antibody Phenocopies:

To increase the potential for isolation of unusual antibodies, a dual selection strategy was used. In the first step, antibodies that bound to the G-CSFR ectodomain in solution were selected from a combinatorial library expressed in phage that contained about $1.0 \times 10^9$ members. The purpose of this step was to select binding antibodies from a large diversity system in order to enter the highest number of candidates into the more stringent secondary screen. We expect this enriched library to have large numbers of antibodies to easily available epitopes and fewer to other regions. The secondary "near neighbor" screen that is based on function rather than simple binding, was designed to both isolate directly those members of the pre-selected library that are agonists and, uncover those, perhaps rare, antibodies with unusual functions. Thus, the antibodies that were pre-selected in phage after two rounds of panning were converted into a plasma membrane binding format and transferred to lentivirus for infection of reporter cells. The entire pool of these selected antibodies that had about $5.0 \times 10^5$ members was used to infect reporter cell lines where an anchored G-CSFR was co-localized in the plasma membrane. In these reporter cell lines either the growth of BaF3 cells or induction of a FRET signal in SIE/BLA/SIG cells was strictly dependent on the presence of a G-CSFR agonist. Both infection with the antibody library or exposure to authentic G-CSF activated the G-CSFR in these cells. Again, infection with a virus encoding the red fluorescent protein alone did not activate the cells.

Figure 11:
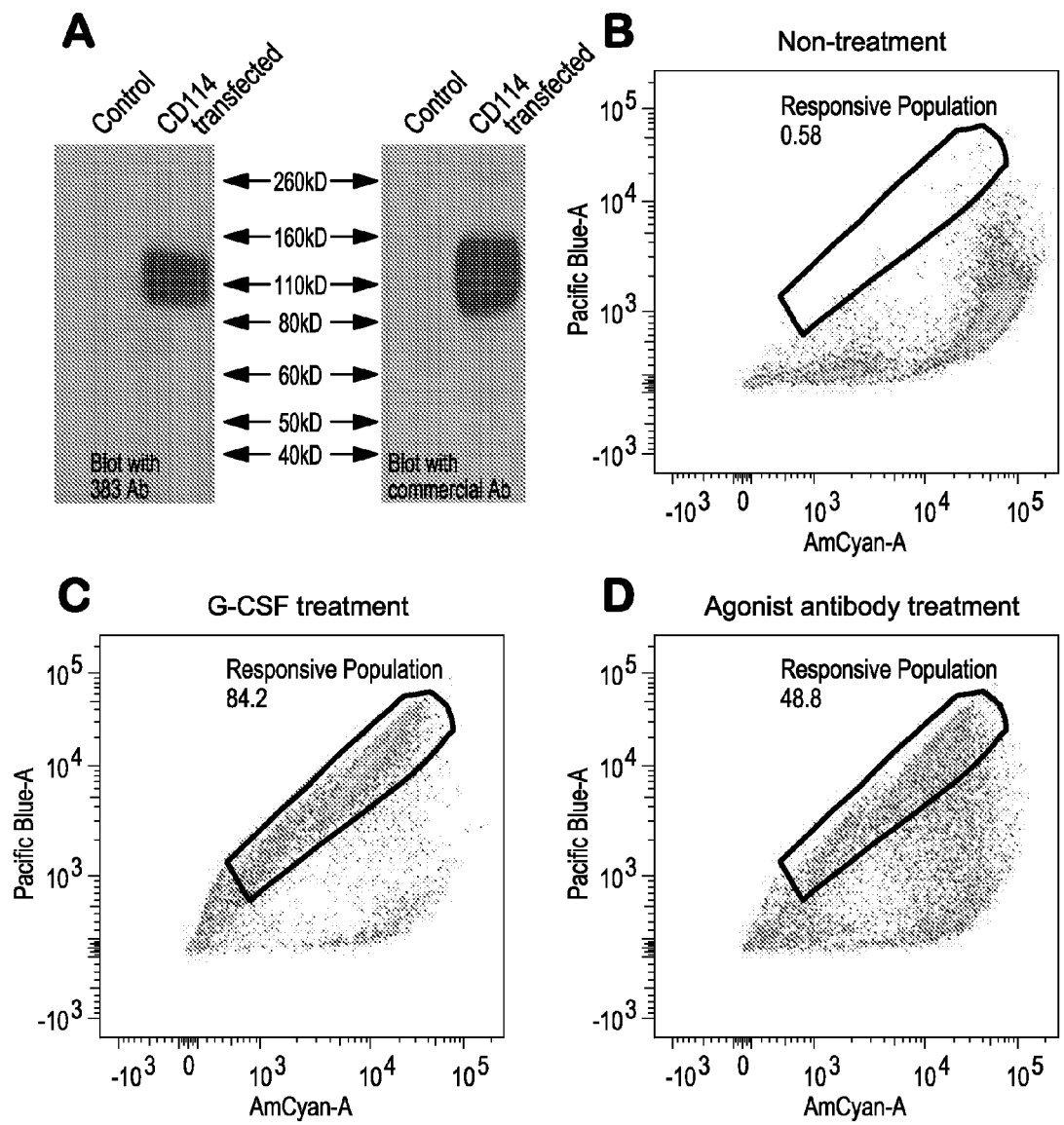
FIGS. 11A-11D show that the G-CSF receptor is recognized and activated by the selected antibody 3B3.

Although the selected antibodies were agonists when integrated into the plasma membrane, it was important to demonstrate that they were also functional as soluble proteins in a fashion that is similar to the endogenous GCSF agonist that is a secreted growth factor. To study this, the selected antibody genes were converted to a secretory format in an expression vector that was used to transfect HEK-293 cells in 96 well plates. The secreted antibodies were harvested and tested for their ability to bind to the G-CSFR and activate reporter cells. Sequencing of the antibody genes from the positive clones revealed that they all derived from a single clone, which indicates strongly that a selectable event occurred. This clone was present in the original pool at a frequency of less than 10% as determined by sequence of the antibody genes from 50 randomly picked bacterial colonies, and could easily have been lost if the selection was confined to more rounds of panning in phage. An analysis of the affinity purified antibody by western blotting and FACS showed that it bound strongly to the G-CSFR (FIG. 11A) and was an agonist (FIGS. 11B-11D). Additional studies showed that the purified antibody induced both G-CSFR downstream signaling and growth in the reporter cell lines. To complete the cycle, the antibody was re-converted to its membrane tethered format (MTA) in lentivirus and after infection was again capable of activating selectively the reporter cells.

To determine if antibody and its receptor target actually co-localize in the plasma membrane, fluorescence microscopy study of cells expressing both the G-CSFR and the selected antibody clone 3B3 were carried out. These studies showed that both the antibody molecules and the G-CSFR are simultaneously expressed strongly on the plasma membrane and co-localize in the classical patches induced by cross linking. Receptor activation by either G-CSF or the agonist antibody was again strictly dependent on the presence of the G-CSFR. There was no activation of mock-transfected cells by either G-CSF or the agonist antibodies.

Trans-Differentiation of Human Stem Cells:

Since the main purpose of developing "near neighbor" combinatorial antibody libraries, was to select agonists that might act in unusual ways, we tested the ability of these G-CSFR binding antibodies in their soluble format to activate human CD-34+ stem cells. We thought that they could possibly be more potent and/or drive differentiation further along pathways of the myeloid lineage. However, what actually happened was that, unlike the natural ligand, the antibodies initiated neurogenesis in these stem cells.

Figure 12:
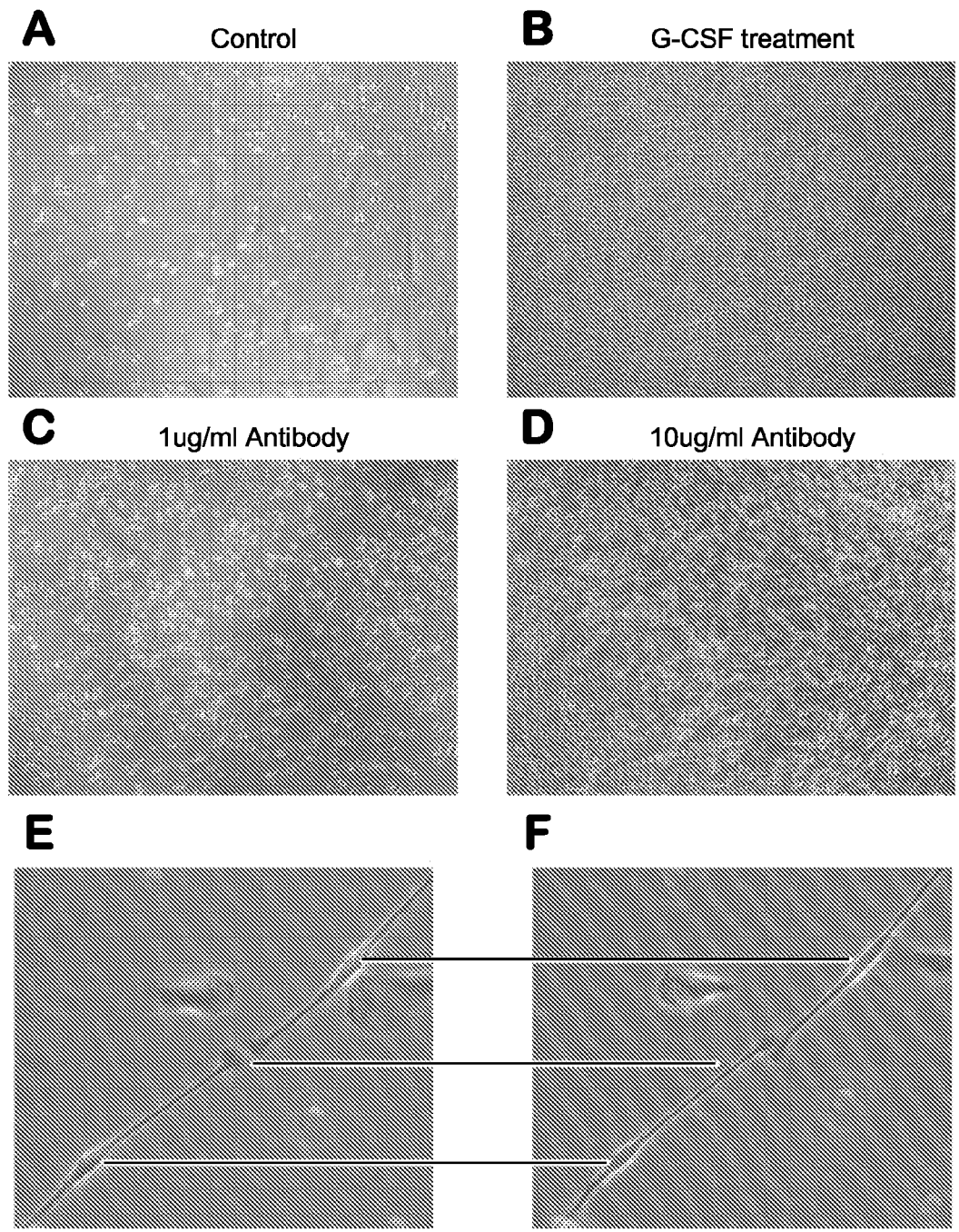
FIGS. 12A-12F show views of the CD34+ cells that attached to uncoated glass cover slips after two weeks of treatment with the selected G-CSFR agonist antibodies, which are indicative of neural development.

CD-34+ stem cells were isolated on separate occasions by cell sorting from five individuals. The sorted cells had a purity of 96-99%. In the first experiment, one half of the cells were treated with G-CSF and the other half was treated with the selected soluble antibody 3B3. As expected, G-CSF caused proliferation of cells that did not attach to the dish and had morphologies characteristic of the myeloid lineage. By contrast, the antibodies caused widespread formation of cells that attached to the dish. Attachment started at eight days, and by 14 days, about 40% of the cells attached and appeared to have characteristics most consistent with those of cells undergoing neural development (FIG. 12A-12F). These cells were mobile, had long neuritis, and exhibited multiple morphologies including bipolar configurations and extensive development of pyramidal shaped growth cones (FIG. 12E-12F). Scanning electron microscopy was carried out on these cells to obtain further morphological details. These studies showed that the growth cones on the neurite tips had a classical morphology with extensive formation of filopodia and lamellipodia.

Induction of neural cells was observed in repeated experiments from different donors of CD34+ cells. Similar morphological features were not observed when the same cell populations were treated with G-CSF, irrelevant antibodies, or with agonist antibodies to other receptors on CD-34+ cells such as integrins. To confirm that these cells were of neural lineage, they were studied by fluorescent microscopy for the presence of neuronal tubulin (Tuj1) as a highly specific neuronal marker, nestin as a transient marker of neural progenitor cells, F-actin as a component of growth cones, and CD-29 as a marker of cells of other lineages, including fibroblasts. Intense staining of the cells was observed with antibodies to F-actin, Tuj1 tubulin and nestin. By contrast, the cells did not express the fibroblast marker, CD-29. The F-actin, and the neurospecific Tuj1 protein were organized into the canonical patterns observed in the growth cones of neural progenitor cells. Tuj1 tubulin extended into the growth cone margins and terminated at the actin bundles. The actin filaments at the tips of the growth cones ranged in morphology from spike-like to a more blunted arrangement.

The intensity of the tubulin stain allowed one to observe clearly the remarkable length of the developing neurites which is a distinguishing feature of cells of the neuronal lineage. Another feature of neuroblasts in culture is their growth cone motility. To study this feature, cells were observed at one-hour intervals. Even in this short interval, extensive motility of the growth cones accompanied by neurite extension could be observed easily.

Differential Activation of Signal Transduction Pathways and Gene Expression:

Because the antibodies apparently trans-differentiated stem cells, one might expect that the activation of signal transduction pathways would be different than those used generally by cytokines such as G-CSF. To test this, freshly isolated human CD34+ bone marrow stem cells were treated with either G-CSF or the agonist antibody and the activation of the major G-CSF receptor signaling pathways such as STAT5, AKT, and ERK were analyzed using selective anti-phospho-antibodies. G-CSF induced phosphorylation of STAT5, AKT, and ERK, whereas the antibody induced stronger phosphorylation of AKT but did not affect STAT5 or ERK. Thus, the cellular fate we observe may be the result of a concerted enhancement of one signal transduction pathway coupled with the loss others. Interestingly, the PI3 kinase/AKT pathway is known to be important in neurogenesis.

A more comprehensive analysis of the induction of gene expression was carried out using a RT-PCR array based analysis of neurogenesis in which the expression of 84 genes known to be important for neurogenesis were studied. The results are expressed as the ratio of induction by the antibody or G-CSF to that of untreated cells. The expressions of many genes important to neurogenesis were up-regulated by the antibody relative to those of un-induced cells or cells induced by G-CSF. This up-regulated expression includes genes encoding proteins that promote neurite outgrowth and adhesion (NRP1, NRP2, and NRCAM) and notch signaling (NRP2, HEY1, DLL1, and ADORA1), amongst others. While some induction of gene expression is common to G-CSF and the antibody, many are unique and highly activated by the antibody alone. An interesting gene whose expression is up-regulated far more than any of the others except ADORA1 (229 fold) is the gene involved in Norrie disease (NDP). This gene encodes a secreted protein that is a ligand in the Wnt/beta-catenin pathway and may play a role in the early development of the neuroectoderm.

This Example describes generation of antibody agonists from intracellular combinatorial libraries that trans-differentiate human stem cells. As detailed below, antibodies that are agonists for the granulocyte colony stimulating factor receptor were selected from intracellular libraries on the basis of their ability to activate signaling pathways in reporter cells. We used a specialized "near neighbor" approach in which the entire antibody library and its target receptor are co-integrated into the plasma membranes of a population of reporter cells. This format favors unusual interactions between receptors and their protein ligands and ensures that the antibody acts in an autocrine manner on the cells that produce it. Unlike the natural granulocyte-colony stimulating factor that activates cells to differentiate along a predetermined pathway, the isolated agonist antibodies trans-differentiated human myeloid lineage CD-34+ bone marrow cells into neural progenitors. This trans-differentiation by agonist antibodies is different from more commonly used methods because initiation is agenetic. Antibodies that act at the plasma membrane may have therapeutic potential as agents that trans-differentiate autologous cells.

The results from these studies demonstrated that antibody agonists and the natural ligand that bind to the same receptor can induce different cell fates from an identical starting cell population.

Example 10 Selection of Antibody Agents Based on Modulation of Morphology

The phenotypic screening described in the invention is a general method and could be used to select agonists for known or unknown proteins that are present in any cellular pathway for which a selection system is available. This Example describes selection of antibody agonists based on the ability of intracellular antibodies to alter the morphology of stem cell colonies growing in soft agar. The antigenic targets and agonist properties of such antibodies allow identification of proteins involved in stem cell fates. Essentially, this is a forward genetics approach that operates at the protein level, with the important difference that the antibody probe, itself, may become the therapeutic agent.

One of the general observations in biology is that cells change morphology during development and differentiation. If a selection format that harnesses this general feature of cell development could be devised, it could be a novel-screening format for selection of antibodies that induce differentiation. This is similar in concept to our previous selections of antibody agonists that are cytokine phenocopies, but it has another degree of difficulty because the target space is likely to be large and mostly unknown. Also, in a search for unknown targets, unbiased libraries must be used where the frequency of recovered agonists will necessary be lower than that seen with libraries preselected for binding to known proteins. On the other hand, because the targets are unknown, the potential for new discoveries is high.

The growth and morphology of colonies of cells growing in soft agar has been used widely as a measure of the malignant state of cancer cells that have lost anchorage dependence or to assay for the effects of growth factors on cellular proliferation. We reasoned that this approach could be extended to the study of stem cells where the morphology of their colonies would vary as a function their differentiated state. Thus, agonist antibodies that induce morphological changes in cell colonies could be selected from stem cells infected with antibody libraries. This approach could inform as to whether the scope of a method that has already been employed successfully for selection of cytokine phenocopies can be extended to the more general biological problem of correlating protein components of pathways with cellular phenotypes.

Here we show that infection of stem cells with unbiased combinatorial antibody libraries caused growth of colonies in soft agar that exhibit a variety of morphologies. When fresh stem cells were treated with the antibodies recovered from these colonies their growth and morphological characteristics in soft agar were reproduced. Using mass spectroscopy, the targets for the recovered antibodies were shown to be channels or integrins. In each case the antibodies function as agonists as revealed by their activation of downstream pathways. The antibody that is an integrin agonist causes the cells to differentiate into cells of the macrophage lineage including those with dendritic and foam cell phenotypes. The power of the overall selection process was shown by the fact that it was accompanied by convergent evolution in which selected antibodies had the integrin binding sequence, RGD, in their CDR-H3. When the RGD sequence was mutated to RGE all agonist activity was lost.

Strategy of Antibody Selection with Unbiased Combinatorial Antibody Libraries:

To select the active antibody against unknown target that influence phenotypes of cells, we devised a method based on infectious combinatorial antibody libraries, colony forming assay and mass spectrometry (MS) analysis without conventional antibody panning. First, to construct the lentiviral antibody libraries, we harvested phagemids pool from naïve human combinatorial antibody phage libraries. Then, we constructed scFv-Fc antibody genes in lentiviral vector. The library size was $10^8$. Then, to produce the lentivirus, we transiently transfected lentiviral antibody library and plasmids of virus packaging to HEK293T cells. After virus titration, we infected lentiviral library to TF-1 erythroblast cells and loaded to methylcellulose agar for morphogenic screening. Compared to control, there were several types of colonies such as amorphous, scattered, linear or round shapes.

Selection of Antibodies Based on Morphogenic Phenotypes:

Based on morphology criteria, we picked thirty colonies which showed specific morphologies after two weeks. Then each antibody gene was amplified by PCR and twenty antibody genes were recovered. The genes encoding the antibody heavy chain CDR3 (CDR-H3) regions were analyzed to measure the number of different sequences of each clone. Each colony showed between one and four different antibodies. The antibodies encoded by the lentiviruses were generated by transient transfection of HEK 293T cells with single or combination of two genes and fifty-one combined supernatants were tested for their ability to influence the proliferation of TF-1 cells. Eight antibodies had ~50% of the activity of GM-CSF. Interestingly, three active antibodies were bispecific. For the next process, we selected arbitrarily three antibodies (9-3, 11-3 and 12-1/12-2) which represent unique morphologies.

Identification of Target Proteins:

We transfected antibody genes encoding 3 active antibodies such as 9-3, 11-3 and 12-1/12-2 to 293F cells for antibody production and purified them. These antibodies were tested if they activate cellular functions. They increased the proliferation of TF-1 cells and phosphorylations of key signaling molecules such as AKT and ERK. Especially the 9-3 activated the phosphorylation of STAT5 in addition. Then we immunoprecipitated the TF-1 cell lysates by each antibody. The immunoprecipitated protein samples were immunoblotted by these antibodies or silver stained. The silver stained gel bands, which are matched with immunoblot, were sliced and trypsinized for nano-LC MS/MS analysis. We identified the antibody as a major protein (data not shown) and also obtained various non-antibody proteins in the analysis of the bands. Among the protein list, we chose candidate target proteins by several criteria such as expected sizes, cellular localizations. Integrin alpha3, HVCN1 and TRPM7 were fitted for these criteria as candidate target proteins of each antibody. Because integrins are well known for their importance in pathophysiology, we selected this target for further characterization of active antibody to prove our method. Using human integrin alpha3 overexpressed lysate, we confirmed that the 12-1/12-2 interacts with human integrin alpha3 by immunoblot. Next, we tested if 12-1/12-2 binds to other major types of integrin alpha such as integrin alphaV or alpha5. 12-1/12-2 interacted with integrin alphaV as well. This observation implies that 12-1/12-2 is not specific binder of integrin alpha3, it may associate with other integrin alpha.

Antibody Increased Migration of Human Bone Marrow CD34$^+$ Cells:

The TF-1 cells are widely used for the studies related with the functions of various cytokines. However, TF-1 cells are erythroblast which major cell populations are fated to differentiation into erythrocytes, therefore, it's not suitable for investigating the potential of agonists in broad ranges of cell types and phenotyping. We loaded human bone marrow CD34$^+$ cells to methylcellulose agar containing 12-1/12-2. After one week, 12-1/12-2 enhanced scattering of cells and podia formation compared to controls. To characterize the cells in detail, we analyzed each single cell by scanning electron microscopy (SEM). Under the SEM, 12-1/12-2-treated cells showed increased formation of podia. Next, we tested if these effects affect cellular movement which was known as one of key cellular function of integrin signal. When the 12-1/12-2 was treated to human bone marrow CD34$^+$ cells, migration of bone marrow CD34$^+$ cells from upper chamber to lower chamber was increased and the phosphorylations of AKT and ERK known as key downstream molecules of integrin signaling were potently increased. These observations imply that 12-1/12-2 may influence the motility of human bone marrow CD34$^+$ cells by enhancing the podia formation which was known as major regulation by integrin signaling.

Antibody Induced the Differentiation of Human Bone Marrow CD34$^+$ Cells into Dendritic Cells:

Because bone marrow CD34$^+$ cells contain pluripotent stem cells that give rise to all cell types in blood, it may differentiate various lineages by extracellular stimuli such as immune cytokines. So we checked whether 12-1/12-2 has a capability to induce specific lineage of stem cells. The results indicate that 12-1/12-2 increased the population of cells which showed unique morphology such as dendritic cells. We observed that the cells expressed CD11c, the specific marker of dendritic cell by Immunocytochemical studies. These observations indicate that 12-1/12-2 may specifically induce the dendritic cells from bone marrow CD34$^+$ cells.

Convergent Evolution:

Interestingly, 12-2 of 12-1/12-2 contains the Arg-Gly-Asp (RGD) integrin recognition motif of the natural ligand within the CDR-H3. To examine the contribution of the RGD motif of CDR-H3 in the cellular function of 12-1/12-2, this sequence was mutated to RGE by site-directed mutagenesis. The D (Asp) to E (Glu) exchange within the RGD motif is known to reduce or abolish ligand recognition by integrin alpha subunits. The phosphorylations of major integrin signaling molecules such as AKT and ERK by 12-1/12-2 were significantly inhibited by RGE mutation. In addition, the RGE mutant antibody showed decrease of dendritic cell differentiation by flow cytometric analysis. This finding implies that RGD of 12-2 is critical for antibody-integrin binding.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

Sequences of some exemplified agonist antibodies

```
EpoR antibody E-1 amino acid sequence
heavy chain
                                      (SEQ ID NO: 7)
MAQVQLVESGAEVKKPGASVKVSCKASGYTFTGYYMHWVRQAPGQ

GLEWMGWINPNSGGTNYAQKFQGRVTMTRDTSISTAYMELSRLRS

DDTAVYYCARLSSGWTFDYWGQGTLVTVSS light chain
                                      (SEQ ID NO: 8)
EIVLTQSPDSLAVSLGERATINCKSSQSVLYSPNNKNYLAWYQQK

PGQPPKLLIYWASTRESGVPERFSGSGSGTDFTLTISSLHAEDVA

LYYCQQSYSLPFTFGPGTKVEIKR
```

EpoR antibody V-1 amino acid sequence
heavy chain (SEQ ID NO: 21)
MAQVQLVQSGAEVKKPGSSVKVSCKASGGTFSSYAISWVRQAPGQ

GLEWMGGIIPIFGTANYAQKFQGRVTITADESTSTAYMELSSLRS

EDTAVYYCARDQGYYYGSGGLDYWGQGTLVTVSS light chain (SEQ ID NO: 22)
DIQMTQSPSSLSASVGDRVTITCRASQSISSYLNWYQQKPGKAPK

LLIYAASSLQSGVPSRFSGSGSGTDFTLTISSLQPEDFATYYCLQ

DYNYPLTFGGGTKVEIK

EpoR antibody V-3 amino acid sequence
heavy chain (SEQ ID NO: 23)
MAQVQLVQSGAEVKKPGASVKVSCKASGYTFTSYGISWVRQAPGQ

GLEWMGWISAYNGNTNYAQKLQGRVTMTTDTSTSTAYMELRSLRS

DDTAVYYCARGVAAALSYWGQGTLVTVSS light chain (SEQ ID NO: 24)
QSALTQPASVSGSPGQSITISCTGTSSDVGAYNYVSWYQQHPGKA

PKLMIYEVTKRPSGVPDRFSGSKSGNTASLTISGLQAEDEADYYC

ISFTASSTWAFGGGTKLTVLG(SEQ ID NO: 24)

EpoR antibody E-1 nucleotide sequence
heavy chain (SEQ ID NO: 25)
ATGGCACAGGTGCAGCTGGTGGAGTCTGGGGCTGAGGTGAAGAAG

CCTGGGGCCTCAGTGAAGGTCTCCTGCAAGGCTTCTGGATACACC

TTCACCGGCTACTATATGCACTGGGTGCGACAGGCCCCTGGACAA

GGGCTTGAGTGGATGGGATGGATCAACCCTAACAGTGGTGGCACA

AACTATGCACAGAAGTTTCAGGGCAGGGTCACCATGACCAGGGAC

ACGTCCATCAGCACAGCCTACATGGAGCTGAGCAGGCTGAGATCT

GACGACACGGCCGTGTATTACTGTGCGAGACTTAGCAGTGGCTGG

ACCTTTGACTACTGGGGCCAGGGAACCCTGGTCACCGTCTCCTCA light chain (SEQ ID NO: 26)
GAAATTGTGCTGACTCAGTCTCCAGACTCCCTGGCTGTGTCTCTG

GGCGAGAGGGCCACCATCAACTGCAAGTCCAGCCAGAGTGTTTTA

TACAGCCCCAACAATAAGAACTATTTAGCTTGGTATCAGCAGAAA

CCAGGACAGCCTCCTAAGCTACTCATTTACTGGGCGTCTACCCGG

GAGTCCGGGGTCCCCGAGCGATTCAGTGGCAGCGGGTCTGGGACA

GATTTCACTCTCACCATCAGCAGCCTGCACGCTGAAGATGTGGCA

CTTTATTACTGTCAGCAGTCTTATAGTCTTCCATTCACTTTCGGC

CCTGGGACCAAGGTGGAGATCAAACGT

EpoR antibody V-1 nucleotide sequence
heavy chain (SEQ ID NO: 27)
ATGGCACAGGTGCAGCTGGTGCAATCTGGGGCTGAGGTGAAGAAG

CCTGGGTCCTCGGTGAAGGTCTCCTGCAAGGCTTCTGGAGGCACC

TTCAGCAGCTATGCTATCAGCTGGGTGCGACAGGCCCCTGGACAA

GGGCTTGAGTGGATGGGAGGGATCATCCCTATCTTTGGTACAGCA

AACTACGCACAGAAGTTCCAGGGCAGAGTCACGATTACCGCGGAC

GAATCCACGAGCACAGCCTACATGGAGCTGAGCAGCCTGAGATCT

GAGGACACGGCCGTGTATTACTGTGCGAGAGATCAGGGGTATTAC

TATGGTTCGGGGGGCTTGACTACTGGGGCCAGGGAACCCTGGTC

ACCGTCTCCTCA light chain (SEQ ID NO: 28)
GACATCCAGATGACCCAGTCTCCATCCTCCCTGTCTGCATCTGTAG

GAGACAGAGTCACCATCACTTGCCGGGCAAGTCAGAGCATTAGCAG

CTATTTAAATTGGTATCAGCAGAAACCAGGGAAAGCCCCTAAGCTC

CTGATCTATGCTGCATCCAGTTTGCAAAGTGGGGTCCCATCAAGGT

TCAGCGGCAGTGGATCTGGCACAGATTTCACTCTCACCATCAGCAG

CCTGCAGCCTGAAGATTTTGCAACTTATTACTGTCTACAAGATTAC

AATTACCCGCTCACTTTCGGCGGAGGGACCAAGGTGGAGATCAAA

EpoR antibody V-3 nucleotide sequence
heavy chain (SEQ ID NO: 29)
ATGGCACAGGTGCAGCTGGTGCAATCTGGGGCTGAGGTGAAGAAGC

CTGGGGCCTCAGTGAAGGTCTCCTGCAAGGCTTCTGGTTACACCTT

TACCAGCTATGGTATCAGCTGGGTGCGACAGGCCCCTGGACAAGGG

CTTGAGTGGATGGGATGGATCAGCGCTTACAATGGTAACACAAACT

ATGCACAGAAGCTCCAGGGCAGAGTCACCATGACCACAGACACATC

CACGAGCACAGCCTACATGGAACTGAGGAGCCTGAGATCTGACGAC

ACGGCCGTGTATTACTGTGCGAGAGGAGTAGCAGCAGCTTTATCCT

ACTGGGGCCAGGGCACCCTGGTCACCGTCTCCTCA light chain (SEQ ID NO: 30)
CAGTCTGCCCTGACTCAGCCTGCCTCCGTGTCTGGGTCTCCTGGAC

AGTCGATCACCATCTCCTGCACTGGAACCAGCAGTGACGTTGGTGC

TTATAACTATGTCTCCTGGTACCAACAGCACCCAGGCAAAGCCCCC

AAACTCATGATTTATGAGGTCACTAAGCGGCCCTCAGGGGTCCCTG

ATCGCTTCTCTGGGTCCAAGTCTGGCAACACGGCCTCCCTGACCAT

CTCTGGGCTCCAGGCTGAGGACGAGGCTGATTATTACTGCATCTCT

TTTACAGCCTCCTCCACTTGGGCGTTCGGCGGAGGGACCAAGCTGA

CCGTCCTAGGT

3D9 TpoR agonist antibody amino acid sequence
scFv sequence (SEQ ID NO: 32)
MAQVQLVQSGAEVRKVGSSVKVSCKASRDTFNTYGISWVRQAPGQG

LEWMGGIIPIFGTADYAQKFRGRVTITADESTSTAYMELSSLRSED

TAVYYCARDRKLGGSDYWGQGTLVTVSSGGGGSGGGGSGGGGSDIV

MTQSPSSVSASVGDKVTITCRASQGLGRWLAWYQQEPGKAPKLLIY

AASTLQRGVPSRFSGSGSGTDFTLTISSLQPEDFATYYCQQSNSFP

WTFGQGTKLEIKR

Heavy chain variable region sequence
(SEQ ID NO: 33)
MAQVQLVQSGAEVRKVGSSVKVSCKASRDTFNTYGISWVRQAPGQG
LEWMGGIIPIFGTADYAQKFRGRVTITADESTSTAYMELSSLRSED
TAVYYCARDRKLGGSDYWGQGTLVTVSS Light chain variable region sequence
(SEQ ID NO: 34)
DIVMTQSPSSVSASVGDKVTITCRASQGLGRWLAWYQQEPGKAPKL
LIYAASTLQRGVPSRFSGSGSGTDFTLTISSLQPEDFATYYCQQSN
SFPWTFGQGTKLEIKR 3B3 anti-G-CSFR agonist antibody amino acid
sequence scFv sequence
(SEQ ID NO: 40)
MAQVQLLESGPGLVKPSQTLSLTCTVSGGSISSGGYYWSWIRQPPGK
GLEWIGYIYYSGSTNYNPSLKSRVTISVDTSKNQFSLKLSSVTAADT
AVYYCARWNGVNNAFDIWGQGTLVTVSSGGGGSGGGGSGGGGSDIQM
TQSPSSVSASVGDRVTITCRASQGISSWLAWYQQKPGKAPKLLIYAA
SSLQSGVPSRFSGSGWGTELTLTISSLQPEDFATYYCLQHNTYPFTF
GQGTKVTVLG Heavy chain variable region sequence
(SEQ ID NO: 41)
MAQVQLLESGPGLVKPSQTLSLTCTVSGGSISSGGYYWSWIRQPPGK
GLEWIGYIYYSGSTNYNPSLKSRVTISVDTSKNQFSLKLSSVTAADT
AVYYCARWNGVNNAFDIWGQGTLVTV Light chain variable region sequence
(SEQ ID NO: 42)
DIQMTQSPSSVSASVGDRVTITCRASQGISSWLAWYQQKPGKAPKL
LIYAASSLQSGVPSRFSGSGWGTELTLTISSLQPEDFATYYCLQHN
TYPFTFGQGTKVTVLG 9-3 agonist antibody amino acid sequences
scFv sequence
(SEQ ID NO: 48)
QVQLVESGGGLVQPGGSLRLSCAASGFSFTTYGMNWVRQAPGKGL
EWVSYISSSSSTIYYTDSVKGRFTISRDNAKNSLYLQMNSLSAGD
TAVYYCARGGDNSRGYYYIAGGDYWGQGTLVTVSSGGGGSGGGGS
GGGGSEIVLTQSPAIMSASPGERVTMTCSASSSIRYIYWYQQKPG
SSPRLLIYDTSNVAPGVPFRFSGSGSGTSYSLTINRMEAEDAATY
YCQEWSGYPYTFGGGTKVEIKR Heavy chain variable region sequence
(SEQ ID NO: 49)
QVQLVESGGGLVQPGGSLRLSCAASGESFTTYGMNWVRQAPGKGL
EWVSYISSSSSTIYYTDSVKGRFTISRDNAKNSLYLQMNSLSAGD
TAVYYCARGGDNSRGYYYIAGGDYWGQGTLVTVS Light chain variable region sequence
(SEQ ID NO: 50)
EIVLTQSPAIMSASPGERVTMTCSASSSIRYIYWYQQKPGSSPRL
LIYDTSNVAPGVPFRFSGSGSGTSYSLTINRMEAEDAATYYCQEW
SGYPYTFGGGTKVEIKR 11-3 agonist antibody amino acid sequences
scFv sequence
(SEQ ID NO: 57)
QVQLVETGAEVKKPGASVKVSCKASGYTFTGYYMHWVRQAPGQG
LEWMGWINPNSGGTNYAQKFQGRVTMTRVTSISTAYMELSRLRS
DDTAVYYCARGGPSYGDYFRWFDPWGQGTLVTVSSGGGGSEIV
LTQSPGTLSLSPGETATLSCRASHAVSSNSLAWYQQRPGQTPRL
LIYGASSRATGIPDRFSGSGSGTDFTLTISRLEPEDFAVYYCQQ
YGSSPPITFGQGPSWRSN Heavy chain variable region sequence
(SEQ ID NO: 58)
QVQLVETGAEVKKPGASVKVSCKASGYTFTGYYMHWVRQAPGQGL
EWMGWINPNSGGTNYAQKFQGRVTMTRVTSISTAYMELSRLRSDD
TAVYYCARGGPSYGDYFRWFDPWGQGTLVTVSS Light chain variable region sequence
(SEQ ID NO: 59)
EIVLTQSPGTLSLSPGETATLSCRASHAVSSNSLAWYQQRPGQTP
RLLIYGASSRATGIPDRFSGSGSGTDFTLTISRLEPEDFAVYYCQ
QYGSSPPITFGQGPSWRSN 12-1 agonist antibody amino acid sequences
scFv sequence
(SEQ ID NO: 66)
QVQLVQSGGGLVQPGGSLRLSCAASGFTFSSYEMNWVRQAPGKGL
EWVSYISSSGSTIYYADSVKGRFTISRDNAKNTLYLQMNSLRAED
TAVYYCAREVAAAGINDAFDIWGQGTMVTVSSGGGGSGGGGSGGG
GSETTLTQSPAIMSASPGERVTMTCSASSSIRYIYWYQQKPGSSP
RLLIYDTSNVAPGVPFRFSGSGSGTSYSLTINRMEAEDAATYYCQ
EWSGYPYTFGGGTKVDIKR Heavy chain variable region sequence
(SEQ ID NO: 67)
QVQLVQSGGGLVQPGGSLRLSCAASGFTFSSYEMNWVRQAPGKGL
EWVSYISSSGSTIYYADSVKGRFTISRDNAKNTLYLQMNSLRAED
TAVYYCAREVAAAGINDAFDIWGQGTMVTVSS Light chain variable region sequence
(SEQ ID NO: 68)
ETTLTQSPAIMSASPGERVTMTCSASSSIRYIYWYQQKPGSSPRL
LIYDTSNVAPGVPFRFSGSGSGTSYSLTINRMEAEDAATYYCQEW
SGYPYTFGGGTKVDIKR 12-2 agonist antibody amino acid sequences
scFv sequence
(SEQ ID NO: 75)
QVQLQQSGTEVVKPGASVKLSCKASGYIFTSYDINWVRQTPEQGL
EWIGWIFPGEGSTEYNEKFKGRATLSVDKSSTAYMELTRLTSED
SAVYFCARGDYYRRYFDLWGQGTLVTVSSRGGGGSETTLTQSPAF
KSATPGDKVTISCKASQDIDDDIVINWQHKPGAAAIFTTQEPTPL
VPGIPPRFSGSGSGTNFTLTIINIESEDAPYYFCLQHGDPLTWTF
GQGTKVDIK -continued Heavy chain variable region sequence
(SEQ ID NO: 76)
QVQLQQSGTEVVKPGASVKLSCKASGYIFTSYDINWVRQTPEQGLE
WIGWIFPGEGSTEYNEKFKGRATLSVDKSSSTAYMELTRLTSEDSA
VYFCARGDYYRRYFDLWGQGTLVTVSSR -continued Light chain variable region sequence
(SEQ ID NO: 77)
ETTLTQSPAFKSATPGDKVTISCKASQDIDDDMNWQHKPGAAAIFT
TQEPTPLVPGIPPRFSGSGSGTNFTLTIINIESEDAPYYFCLQHGD
FLTWTFGQGTKVDIK

---

We claim:

1. A method for identifying a modulator antibody of a phenotype of a eukaryotic cell type, comprising
   (a) expressing in a population of cells of the eukaryotic cell type by transducing a library of either
   secreted candidate antibodies or antigen-binding fragments thereof to produce a heterogeneous population of modified, antibody-expressing cells,
   wherein the transduced cells are plated in a diffusion restricting medium such that the secreted antibodies are trapped around the cells producing the secreted antibodies
   or
   membrane-integrated candidate antibodies or antigen-binding fragments thereof to produce a heterogeneous population of modified, antibody-expressing cells,
   wherein the entire membrane-integrated antibody library and its target receptor are co-integrated into the plasma membranes of said population of cells of the eukaryotic cell type,
   and
   (b) selecting, in an autocrine manner, a specific antibody-expressing cell with an altered phenotype relative to that of an unmodified control cell of said eukaryotic cell type;
   thereby identifying the candidate antibody expressed in the specific antibody-expressing cell as a modulator of the eukaryotic cell type.

2. The method of claim 1, wherein the library of candidate antibodies is expressed in the cells under conditions each cell expresses no more than 3 different antibody species.

3. The method of claim 1, wherein the library of candidate antibodies is a combinatorial library of secreted antibodies.

4. The method of claim 3, wherein the combinatorial antibody library is expressed in the cell via a lentiviral vector or a retroviral vector.

5. The method of claim 1, wherein the eukaryotic cell type is a mammalian cell type.

6. The method of claim 1, further comprising determining amino acid sequences of heavy chain and light chain variable regions of the identified candidate antibody.

7. The method of claim 1, wherein the phenotype is a cellular response or signaling activity of the cell.

8. The method of claim 1, wherein the cell type is a stem cell type, and the phenotype is cell differentiation.

9. The method of claim 1, wherein the phenotype is mediated via a target molecule.

10. The method of claim 9, wherein the target molecule is a signaling receptor of the cell type.

11. The method of claim 10, wherein the receptor is a receptor for a secreted hormone or cytokine.

12. The method of claim 9, wherein the identified antibody is a heterodimeric bispecific antibody.

13. The method of claim 12, wherein the bispecific antibody binds to two different epitopes on a target molecule.

14. The method of claim 9, wherein the modulator antibody agonizes the target molecule.

15. The method of claim 9, wherein the modulator antibody antagonizes the target molecule or antagonizes an inhibitor of the target molecule.

16. The method of claim 15, wherein the selection is performed in the presence of the inhibitor.

17. The method of claim 9, further comprising screening the library of candidate antibodies to identify binders of the target molecule prior to expressing the binder antibodies in the cell population for phenotypic selection.

18. The method of claim 17, wherein the binder antibodies of the target molecule are identified via phage display.

19. The method of claim 1, wherein the phenotype is expression of a target molecule or marker gene in the cell type.

20. The method of claim 19, wherein the target molecule is a cell surface receptor.

* * * * *